United States Patent [19]
Hoey

[11] Patent Number: 5,708,158
[45] Date of Patent: Jan. 13, 1998

[54] NUCLEAR FACTORS AND BINDING ASSAYS

[75] Inventor: Timothy Hoey, Woodside, Calif.

[73] Assignee: Tularik Inc., South San Francisco, Calif.

[21] Appl. No.: 818,823

[22] Filed: Mar. 14, 1997

Related U.S. Application Data

[60] Division of Ser. No. 396,479, Mar. 2, 1995, Pat. No. 5,612,455, which is a continuation-in-part of Ser. No. 270,653, Jul. 5, 1994, abandoned.

[51] Int. Cl.⁶ .......................... C12N 15/12; C12N 15/11
[52] U.S. Cl. .......................... 536/23.5; 536/23.1
[58] Field of Search .......................... 536/23.1, 23.5

[56] References Cited

PUBLICATIONS

Li et al, PNAS (USA), Sep., 1991, vol. 88: pp. 7739–7743.

*Primary Examiner*—George C. Elliott
*Assistant Examiner*—Terry A. McKelvey
*Attorney, Agent, or Firm*—Richard Aron Osman

[57] ABSTRACT

The invention provides methods and compositions for identifying pharmacological agents useful in the diagnosis or treatment of disease associated with the expression of a gene modulated by a transcription complex containing at least a human nuclear factor of activated T-cells (hNFAT). The materials include a family of hNFAT proteins, active fragments thereof, and nucleic acids encoding them. The methods are particularly suited to high-throughput screening where one or more steps are performed by a computer controlled electromechanical robot comprising an axial rotatable arm.

12 Claims, No Drawings

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 3478 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 223..2987

( x i ) SEQUENCE DESCRIPTION: SEQ ID NO:1:

```
GGAGCAGGAA  GCTCGCGCCG  CCGTCGCCGC  CGCCGCTCAG  CTTCCCCGGG  CGCGTCCAGG      60

ACCCGCTGCG  CCAGGCGCGC  CGTCCCCGGA  CCCGGCGTGC  GTCCCTACGA  GGAAAGGGAC     120

CCCGCCGCTC  GAGCCGCCTC  CGCCAGCCCC  ACTGCGAGGG  GTCCCAGAGC  CAGCCGCGCC     180

CGCCCTCGCC  CCCGGCCCCG  CAGCCTTCCC  GCCCTGCGCG  CC ATG AAC GCC CCC         234
                                                  Met Asn Ala Pro
                                                    1

GAG CGG CAG CCC CAA CCC GAC GGC GGG GAC GCC CCA GGC CAC GAG CCT            282
Glu Arg Gln Pro Gln Pro Asp Gly Gly Asp Ala Pro Gly His Glu Pro
  5              10                  15                  20

GGG GGC AGC CCC CAA GAC GAG CTT GAC TTC TCC ATC CTC TTC GAC TAT            330
Gly Gly Ser Pro Gln Asp Glu Leu Asp Phe Ser Ile Leu Phe Asp Tyr
              25                  30                  35

GAG TAT TTG AAT CCG AAC GAA GAA GAG CCG AAT GCA CAT AAG GTC GCC            378
Glu Tyr Leu Asn Pro Asn Glu Glu Glu Pro Asn Ala His Lys Val Ala
          40                  45                  50

AGC CCA CCC TCC GGA CCC GCA TAC CCC GAT GAT GTC CTG GAC TAT GGC            426
Ser Pro Pro Ser Gly Pro Ala Tyr Pro Asp Asp Val Leu Asp Tyr Gly
      55                  60                  65

CTC AAG CCA TAC AGC CCC CTT GCT AGT CTC TCT GGC GAG CCC CCC GGC            474
Leu Lys Pro Tyr Ser Pro Leu Ala Ser Leu Ser Gly Glu Pro Pro Gly
  70                  75                  80
```

-continued

| | | | | | | | | | | | | | | | | |
|---|---|---|---|---|---|---|---|---|---|---|---|---|---|---|---|---|
| CGA | TTC | GGA | GAG | CCG | GAT | AGG | GTA | GGG | CCG | CAG | AAG | TTT | CTG | AGC | GCG | 522 |
| Arg | Phe | Gly | Glu | Pro | Asp | Arg | Val | Gly | Pro | Gln | Lys | Phe | Leu | Ser | Ala | |
| 85 | | | | 90 | | | | | 95 | | | | | | 100 | |
| GCC | AAG | CCA | GCA | GGG | GCC | TCG | GGC | CTG | AGC | CCT | CGG | ATC | GAG | ATC | ACT | 570 |
| Ala | Lys | Pro | Ala | Gly | Ala | Ser | Gly | Leu | Ser | Pro | Arg | Ile | Glu | Ile | Thr | |
| | | | | 105 | | | | | 110 | | | | | 115 | | |
| CCG | TCC | CAC | GAA | CTG | ATC | CAG | GCA | GTG | GGG | CCC | CTC | CGC | ATG | AGA | GAC | 618 |
| Pro | Ser | His | Glu | Leu | Ile | Gln | Ala | Val | Gly | Pro | Leu | Arg | Met | Arg | Asp | |
| | | | 120 | | | | | 125 | | | | | 130 | | | |
| GCG | GGC | CTC | CTG | GTG | GAG | CAG | CCG | CCC | CTG | GCC | GGG | GTG | GCC | GCC | AGC | 666 |
| Ala | Gly | Leu | Leu | Val | Glu | Gln | Pro | Pro | Leu | Ala | Gly | Val | Ala | Ala | Ser | |
| | | | 135 | | | | | 140 | | | | | 145 | | | |
| CCG | AGG | TTC | ACC | CTG | CCC | GTG | CCC | GGC | TTC | GAG | GGC | TAC | CGC | GAG | CCG | 714 |
| Pro | Arg | Phe | Thr | Leu | Pro | Val | Pro | Gly | Phe | Glu | Gly | Tyr | Arg | Glu | Pro | |
| | 150 | | | | | 155 | | | | | 160 | | | | | |
| CTT | TGC | TTG | AGC | CCC | GCT | AGC | AGC | GGC | TCC | TCT | GCC | AGC | TTC | ATT | TCT | 762 |
| Leu | Cys | Leu | Ser | Pro | Ala | Ser | Ser | Gly | Ser | Ser | Ala | Ser | Phe | Ile | Ser | |
| 165 | | | | | 170 | | | | | 175 | | | | | 180 | |
| GAC | ACC | TTC | TCC | CCC | TAC | ACC | TCG | CCC | TGC | GTC | TCG | CCC | AAT | AAC | GGC | 810 |
| Asp | Thr | Phe | Ser | Pro | Tyr | Thr | Ser | Pro | Cys | Val | Ser | Pro | Asn | Asn | Gly | |
| | | | | 185 | | | | | 190 | | | | | 195 | | |
| GGG | CCC | GAC | GAC | CTG | TGT | CCG | CAG | TTT | CAA | AAC | ATC | CCT | GCT | CAT | TAT | 858 |
| Gly | Pro | Asp | Asp | Leu | Cys | Pro | Gln | Phe | Gln | Asn | Ile | Pro | Ala | His | Tyr | |
| | | | 200 | | | | | 205 | | | | | 210 | | | |
| TCC | CCC | AGA | ACC | TCG | CCA | ATA | ATG | TCA | CCT | CGA | ACC | AGC | CTC | GCC | GAG | 906 |
| Ser | Pro | Arg | Thr | Ser | Pro | Ile | Met | Ser | Pro | Arg | Thr | Ser | Leu | Ala | Glu | |
| | | | 215 | | | | 220 | | | | | 225 | | | | |
| GAC | AGC | TGC | CTG | GGC | CGC | CAC | TCG | CCC | GTG | CCC | CGT | CCG | GCC | TCC | CGC | 954 |
| Asp | Ser | Cys | Leu | Gly | Arg | His | Ser | Pro | Val | Pro | Arg | Pro | Ala | Ser | Arg | |
| | 230 | | | | | 235 | | | | | 240 | | | | | |
| TCC | TCA | TCG | CCT | GGT | GCC | AAG | CGG | AGG | CAT | TCG | TGC | GCC | GAG | GCC | TTG | 1002 |
| Ser | Ser | Ser | Pro | Gly | Ala | Lys | Arg | Arg | His | Ser | Cys | Ala | Glu | Ala | Leu | |
| 245 | | | | | 250 | | | | | 255 | | | | | 260 | |
| GTT | GCC | CTG | CCG | CCC | GGA | GCC | TCA | CCC | CAG | CGC | TCC | CGG | AGC | CCC | TCG | 1050 |
| Val | Ala | Leu | Pro | Pro | Gly | Ala | Ser | Pro | Gln | Arg | Ser | Arg | Ser | Pro | Ser | |
| | | | | 265 | | | | | 270 | | | | | 275 | | |
| CCG | CAG | CCC | TCA | TCT | CAC | GTG | GCA | CCC | CAG | GAC | CAC | GGC | TCC | CCG | GCT | 1098 |
| Pro | Gln | Pro | Ser | Ser | His | Val | Ala | Pro | Gln | Asp | His | Gly | Ser | Pro | Ala | |
| | | | 280 | | | | | 285 | | | | | 290 | | | |
| GGG | TAC | CCC | CCT | GTG | GCT | GGC | TCT | GCC | GTG | ATC | ATG | GAT | GCC | CTG | AAC | 1146 |
| Gly | Tyr | Pro | Pro | Val | Ala | Gly | Ser | Ala | Val | Ile | Met | Asp | Ala | Leu | Asn | |
| | | 295 | | | | | 300 | | | | | 305 | | | | |
| AGC | CTC | GCC | ACG | GAC | TCG | CCT | TGT | GGG | ATC | CCC | CCC | AAG | ATG | TGG | AAG | 1194 |
| Ser | Leu | Ala | Thr | Asp | Ser | Pro | Cys | Gly | Ile | Pro | Pro | Lys | Met | Trp | Lys | |
| | 310 | | | | | 315 | | | | | 320 | | | | | |
| ACC | AGC | CCT | GAC | CCC | TCG | CCG | GTG | TCT | GCC | GCC | CCA | TCC | AAG | GCC | GGC | 1242 |
| Thr | Ser | Pro | Asp | Pro | Ser | Pro | Val | Ser | Ala | Ala | Pro | Ser | Lys | Ala | Gly | |
| 325 | | | | | 330 | | | | | 335 | | | | | 340 | |
| CTG | CCT | CGC | CAC | ATC | TAC | CCG | GCC | GTG | GAG | TTC | CTG | GGG | CCC | TGC | GAG | 1290 |
| Leu | Pro | Arg | His | Ile | Tyr | Pro | Ala | Val | Glu | Phe | Leu | Gly | Pro | Cys | Glu | |
| | | | | 345 | | | | | 350 | | | | | 355 | | |
| CAG | GGC | GAG | AGG | AGA | AAC | TCG | GCT | CCA | GAA | TCC | ATC | CTG | CTG | GTT | CCG | 1338 |
| Gln | Gly | Glu | Arg | Arg | Asn | Ser | Ala | Pro | Glu | Ser | Ile | Leu | Leu | Val | Pro | |
| | | | 360 | | | | | 365 | | | | | 370 | | | |
| CCC | ACT | TGG | CCC | AAG | CCG | CTG | GTG | CCT | GCC | ATT | CCC | ATC | TGC | AGC | ATC | 1386 |
| Pro | Thr | Trp | Pro | Lys | Pro | Leu | Val | Pro | Ala | Ile | Pro | Ile | Cys | Ser | Ile | |
| | | 375 | | | | | 380 | | | | | 385 | | | | |
| CCA | GTG | ACT | GCA | TCC | CTC | CCT | CCA | CTT | GAG | TGG | CCG | CTG | TCC | AGT | CAG | 1434 |
| Pro | Val | Thr | Ala | Ser | Leu | Pro | Pro | Leu | Glu | Trp | Pro | Leu | Ser | Ser | Gln | |
| | 390 | | | | | 395 | | | | | 400 | | | | | |

| | | | | | | | | | | | | | | | | |
|---|---|---|---|---|---|---|---|---|---|---|---|---|---|---|---|---|
| TCA | GGC | TCT | TAC | GAG | CTG | CGG | ATC | GAG | GTG | CAG | CCC | AAG | CCA | CAT | CAC | 1482 |
| Ser 405 | Gly | Ser | Tyr | Glu 410 | Leu | Arg | Ile | Glu | Val 415 | Gln | Pro | Lys | Pro | His | His 420 | |
| CGG | GCC | CAC | TAT | GAG | ACA | GAA | GGC | AGC | CGA | GGG | GCT | GTC | AAA | GCT | CCA | 1530 |
| Arg | Ala | His | Tyr | Glu 425 | Thr | Glu | Gly | Ser | Arg 430 | Gly | Ala | Val | Lys | Ala 435 | Pro | |
| ACT | GGA | GGC | CAC | CCT | GTG | GTT | CAG | CTC | CAT | GGC | TAC | ATG | GAA | AAC | AAG | 1578 |
| Thr | Gly | Gly | His 440 | Pro | Val | Val | Gln | Leu 445 | His | Gly | Tyr | Met | Glu 450 | Asn | Lys | |
| CCT | CTG | GGA | CTT | CAG | ATC | TTC | ATT | GGG | ACA | GCT | GAT | GAG | CGG | ATC | CTT | 1626 |
| Pro | Leu | Gly 455 | Leu | Gln | Ile | Phe | Ile 460 | Gly | Thr | Ala | Asp | Glu 465 | Arg | Ile | Leu | |
| AAG | CCG | CAC | GCC | TTC | TAC | CAG | GTG | CAC | CGA | ATC | ACG | GGG | AAA | ACT | GTC | 1674 |
| Lys | Pro 470 | His | Ala | Phe | Tyr | Gln 475 | Val | His | Arg | Ile | Thr 480 | Gly | Lys | Thr | Val | |
| ACC | ACC | ACC | AGC | TAT | GAG | AAG | ATA | GTG | GGC | AAC | ACC | AAA | GTC | CTG | GAG | 1722 |
| Thr 485 | Thr | Thr | Ser | Tyr | Glu 490 | Lys | Ile | Val | Gly | Asn 495 | Thr | Lys | Val | Leu | Glu 500 | |
| ATA | CCC | TTG | GAG | CCC | AAA | AAC | AAC | ATG | AGG | GCA | ACC | ATC | GAC | TGT | GCG | 1770 |
| Ile | Pro | Leu | Glu | Pro 505 | Lys | Asn | Asn | Met | Arg 510 | Ala | Thr | Ile | Asp | Cys 515 | Ala | |
| GGG | ATC | TTG | AAG | CTT | AGA | AAC | GCC | GAC | ATT | GAG | CTG | CGG | AAA | GGC | GAG | 1818 |
| Gly | Ile | Leu | Lys 520 | Leu | Arg | Asn | Ala | Asp 525 | Ile | Glu | Leu | Arg | Lys 530 | Gly | Glu | |
| ACG | GAC | ATT | GGA | AGA | AAG | AAC | ACG | CGG | GTG | AGA | CTG | GTT | TTC | CGA | GTT | 1866 |
| Thr | Asp | Ile 535 | Gly | Arg | Lys | Asn | Thr 540 | Arg | Val | Arg | Leu | Val 545 | Phe | Arg | Val | |
| CAC | ATC | CCA | GAG | TCC | AGT | GGC | AGA | ATC | GTC | TCT | TTA | CAG | ACT | GCA | TCT | 1914 |
| His | Ile 550 | Pro | Glu | Ser | Ser | Gly 555 | Arg | Ile | Val | Ser | Leu 560 | Gln | Thr | Ala | Ser | |
| AAC | CCC | ATC | GAG | TGC | TCC | CAG | CGA | TCT | GCT | CAC | GAG | CTG | CCC | ATG | GTT | 1962 |
| Asn 565 | Pro | Ile | Glu | Cys | Ser 570 | Gln | Arg | Ser | Ala | His 575 | Glu | Leu | Pro | Met | Val 580 | |
| GAA | AGA | CAA | GAC | ACA | GAC | AGC | TGC | CTG | GTC | TAT | GGC | GGC | CAG | CAA | ATG | 2010 |
| Glu | Arg | Gln | Asp | Thr 585 | Asp | Ser | Cys | Leu | Val 590 | Tyr | Gly | Gly | Gln | Gln 595 | Met | |
| ATC | CTC | ACG | GGG | CAG | AAC | TTT | ACA | TCC | GAG | TCC | AAA | GTT | GTG | TTT | ACT | 2058 |
| Ile | Leu | Thr | Gly 600 | Gln | Asn | Phe | Thr | Ser 605 | Glu | Ser | Lys | Val | Val 610 | Phe | Thr | |
| GAG | AAG | ACC | ACA | GAT | GGA | CAG | CAA | ATT | TGG | GAG | ATG | GAA | GCC | ACG | GTG | 2106 |
| Glu | Lys | Thr 615 | Thr | Asp | Gly | Gln | Gln 620 | Ile | Trp | Glu | Met | Glu 625 | Ala | Thr | Val | |
| GAT | AAG | GAC | AAG | AGC | CAG | CCC | AAC | ATG | CTT | TTT | GTT | GAG | ATC | CCT | GAA | 2154 |
| Asp | Lys 630 | Asp | Lys | Ser | Gln | Pro 635 | Asn | Met | Leu | Phe | Val 640 | Glu | Ile | Pro | Glu | |
| TAT | CGG | AAC | AAG | CAT | ATC | CGC | ACA | CCT | GTA | AAA | GTG | AAC | TTC | TAC | GTC | 2202 |
| Tyr 645 | Arg | Asn | Lys | His | Ile 650 | Arg | Thr | Pro | Val | Lys 655 | Val | Asn | Phe | Tyr | Val 660 | |
| ATC | AAT | GGG | AAG | AGA | AAA | CGA | AGT | CAG | CCT | CAG | CAC | TTT | ACC | TAC | CAC | 2250 |
| Ile | Asn | Gly | Lys | Arg 665 | Lys | Arg | Ser | Gln | Pro 670 | Gln | His | Phe | Thr | Tyr 675 | His | |
| CCA | GTC | CCA | GCC | ATC | AAG | ACG | GAG | CCC | ACG | GAT | GAA | TAT | GAC | CCC | ACT | 2298 |
| Pro | Val | Pro | Ala 680 | Ile | Lys | Thr | Glu | Pro 685 | Thr | Asp | Glu | Tyr | Asp 690 | Pro | Thr | |
| CTG | ATC | TGC | AGC | CCC | ACC | CAT | GGA | GGC | CTG | GGG | AGC | CAG | CCT | TAC | TAC | 2346 |
| Leu | Ile | Cys 695 | Ser | Pro | Thr | His | Gly 700 | Gly | Leu | Gly | Ser | Gln 705 | Pro | Tyr | Tyr | |
| CCC | CAG | CAC | CCG | ATG | GTG | GCC | GAG | TCC | CCC | TCC | TGC | CTC | GTG | GCC | ACC | 2394 |
| Pro | Gln | His 710 | Pro | Met | Val | Ala | Glu 715 | Ser | Pro | Ser | Cys | Leu 720 | Val | Ala | Thr | |

```
ATG GCT CCC TGC CAG CAG TTC CGC ACG GGG CTC TCA TCC CCT GAC GCC        2442
Met Ala Pro Cys Gln Gln Phe Arg Thr Gly Leu Ser Ser Pro Asp Ala
725             730                 735                 740

CGC TAC CAG CAA CAG AAC CCA GCG GCC GTA CTC TAC CAG CGG AGC AAG        2490
Arg Tyr Gln Gln Gln Asn Pro Ala Ala Val Leu Tyr Gln Arg Ser Lys
                745                 750                 755

AGC CTG AGC CCC AGC CTG CTG GGC TAT CAG CAG CCG GCC CTC ATG GCC        2538
Ser Leu Ser Pro Ser Leu Leu Gly Tyr Gln Gln Pro Ala Leu Met Ala
            760                 765                 770

GCC CCG CTG TCC CTT GCG GAC GCT CAC CGC TCT GTG CTG GTG CAC GCC        2586
Ala Pro Leu Ser Leu Ala Asp Ala His Arg Ser Val Leu Val His Ala
        775                 780                 785

GGC TCC CAG GGC CAG AGC TCA GCC CTG CTC CAC CCC TCT CCG ACC AAC        2634
Gly Ser Gln Gly Gln Ser Ser Ala Leu Leu His Pro Ser Pro Thr Asn
790                 795                 800

CAG CAG GCC TCG CCT GTG ATC CAC TAC TCA CCC ACC AAC CAG CAG CTG        2682
Gln Gln Ala Ser Pro Val Ile His Tyr Ser Pro Thr Asn Gln Gln Leu
805             810                 815                 820

CGC TGC GGA AGC CAC CAG GAG TTC CAG CAC ATC ATG TAC TGC GAG AAT        2730
Arg Cys Gly Ser His Gln Glu Phe Gln His Ile Met Tyr Cys Glu Asn
                825                 830                 835

TTC GCA CCA GGC ACC ACC AGA CCT GGC CCG CCC CCG GTC AGT CAA GGT        2778
Phe Ala Pro Gly Thr Thr Arg Pro Gly Pro Pro Pro Val Ser Gln Gly
            840                 845                 850

CAG AGG CTG AGC CCG GGT TCC TAC CCC ACA GTC ATT CAG CAG CAG AAT        2826
Gln Arg Leu Ser Pro Gly Ser Tyr Pro Thr Val Ile Gln Gln Gln Asn
        855                 860                 865

GCC ACG AGC CAA AGA GCC GCC AAA AAC GGA CCC CCG GTC AGT GAC CAA        2874
Ala Thr Ser Gln Arg Ala Ala Lys Asn Gly Pro Pro Val Ser Asp Gln
870                 875                 880

AAG GAA GTA TTA CCT GCG GGG GTG ACC ATT AAA CAG GAG CAG AAC TTG        2922
Lys Glu Val Leu Pro Ala Gly Val Thr Ile Lys Gln Glu Gln Asn Leu
885             890                 895                 900

GAC CAG ACC TAC TTG GAT GAT GAG CTG ATA GAC ACA CAC CTT AGC TGG        2970
Asp Gln Thr Tyr Leu Asp Asp Glu Leu Ile Asp Thr His Leu Ser Trp
                905                 910                 915

ATA CAA AAC ATA TTA TG AAACAGAATG ACTGTGATCT TTGATCCGAG               3017
Ile Gln Asn Ile Leu
                920

AAATCAAAGT TAAAGTTAAT GAAATTATCA GGAAGGAGTT TTCAGGACCT CCTGCCAGAA     3077

ATCAGACGTA AAAGAAGCCA TTATAGCAAG ACACCTTCTG TATCTGACCC CTCGGAGCCC     3137

TCCACAGCCC CTCACCTTCT GTCTCCTTTC ATGTTCATCT CCCAGCCCGG AGTCCACACG     3197

CGGATCAATG TATGGGCACT AAGCGGACTC TCACTTAAGG AGCTCGCCAC CTCCCTCTAA     3257

ACACCAGAGA GAACTCTTCT TTTCGGTTTA TGTTTAAAT CCCAGAGAGC ATCCTGGTTG      3317

ATCTTAATGG TGTTCCGTCC AAATAGTAAG CACCTGCTGA CCAAAAGCAC ATTCTACATG     3377

AGACAGGACA CTGGAACTCT CCTGAGAACA GAGTGACTGG AGCTTGGGGG GATGGACGGG     3437

GGACAGAAGA TGTGGGCACT GTGATTAAAC CCCAGCCCTT G                        3478
```

( 2 ) INFORMATION FOR SEQ ID NO:2:

( i ) SEQUENCE CHARACTERISTICS:
        ( A ) LENGTH: 921 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asn Ala Pro Glu Arg Gln Pro Gln Pro Asp Gly Gly Asp Ala Pro
 1               5               10              15
Gly His Glu Pro Gly Gly Ser Pro Gln Asp Glu Leu Asp Phe Ser Ile
            20              25              30
Leu Phe Asp Tyr Glu Tyr Leu Asn Pro Asn Glu Glu Pro Asn Ala
        35              40              45
His Lys Val Ala Ser Pro Ser Gly Pro Ala Tyr Pro Asp Asp Val
    50              55              60
Leu Asp Tyr Gly Leu Lys Pro Tyr Ser Pro Leu Ala Ser Leu Ser Gly
65              70              75              80
Glu Pro Pro Gly Arg Phe Gly Glu Pro Asp Arg Val Gly Pro Gln Lys
            85              90              95
Phe Leu Ser Ala Ala Lys Pro Ala Gly Ala Ser Gly Leu Ser Pro Arg
            100             105             110
Ile Glu Ile Thr Pro Ser His Glu Leu Ile Gln Ala Val Gly Pro Leu
        115             120             125
Arg Met Arg Asp Ala Gly Leu Leu Val Glu Gln Pro Leu Ala Gly
    130             135             140
Val Ala Ala Ser Pro Arg Phe Thr Leu Pro Val Pro Gly Phe Glu Gly
145             150             155             160
Tyr Arg Glu Pro Leu Cys Leu Ser Pro Ala Ser Ser Gly Ser Ser Ala
            165             170             175
Ser Phe Ile Ser Asp Thr Phe Ser Pro Tyr Thr Ser Pro Cys Val Ser
            180             185             190
Pro Asn Asn Gly Gly Pro Asp Asp Leu Cys Pro Gln Phe Gln Asn Ile
        195             200             205
Pro Ala His Tyr Ser Pro Arg Thr Ser Pro Ile Met Ser Pro Arg Thr
    210             215             220
Ser Leu Ala Glu Asp Ser Cys Leu Gly Arg His Ser Pro Val Pro Arg
225             230             235             240
Pro Ala Ser Arg Ser Ser Ser Pro Gly Ala Lys Arg Arg His Ser Cys
            245             250             255
Ala Glu Ala Leu Val Ala Leu Pro Pro Gly Ala Ser Pro Gln Arg Ser
            260             265             270
Arg Ser Pro Ser Pro Gln Pro Ser Ser His Val Ala Pro Gln Asp His
        275             280             285
Gly Ser Pro Ala Gly Tyr Pro Pro Val Ala Gly Ser Ala Val Ile Met
290             295             300
Asp Ala Leu Asn Ser Leu Ala Thr Asp Ser Pro Cys Gly Ile Pro Pro
305             310             315             320
Lys Met Trp Lys Thr Ser Pro Asp Pro Ser Pro Val Ser Ala Ala Pro
            325             330             335
Ser Lys Ala Gly Leu Pro Arg His Ile Tyr Pro Ala Val Glu Phe Leu
        340             345             350
Gly Pro Cys Glu Gln Gly Glu Arg Arg Asn Ser Ala Pro Glu Ser Ile
        355             360             365
Leu Leu Val Pro Pro Thr Trp Pro Lys Pro Leu Val Pro Ala Ile Pro
370             375             380
Ile Cys Ser Ile Pro Val Thr Ala Ser Leu Pro Pro Leu Glu Trp Pro
385             390             395             400
Leu Ser Ser Gln Ser Gly Ser Tyr Glu Leu Arg Ile Glu Val Gln Pro
            405             410             415
Lys Pro His His Arg Ala His Tyr Glu Thr Glu Gly Ser Arg Gly Ala
        420             425             430
```

-continued

```
Val Lys Ala Pro Thr Gly Gly His Pro Val Val Gln Leu His Gly Tyr
        435                 440                 445

Met Glu Asn Lys Pro Leu Gly Leu Gln Ile Phe Ile Gly Thr Ala Asp
    450                 455                 460

Glu Arg Ile Leu Lys Pro His Ala Phe Tyr Gln Val His Arg Ile Thr
465                 470                 475                 480

Gly Lys Thr Val Thr Thr Thr Ser Tyr Glu Lys Ile Val Gly Asn Thr
                485                 490                 495

Lys Val Leu Glu Ile Pro Leu Glu Pro Lys Asn Asn Met Arg Ala Thr
            500                 505                 510

Ile Asp Cys Ala Gly Ile Leu Lys Leu Arg Asn Ala Asp Ile Glu Leu
        515                 520                 525

Arg Lys Gly Glu Thr Asp Ile Gly Arg Lys Asn Thr Arg Val Arg Leu
530                 535                 540

Val Phe Arg Val His Ile Pro Glu Ser Ser Gly Arg Ile Val Ser Leu
545                 550                 555                 560

Gln Thr Ala Ser Asn Pro Ile Glu Cys Ser Gln Arg Ser Ala His Glu
                565                 570                 575

Leu Pro Met Val Glu Arg Gln Asp Thr Asp Ser Cys Leu Val Tyr Gly
            580                 585                 590

Gly Gln Gln Met Ile Leu Thr Gly Gln Asn Phe Thr Ser Glu Ser Lys
        595                 600                 605

Val Val Phe Thr Glu Lys Thr Thr Asp Gly Gln Gln Ile Trp Glu Met
610                 615                 620

Glu Ala Thr Val Asp Lys Asp Lys Ser Gln Pro Asn Met Leu Phe Val
625                 630                 635                 640

Glu Ile Pro Glu Tyr Arg Asn Lys His Ile Arg Thr Pro Val Lys Val
                645                 650                 655

Asn Phe Tyr Val Ile Asn Gly Lys Arg Lys Arg Ser Gln Pro Gln His
            660                 665                 670

Phe Thr Tyr His Pro Val Pro Ala Ile Lys Thr Glu Pro Thr Asp Glu
        675                 680                 685

Tyr Asp Pro Thr Leu Ile Cys Ser Pro Thr His Gly Gly Leu Gly Ser
    690                 695                 700

Gln Pro Tyr Tyr Pro Gln His Pro Met Val Ala Glu Ser Pro Ser Cys
705                 710                 715                 720

Leu Val Ala Thr Met Ala Pro Cys Gln Gln Phe Arg Thr Gly Leu Ser
                725                 730                 735

Ser Pro Asp Ala Arg Tyr Gln Gln Gln Asn Pro Ala Ala Val Leu Tyr
            740                 745                 750

Gln Arg Ser Lys Ser Leu Ser Pro Ser Leu Leu Gly Tyr Gln Gln Pro
        755                 760                 765

Ala Leu Met Ala Ala Pro Leu Ser Leu Ala Asp Ala His Arg Ser Val
    770                 775                 780

Leu Val His Ala Gly Ser Gln Gly Gln Ser Ser Ala Leu Leu His Pro
785                 790                 795                 800

Ser Pro Thr Asn Gln Gln Ala Ser Pro Val Ile His Tyr Ser Pro Thr
                805                 810                 815

Asn Gln Gln Leu Arg Cys Gly Ser His Gln Glu Phe Gln His Ile Met
            820                 825                 830

Tyr Cys Glu Asn Phe Ala Pro Gly Thr Thr Arg Pro Gly Pro Pro Pro
        835                 840                 845

Val Ser Gln Gly Gln Arg Leu Ser Pro Gly Ser Tyr Pro Thr Val Ile
```

```
                850                    855                    860
Gln Gln Gln Asn Ala Thr Ser Gln Arg Ala Ala Lys Asn Gly Pro Pro
865                 870                 875                 880

Val Ser Asp Gln Lys Glu Val Leu Pro Ala Gly Val Thr Ile Lys Gln
                885                 890                 895

Glu Gln Asn Leu Asp Gln Thr Tyr Leu Asp Asp Glu Leu Ile Asp Thr
            900                 905                 910

His Leu Ser Trp Ile Gln Asn Ile Leu
            915                 920
```

( 2 ) INFORMATION FOR SEQ ID NO:3:

( i ) SEQUENCE CHARACTERISTICS:
        ( A ) LENGTH: 2743 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 240..2390

( x i ) SEQUENCE DESCRIPTION: SEQ ID NO:3:

```
GAATTCCGCA GGGCGCGGGC ACCGGGGCGC GGGCAGGGCT CGGAGCCACC GCGCAGGTCC      60

TAGGGCCGCG GCCGGGCCCC GCCACGCGCG CACACGCCCC TCGATGACTT TCCTCCGGGG     120

CGCGCGGCGC TGAGCCCGGG GCGAGGGCTG TCTTCCCGGA GACCCGACCC CGGCAGCGCG     180

GGGCGGCCAC TTCTCCTGTG CCTCCGCCCG CTGCTCCACT CCCCGCCGCC GCCGCGCGG     239

ATG CCA AGC ACC AGC TTT CCA GTC CCT TCC AAG TTT CCA CTT GGC CCT      287
Met Pro Ser Thr Ser Phe Pro Val Pro Ser Lys Phe Pro Leu Gly Pro
        925                 930                 935

GCG GCT GCG GTC TTC GGG AGA GGA GAA ACT TTG GGG CCC GCG CCG CGC      335
Ala Ala Ala Val Phe Gly Arg Gly Glu Thr Leu Gly Pro Ala Pro Arg
            940                 945                 950

GCC GGC GGC ACC ATG AAG TCA GCG GAG GAA GAA CAC TAT GGC TAT GCA      383
Ala Gly Gly Thr Met Lys Ser Ala Glu Glu Glu His Tyr Gly Tyr Ala
955                 960                 965

TCC TCC AAC GTC AGC CCC GCC CTG CCG CTC CCC ACG GCG CAC TCC ACC      431
Ser Ser Asn Val Ser Pro Ala Leu Pro Leu Pro Thr Ala His Ser Thr
970                 975                 980                 985

CTG CCG GCC CCG TGC CAC AAC CTT CAG ACC TCC ACA CCG GGC ATC ATC      479
Leu Pro Ala Pro Cys His Asn Leu Gln Thr Ser Thr Pro Gly Ile Ile
                990                 995                 1000

CCG CCG GCG GAT CAC CCC TCG GGG TAC GGA GCA GCT TTG GAC GGT GGG      527
Pro Pro Ala Asp His Pro Ser Gly Tyr Gly Ala Ala Leu Asp Gly Gly
            1005                1010                1015

CCC GCG GGC TAC TTC CTC TCC TCC GGC CAC ACC AGG CCT GAT GGG GCC      575
Pro Ala Gly Tyr Phe Leu Ser Ser Gly His Thr Arg Pro Asp Gly Ala
        1020                1025                1030

CCT GCC CTG GAG AGT CCT CGC ATC GAG ATA ACC TCG TGC TTG GGC CTG      623
Pro Ala Leu Glu Ser Pro Arg Ile Glu Ile Thr Ser Cys Leu Gly Leu
    1035                1040                1045

TAC CAC AAC AAT AAC CAG TTT TTC CAC GAT GTG GAG GTG GAA GAC GTC      671
Tyr His Asn Asn Asn Gln Phe Phe His Asp Val Glu Val Glu Asp Val
1050                1055                1060                1065

CTC CCT AGC TCC AAA CGG TCC CCC TCC ACG GCC ACG CTG AGT CTG CCC      719
Leu Pro Ser Ser Lys Arg Ser Pro Ser Thr Ala Thr Leu Ser Leu Pro
                1070                1075                1080

AGC CTG GAG GCC TAC AGA GAC CCC TCG TGC CTG AGC CCG GCC AGC AGC      767
```

```
Ser Leu Glu Ala Tyr Arg Asp Pro Ser Cys Leu Ser Pro Ala Ser Ser
                1085                1090                1095

CTG TCC TCC CGG AGC TGC AAC TCA GAG GCC TCC TCC TAC GAG TCC AAC          815
Leu Ser Ser Arg Ser Cys Asn Ser Glu Ala Ser Ser Tyr Glu Ser Asn
1100                    1105                    1110

TAC TCG TAC CCG TAC GCG TCC CCC CAG ACG TCG CCA TGG CAG TCT CCC          863
Tyr Ser Tyr Pro Tyr Ala Ser Pro Gln Thr Ser Pro Trp Gln Ser Pro
     1115                1120                1125

TGC GTG TCT CCC AAG ACC ACG GAC CCC GAG GAG GGC TTT CCC CGC GGG          911
Cys Val Ser Pro Lys Thr Thr Asp Pro Glu Glu Gly Phe Pro Arg Gly
1130                1135                1140                1145

CTG GGG GCC TGC ACA CTG CTG GGT TCC CCG CAG CAC TCC CCC TCC ACC          959
Leu Gly Ala Cys Thr Leu Leu Gly Ser Pro Gln His Ser Pro Ser Thr
         1150                1155                1160

TCG CCC CGC GCC AGC GTC ACT GAG GAG AGC TGG CTG GGT GCC CGC TCC         1007
Ser Pro Arg Ala Ser Val Thr Glu Glu Ser Trp Leu Gly Ala Arg Ser
              1165                1170                1175

TCC AGA CCC GCG TCC CCT TGC AAC AAG AGG AAG TAC AGC CTC AAC GGC         1055
Ser Arg Pro Ala Ser Pro Cys Asn Lys Arg Lys Tyr Ser Leu Asn Gly
         1180                1185                1190

CGG CAG CCG CCC TAC TCA CCC CAC CAC TCG CCC ACG CCG TCC CCG CAC         1103
Arg Gln Pro Pro Tyr Ser Pro His His Ser Pro Thr Pro Ser Pro His
     1195                1200                1205

GGC TCC CCG CGG GTC AGC GTG ACC GAC GAC TCG TGG TTG GGC AAC ACC         1151
Gly Ser Pro Arg Val Ser Val Thr Asp Asp Ser Trp Leu Gly Asn Thr
1210                1215                1220                1225

ACC CAG TAC ACC AGC TCG GCC ATC GTG GCC GCC ATC AAC GCG CTG ACC         1199
Thr Gln Tyr Thr Ser Ser Ala Ile Val Ala Ala Ile Asn Ala Leu Thr
         1230                1235                1240

ACC GAC AGC AGC CTG GAC CTG GGA GAT GGC GTC CCT GTC AAG TCC CGC         1247
Thr Asp Ser Ser Leu Asp Leu Gly Asp Gly Val Pro Val Lys Ser Arg
              1245                1250                1255

AAG ACC ACC CTG GAG CAG CCG CCC TCA GTG GCG CTC AAG GTG GAG CCC         1295
Lys Thr Thr Leu Glu Gln Pro Pro Ser Val Ala Leu Lys Val Glu Pro
         1260                1265                1270

GTC GGG GAG GAC CTG GGC AGC CCC CCG CCC CCG GCC GAC TTC GCG CCC         1343
Val Gly Glu Asp Leu Gly Ser Pro Pro Pro Pro Ala Asp Phe Ala Pro
1275                1280                1285

GAA GAC TAC TCC TCT TTC CAG CAC ATC AGG AAG GGC GGC TTC TGC GAC         1391
Glu Asp Tyr Ser Ser Phe Gln His Ile Arg Lys Gly Gly Phe Cys Asp
1290                1295                1300                1305

CAG TAC CTG GCG GTG CCG CAG CAC CCC TAC CAG TGG GCG AAG CCC AAG         1439
Gln Tyr Leu Ala Val Pro Gln His Pro Tyr Gln Trp Ala Lys Pro Lys
         1310                1315                1320

CCC CTG TCC CCT ACG TCC TAC ATG AGC CCG ACC CTG CCC GCC CTG GAC         1487
Pro Leu Ser Pro Thr Ser Tyr Met Ser Pro Thr Leu Pro Ala Leu Asp
              1325                1330                1335

TGG CAG CTG CCG TCC CAC TCA GGC CCG TAT GAG CTT CGG ATT GAG GTG         1535
Trp Gln Leu Pro Ser His Ser Gly Pro Tyr Glu Leu Arg Ile Glu Val
         1340                1345                1350

CAG CCC AAG TCC CAC CAC CGA GCC CAC TAC GAG ACG GAG GGC AGC CGG         1583
Gln Pro Lys Ser His His Arg Ala His Tyr Glu Thr Glu Gly Ser Arg
     1355                1360                1365

GGG GCC GTG AAG GCG TCG GCC GGA GGA CAC CCC ATC GTG CAG CTG CAT         1631
Gly Ala Val Lys Ala Ser Ala Gly Gly His Pro Ile Val Gln Leu His
1370                1375                1380                1385

GGC TAC TTG GAG AAT GAG CCG CTG ATG CTG CAG CTT TTC ATT GGG ACG         1679
Gly Tyr Leu Glu Asn Glu Pro Leu Met Leu Gln Leu Phe Ile Gly Thr
         1390                1395                1400

GCG GAC GAC CGC CTG CTG CGC CCG CAC GCC TTC TAC CAG GTG CAC CGC         1727
```

|  |  |  |  |  |  |  |  |  |  |  |  |  |  |  |  |
|---|---|---|---|---|---|---|---|---|---|---|---|---|---|---|---|
| Ala | Asp | Asp | Arg<br>1405 | Leu | Leu | Arg | Pro | His<br>1410 | Ala | Phe | Tyr | Gln | Val<br>1415 | His | Arg |

| ATC | ACA | GGG | AAG | ACC | GTG | TCC | ACC | ACC | AGC | CAC | GAG | GCT | ATC | CTC | TCC | 1775 |
|---|---|---|---|---|---|---|---|---|---|---|---|---|---|---|---|---|
| Ile | Thr | Gly<br>1420 | Lys | Thr | Val | Ser | Thr<br>1425 | Ser | His | Glu | Ala<br>1430 | Ile | Leu | Ser |  |  |

| AAC | ACC | AAA | GTC | CTG | GAG | ATC | CCA | CTC | CTG | CCG | GAG | AAC | AGC | ATG | CGA | 1823 |
|---|---|---|---|---|---|---|---|---|---|---|---|---|---|---|---|---|
| Asn | Thr<br>1435 | Lys | Val | Leu | Glu | Ile<br>1440 | Pro | Leu | Leu | Pro | Glu<br>1445 | Asn | Ser | Met | Arg |  |

| GCC | GTC | ATT | GAC | TGT | GCC | GGA | ATC | CTG | AAA | CTC | AGA | AAC | TCC | GAC | ATT | 1871 |
|---|---|---|---|---|---|---|---|---|---|---|---|---|---|---|---|---|
| Ala<br>1450 | Val | Ile | Asp | Cys | Ala<br>1455 | Gly | Ile | Leu | Lys<br>1460 | Leu | Arg | Asn | Ser | Asp<br>1465 | Ile |  |

| GAA | CTT | CGG | AAA | GGA | GAG | ACG | GAC | ATC | GGG | AGG | AAG | AAC | ACA | CGG | GTA | 1919 |
|---|---|---|---|---|---|---|---|---|---|---|---|---|---|---|---|---|
| Glu | Leu | Arg | Lys | Gly<br>1470 | Glu | Thr | Asp | Ile<br>1475 | Gly | Arg | Lys | Asn | Thr<br>1480 | Arg | Val |  |

| CGG | CTG | GTG | TTC | CGC | GTT | CAC | GTC | CCG | CAA | CCC | AGC | GGC | CGC | ACG | CTG | 1967 |
|---|---|---|---|---|---|---|---|---|---|---|---|---|---|---|---|---|
| Arg | Leu | Val | Phe<br>1485 | Arg | Val | His | Val | Pro<br>1490 | Gln | Pro | Ser | Gly | Arg<br>1495 | Thr | Leu |  |

| TCC | CTG | CAG | GTG | GCC | TCC | AAC | CCC | ATC | GAA | TGC | TCC | CAG | CGC | TCA | GCT | 2015 |
|---|---|---|---|---|---|---|---|---|---|---|---|---|---|---|---|---|
| Ser | Leu | Gln<br>1500 | Val | Ala | Ser | Asn | Pro<br>1505 | Ile | Glu | Cys | Ser | Gln<br>1510 | Arg | Ser | Ala |  |

| CAG | GAG | CTG | CCT | CTG | GTG | GAG | AAG | CAG | AGC | ACG | GAC | AGC | TAT | CCG | GTC | 2063 |
|---|---|---|---|---|---|---|---|---|---|---|---|---|---|---|---|---|
| Gln<br>1515 | Glu | Leu | Pro | Leu | Val<br>1520 | Glu | Lys | Gln | Ser | Thr<br>1525 | Asp | Ser | Tyr | Pro | Val |  |

| GTG | GGC | GGG | AAG | AAG | ATG | GTC | CTG | TCT | GGC | CAC | AAC | TTC | CTG | CAG | GAC | 2111 |
|---|---|---|---|---|---|---|---|---|---|---|---|---|---|---|---|---|
| Val<br>1530 | Gly | Gly | Lys | Lys | Met<br>1535 | Val | Leu | Ser | Gly | His<br>1540 | Asn | Phe | Leu | Gln | Asp<br>1545 |  |

| TCC | AAG | GTC | ATT | TTC | GTG | GAG | AAA | GCC | CCA | GAT | GGC | CAC | CAT | GTC | TGG | 2159 |
|---|---|---|---|---|---|---|---|---|---|---|---|---|---|---|---|---|
| Ser | Lys | Val | Ile | Phe<br>1550 | Val | Glu | Lys | Ala | Pro<br>1555 | Asp | Gly | His | His | Val<br>1560 | Trp |  |

| GAG | ATG | GAA | GCG | AAA | ACT | GAC | CGG | GAC | CTG | TGC | AAG | CCG | AAT | TCT | CTG | 2207 |
|---|---|---|---|---|---|---|---|---|---|---|---|---|---|---|---|---|
| Glu | Met | Glu | Ala<br>1565 | Lys | Thr | Asp | Arg | Asp<br>1570 | Leu | Cys | Lys | Pro | Asn<br>1575 | Ser | Leu |  |

| GTG | GTT | GAG | ATC | CCG | CCA | TTT | CGG | AAT | CAG | AGG | ATA | ACC | AGC | CCC | GTT | 2255 |
|---|---|---|---|---|---|---|---|---|---|---|---|---|---|---|---|---|
| Val | Val | Glu | Ile<br>1580 | Pro | Pro | Phe | Arg | Asn<br>1585 | Gln | Arg | Ile | Thr | Ser<br>1590 | Pro | Val |  |

| CAC | GTC | AGT | TTC | TAC | GTC | TGC | AAC | GGG | AAG | AGA | AAG | CGA | AGC | CAG | TAC | 2303 |
|---|---|---|---|---|---|---|---|---|---|---|---|---|---|---|---|---|
| His | Val | Ser<br>1595 | Phe | Tyr | Val | Cys | Asn<br>1600 | Gly | Lys | Arg | Lys | Arg<br>1605 | Ser | Gln | Tyr |  |

| CAG | CGT | TTC | ACC | TAC | CTT | CCC | GCC | AAC | GGT | AAC | GCC | ATC | TTT | CTA | ACC | 2351 |
|---|---|---|---|---|---|---|---|---|---|---|---|---|---|---|---|---|
| Gln<br>1610 | Arg | Phe | Thr | Tyr | Leu<br>1615 | Pro | Ala | Asn | Gly | Asn<br>1620 | Ala | Ile | Phe | Leu | Thr<br>1625 |  |

| GTA | AGC | CGT | GAA | CAT | GAG | CGC | GTG | GGG | TGC | TTT | TTC | TAA | AGACGCAGAA | | | 2400 |
|---|---|---|---|---|---|---|---|---|---|---|---|---|---|---|---|---|
| Val | Ser | Arg | Glu | His<br>1630 | Glu | Arg | Val | Gly | Cys<br>1635 | Phe | Phe | * |  |  |  |  |

| ACGACGTCGC | CGTAAAGCAG | CGTGGCGTGT | TGCACATTTA | ACTGTGTGAT | GTCCCGTTAG | 2460 |
|---|---|---|---|---|---|---|
| TGAGACCGAG | CCATCGATGC | CCTGAAAAGG | AAAGGAAAAG | GGAAGCTTCG | GATGCATTTT | 2520 |
| CCTTGATCCC | TGTTGGGGGT | GGGGGGCGGG | GGTTGCATAC | TCAGATAGTC | ACGGTTATTT | 2580 |
| TGCTTCTTGC | GAATGTATAA | CAGCCAAGGG | GAAAACATGG | CTCTTCTGCT | CCAAAAAACT | 2640 |
| GAGGGGGTCC | TGGTGTGCAT | TTGCACCCTA | AAGCTGCTTA | CGGTGAAAAG | GCAAATAGGT | 2700 |
| ATAGCTATTT | TGCAGGCACC | TTTAGGAATA | AACTTTGCTT | TTA |  | 2743 |

( 2 ) INFORMATION FOR SEQ ID NO:4:

( i ) SEQUENCE CHARACTERISTICS:
        ( A ) LENGTH: 716 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Pro | Ser | Thr | Ser | Phe | Pro | Val | Pro | Ser | Lys | Phe | Pro | Leu | Gly | Pro |
| 1 | | | | 5 | | | | | 10 | | | | | 15 | |

| Ala | Ala | Ala | Val | Phe | Gly | Arg | Gly | Glu | Thr | Leu | Gly | Pro | Ala | Pro | Arg |
| | | | 20 | | | | | 25 | | | | | 30 | | |

| Ala | Gly | Gly | Thr | Met | Lys | Ser | Ala | Glu | Glu | His | Tyr | Gly | Tyr | Ala |
| | | 35 | | | | | 40 | | | | 45 | | | |

| Ser | Ser | Asn | Val | Ser | Pro | Ala | Leu | Pro | Leu | Pro | Thr | Ala | His | Ser | Thr |
| | | 50 | | | | 55 | | | | | 60 | | | | |

| Leu | Pro | Ala | Pro | Cys | His | Asn | Leu | Gln | Thr | Ser | Thr | Pro | Gly | Ile | Ile |
| 65 | | | | | 70 | | | | | 75 | | | | | 80 |

| Pro | Pro | Ala | Asp | His | Pro | Ser | Gly | Tyr | Gly | Ala | Ala | Leu | Asp | Gly | Gly |
| | | | | 85 | | | | | 90 | | | | | 95 | |

| Pro | Ala | Gly | Tyr | Phe | Leu | Ser | Ser | Gly | His | Thr | Arg | Pro | Asp | Gly | Ala |
| | | | 100 | | | | | 105 | | | | | 110 | | |

| Pro | Ala | Leu | Glu | Ser | Pro | Arg | Ile | Glu | Ile | Thr | Ser | Cys | Leu | Gly | Leu |
| | | | 115 | | | | 120 | | | | | 125 | | | |

| Tyr | His | Asn | Asn | Asn | Gln | Phe | Phe | His | Asp | Val | Glu | Val | Glu | Asp | Val |
| | 130 | | | | | 135 | | | | | 140 | | | | |

| Leu | Pro | Ser | Ser | Lys | Arg | Ser | Pro | Ser | Thr | Ala | Thr | Leu | Ser | Leu | Pro |
| 145 | | | | | 150 | | | | | 155 | | | | | 160 |

| Ser | Leu | Glu | Ala | Tyr | Arg | Asp | Pro | Ser | Cys | Leu | Ser | Pro | Ala | Ser | Ser |
| | | | | 165 | | | | | 170 | | | | | 175 | |

| Leu | Ser | Ser | Arg | Ser | Cys | Asn | Ser | Glu | Ala | Ser | Ser | Tyr | Glu | Ser | Asn |
| | | | 180 | | | | | 185 | | | | | 190 | | |

| Tyr | Ser | Tyr | Pro | Tyr | Ala | Ser | Pro | Gln | Thr | Ser | Pro | Trp | Gln | Ser | Pro |
| | | 195 | | | | | 200 | | | | | 205 | | | |

| Cys | Val | Ser | Pro | Lys | Thr | Thr | Asp | Pro | Glu | Glu | Gly | Phe | Pro | Arg | Gly |
| | 210 | | | | | 215 | | | | | 220 | | | | |

| Leu | Gly | Ala | Cys | Thr | Leu | Leu | Gly | Ser | Pro | Gln | His | Ser | Pro | Ser | Thr |
| 225 | | | | | 230 | | | | | 235 | | | | | 240 |

| Ser | Pro | Arg | Ala | Ser | Val | Thr | Glu | Glu | Ser | Trp | Leu | Gly | Ala | Arg | Ser |
| | | | | 245 | | | | | 250 | | | | | 255 | |

| Ser | Arg | Pro | Ala | Ser | Pro | Cys | Asn | Lys | Arg | Lys | Tyr | Ser | Leu | Asn | Gly |
| | | | 260 | | | | | 265 | | | | | 270 | | |

| Arg | Gln | Pro | Pro | Tyr | Ser | Pro | His | His | Ser | Pro | Thr | Pro | Ser | Pro | His |
| | | 275 | | | | | 280 | | | | | 285 | | | |

| Gly | Ser | Pro | Arg | Val | Ser | Val | Thr | Asp | Asp | Ser | Trp | Leu | Gly | Asn | Thr |
| | 290 | | | | | 295 | | | | | 300 | | | | |

| Thr | Gln | Tyr | Thr | Ser | Ser | Ala | Ile | Val | Ala | Ala | Ile | Asn | Ala | Leu | Thr |
| 305 | | | | | 310 | | | | | 315 | | | | | 320 |

| Thr | Asp | Ser | Ser | Leu | Asp | Leu | Gly | Asp | Gly | Val | Pro | Val | Lys | Ser | Arg |
| | | | | 325 | | | | | 330 | | | | | 335 | |

| Lys | Thr | Thr | Leu | Glu | Gln | Pro | Pro | Ser | Val | Ala | Leu | Lys | Val | Glu | Pro |
| | | | 340 | | | | | 345 | | | | | 350 | | |

| Val | Gly | Glu | Asp | Leu | Gly | Ser | Pro | Pro | Pro | Ala | Asp | Phe | Ala | Pro |
| | | 355 | | | | | 360 | | | | | 365 | | | |

| Glu | Asp | Tyr | Ser | Ser | Phe | Gln | His | Ile | Arg | Lys | Gly | Gly | Phe | Cys | Asp |
| | 370 | | | | | 375 | | | | | 380 | | | | |

| Gln | Tyr | Leu | Ala | Val | Pro | Gln | His | Pro | Tyr | Gln | Trp | Ala | Lys | Pro | Lys |
| 385 | | | | | 390 | | | | | 395 | | | | | 400 |

| Pro | Leu | Ser | Pro | Thr | Ser | Tyr | Met | Ser | Pro | Thr | Leu | Pro | Ala | Leu | Asp |
| | | | | 405 | | | | | 410 | | | | | 415 | |

| | | | | | | | | | | | | | |
|---|---|---|---|---|---|---|---|---|---|---|---|---|---|
|Trp|Gln|Leu|Pro 420|Ser|His|Ser|Gly|Pro 425|Tyr|Glu|Leu|Arg|Ile 430|Glu|Val|
|Gln|Pro|Lys 435|Ser|His|His|Arg|Ala 440|His|Tyr|Glu|Thr|Glu 445|Gly|Ser|Arg|
|Gly|Ala 450|Val|Lys|Ala|Ser|Ala 455|Gly|Gly|His|Pro|Ile 460|Val|Gln|Leu|His|
|Gly 465|Tyr|Leu|Glu|Asn|Glu 470|Pro|Leu|Met|Leu|Gln 475|Leu|Phe|Ile|Gly|Thr 480|
|Ala|Asp|Asp|Arg|Leu 485|Leu|Arg|Pro|His|Ala 490|Phe|Tyr|Gln|Val|His 495|Arg|
|Ile|Thr|Gly|Lys 500|Thr|Val|Ser|Thr|Thr 505|Ser|His|Glu|Ala|Ile 510|Leu|Ser|
|Asn|Thr|Lys 515|Val|Leu|Glu|Ile|Pro 520|Leu|Leu|Pro|Glu|Asn 525|Ser|Met|Arg|
|Ala|Val 530|Ile|Asp|Cys|Ala|Gly 535|Ile|Leu|Lys|Leu|Arg 540|Asn|Ser|Asp|Ile|
|Glu 545|Leu|Arg|Lys|Gly|Glu 550|Thr|Asp|Ile|Gly|Arg 555|Lys|Asn|Thr|Arg|Val 560|
|Arg|Leu|Val|Phe|Arg 565|Val|His|Val|Pro|Gln 570|Pro|Ser|Gly|Arg|Thr 575|Leu|
|Ser|Leu|Gln|Val 580|Ala|Ser|Asn|Pro|Ile 585|Glu|Cys|Ser|Gln|Arg 590|Ser|Ala|
|Gln|Glu|Leu 595|Pro|Leu|Val|Glu|Lys 600|Gln|Ser|Thr|Asp|Ser 605|Tyr|Pro|Val|
|Val|Gly 610|Gly|Lys|Lys|Met|Val 615|Leu|Ser|Gly|His|Asn 620|Phe|Leu|Gln|Asp|
|Ser 625|Lys|Val|Ile|Phe|Val 630|Glu|Lys|Ala|Pro|Asp 635|Gly|His|His|Val|Trp 640|
|Glu|Met|Glu|Ala|Lys 645|Thr|Asp|Arg|Asp|Leu 650|Cys|Lys|Pro|Asn|Ser 655|Leu|
|Val|Val|Glu|Ile 660|Pro|Pro|Phe|Arg|Asn 665|Gln|Arg|Ile|Thr|Ser 670|Pro|Val|
|His|Val|Ser 675|Phe|Tyr|Val|Cys|Asn 680|Gly|Lys|Arg|Lys|Arg 685|Ser|Gln|Tyr|
|Gln|Arg|Phe 690|Thr|Tyr|Leu|Pro 695|Ala|Asn|Gly|Asn|Ala 700|Ile|Phe|Leu|Thr|
|Val 705|Ser|Arg|Glu|His|Glu 710|Arg|Val|Gly|Cys|Phe 715|Phe|

(2) INFORMATION FOR SEQ ID NO:5:

(i) SEQUENCE CHARACTERISTICS:
        (A) LENGTH: 2881 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 142..2850

(xi) SEQUENCE DESCRIPTION: SEQ ID NO:5:

```
GCTTCTGGAG  GGAGGCGGCA  GCGACGGAGG  AGGGGGCTTC  TCAGAGAAAG  GGAGGGAGGG      60

AGCCACCCGG  GTGAAGATAC  AGCAGCCTCC  TGAACTCCCC  CCTCCCACCC  AGGCCGGGAC     120

CTGGGGGCTC  CTGCCGGATC  C ATG GGG  GCG GCC  AGC TGC GAG GAT GAG GAG        171
```

-continued

|     |     |     |     |     | Met<br>720 | Gly | Ala | Ala | Ser | Cys | Glu<br>725 | Asp | Glu | Glu |     |
|---|---|---|---|---|---|---|---|---|---|---|---|---|---|---|---|
| CTG | GAA | TTT | AAG | CTG | GTG | TTC | GGG | GAG | GAA | AAG | GAG | GCC | CCC | CCG | CTG | 219 |
| Leu | Glu<br>730 | Phe | Lys | Leu | Val | Phe | Gly<br>735 | Glu | Glu | Lys | Glu | Ala<br>740 | Pro | Pro | Leu |

| GGC | GCG | GGG | GGA | TTG | GGG | GAA | GAA | CTG | GAC | TCA | GAG | GAT | GCC | CCG | CCA | 267 |
| Gly | Ala<br>745 | Gly | Gly | Leu | Gly<br>750 | Glu | Glu | Leu | Asp | Ser<br>755 | Glu | Asp | Ala | Pro | Pro |

| TGC | TGC | CGT | CTG | GCC | TTG | GGA | GAG | CCC | CCT | CCC | TAT | GGC | GCT | GCA | CCT | 315 |
| Cys<br>760 | Cys | Arg | Leu | Ala | Leu<br>765 | Gly | Glu | Pro | Pro | Pro<br>770 | Tyr | Gly | Ala | Ala | Pro<br>775 |

| ATC | GGT | ATT | CCC | CGA | CCT | CCA | CCC | CCT | CGG | CCT | GGC | ATG | CAT | TCG | CCA | 363 |
| Ile | Gly | Ile | Pro | Arg<br>780 | Pro | Pro | Pro | Pro | Arg<br>785 | Pro | Gly | Met | His | Ser<br>790 | Pro |

| CCG | CCG | CGA | CCA | GCC | CCC | TCA | CCT | GGC | ACC | TGG | GAG | AGC | CAG | CCC | GCC | 411 |
| Pro | Pro | Arg<br>795 | Pro | Ala | Pro | Ser | Pro<br>800 | Gly | Thr | Trp | Glu | Ser | Gln<br>805 | Pro | Ala |

| AGG | TCG | GTG | AGG | CTG | GGA | GGA | CCA | GGA | GGG | GGT | GCT | GGG | GGT | GCT | GGG | 459 |
| Arg | Ser | Val | Arg<br>810 | Leu | Gly | Gly | Pro | Gly<br>815 | Gly | Gly | Ala | Gly<br>820 | Gly | Ala | Gly |

| GGT | GGC | CGT | GTT | CTC | GAG | TGT | CCC | AGC | ATC | CGC | ATC | ACC | TCC | ATC | TCT | 507 |
| Gly | Gly | Arg | Val<br>825 | Leu | Glu | Cys | Pro<br>830 | Ser | Ile | Arg | Ile | Thr<br>835 | Ser | Ile | Ser |

| CCC | ACG | CCG | GAG | CCG | CCA | GCA | GCG | CTG | GAG | GAC | AAC | CCT | GAT | GCC | TGG | 555 |
| Pro | Thr | Pro | Glu | Pro<br>840 | Pro | Ala | Ala | Leu<br>845 | Glu | Asp | Asn | Pro | Asp<br>850 | Ala | Trp<br>855 |

| GGG | GAC | GGC | TCT | CCT | AGA | GAT | TAC | CCC | CCA | CCA | GAA | GGC | TTT | GGG | GGC | 603 |
| Gly | Asp | Gly | Ser | Pro | Arg<br>860 | Asp | Tyr | Pro | Pro | Pro<br>865 | Glu | Gly | Phe | Gly<br>870 | Gly |

| TAC | AGA | GAA | GCA | GGG | GCC | CAG | GGT | GGG | GGG | GCC | TTC | TTC | AGC | CCA | AGC | 651 |
| Tyr | Arg | Glu | Ala<br>875 | Gly | Ala | Gln | Gly | Gly<br>880 | Gly | Ala | Phe | Phe | Ser<br>885 | Pro | Ser |

| CCT | GGC | AGC | AGC | AGC | CTG | TCC | TCG | TGG | AGC | TTC | TTC | TCC | GAT | GCC | TCT | 699 |
| Pro | Gly | Ser<br>890 | Ser | Ser | Leu | Ser | Ser<br>895 | Trp | Ser | Phe | Phe | Ser<br>900 | Asp | Ala | Ser |

| GAC | GAG | GCA | GCC | CTG | TAT | GCA | GCC | TGC | GAC | GAG | GTG | GAG | TCT | GAG | CTA | 747 |
| Asp | Glu | Ala | Ala<br>905 | Leu | Tyr | Ala | Ala<br>910 | Cys | Asp | Glu | Val | Glu<br>915 | Ser | Glu | Leu |

| AAT | GAG | GCG | GCC | TCC | CGC | TTT | GGC | CTG | GGC | TCC | CCG | CTG | CCC | TCG | CCC | 795 |
| Asn | Glu<br>920 | Ala | Ala | Ser | Arg<br>925 | Phe | Gly | Leu | Gly | Ser<br>930 | Pro | Leu | Pro | Ser<br>935 | Pro |

| CGG | GCC | TCC | CCT | CGG | CCA | TGG | ACC | CCC | GAA | GAT | CCC | TGG | AGC | CTG | TAT | 843 |
| Arg | Ala | Ser | Pro | Arg<br>940 | Pro | Trp | Thr | Pro | Glu<br>945 | Asp | Pro | Trp | Ser | Leu<br>950 | Tyr |

| GGT | CCA | AGC | CCC | GGA | GGC | CGA | GGG | CCA | GAG | GAT | AGC | TGG | CTA | CTC | CTC | 891 |
| Gly | Pro | Ser<br>955 | Pro | Gly | Gly | Arg | Gly<br>960 | Pro | Glu | Asp | Ser | Trp<br>965 | Leu | Leu | Leu |

| AGT | GCT | CCT | GGG | CCC | ACC | CCA | GCC | TCC | CCG | CGG | CCT | GCC | TCT | CCA | TGT | 939 |
| Ser | Ala | Pro | Gly<br>970 | Pro | Thr | Pro | Ala<br>975 | Ser | Pro | Arg | Pro | Ala<br>980 | Ser | Pro | Cys |

| GGC | AAG | CGG | CGC | TAT | TCC | AGC | TCG | GGA | ACC | CCA | TCT | TCA | GCC | TCC | CCA | 987 |
| Gly | Lys | Arg<br>985 | Arg | Tyr | Ser | Ser<br>990 | Ser | Gly | Thr | Pro | Ser<br>995 | Ser | Ala | Ser | Pro |

| GCT | CTG | TCC | CGC | CGT | GGC | AGC | CTG | GGG | GAA | GAG | GGG | TCT | GAG | CCA | CCT | 1035 |
| Ala | Leu<br>1000 | Ser | Arg | Arg | Gly<br>1005 | Ser | Leu | Gly | Glu | Glu<br>1010 | Gly | Ser | Glu | Pro<br>1015 | Pro |

| CCA | CCA | CCC | CCA | TTG | CCT | CTG | GCC | CGG | GAC | CCG | GGC | TCC | CCT | GGT | CCC | 1083 |
| Pro | Pro | Pro | Pro | Leu<br>1020 | Pro | Leu | Ala | Arg | Asp<br>1025 | Pro | Gly | Ser | Pro<br>1030 | Gly | Pro |

| TTT | GAC | TAT | GTG | GGG | GCC | CCA | CCA | GCT | GAG | AGC | ATC | CCT | CAG | AAG | ACA | 1131 |

-continued

```
                Phe Asp Tyr Val Gly Ala Pro Pro Ala Glu Ser Ile Pro Gln Lys Thr
                        1035                1040                1045

CGG CGG ACT TCC AGC GAG CAG GCA GTG GCT CTG CCT CGG TCT GAG GAG              1179
Arg Arg Thr Ser Ser Glu Gln Ala Val Ala Leu Pro Arg Ser Glu Glu
        1050                1055                1060

CCT GCC TCA TGC AAT GGG AAG CTG CCC TTG GGA GCA GAG GAG TCT GTG              1227
Pro Ala Ser Cys Asn Gly Lys Leu Pro Leu Gly Ala Glu Glu Ser Val
1065            1070                1075

GCT CCT CCA GGA GGT TCC CGG AAG GAG GTG GCT GGC ATG GAC TAC CTG              1275
Ala Pro Pro Gly Gly Ser Arg Lys Glu Val Ala Gly Met Asp Tyr Leu
1080            1085                1090                1095

GCA GTG CCC TCC CCA CTC GCT TGG TCC AAG GCC CGG ATT GGG GGA CAC              1323
Ala Val Pro Ser Pro Leu Ala Trp Ser Lys Ala Arg Ile Gly Gly His
                1100                1105                1110

AGC CCT ATC TTC AGG ACC TCT GCC CTA CCC CCA CTG GAC TGG CCT CTG              1371
Ser Pro Ile Phe Arg Thr Ser Ala Leu Pro Pro Leu Asp Trp Pro Leu
            1115                1120                1125

CCC AGC CAA TAT GAG CAG CTG GAG CTG AGG ATC GAG GTA CAG CCT AGA              1419
Pro Ser Gln Tyr Glu Gln Leu Glu Leu Arg Ile Glu Val Gln Pro Arg
        1130                1135                1140

GCC CAC CAC CGG GCC CAC TAT GAG ACA GAA GGC AGC CGT GGA GCT GTC              1467
Ala His His Arg Ala His Tyr Glu Thr Glu Gly Ser Arg Gly Ala Val
    1145                1150                1155

AAA GCT GCC CCT GGC GGT CAC CCC GTA GTC AAG CTC CTA GGC TAC AGT              1515
Lys Ala Ala Pro Gly Gly His Pro Val Val Lys Leu Leu Gly Tyr Ser
1160                1165                1170                1175

GAG AAG CCA CTG ACC CTA CAG ATG TTC ATC GGC ACT GCA GAT GAA AGG              1563
Glu Lys Pro Leu Thr Leu Gln Met Phe Ile Gly Thr Ala Asp Glu Arg
                1180                1185                1190

AAC CTG CGG CCT CAT GCC TTC TAT CAG GTG CAC CGT ATC ACA GGC AAG              1611
Asn Leu Arg Pro His Ala Phe Tyr Gln Val His Arg Ile Thr Gly Lys
            1195                1200                1205

ATG GTG GCC ACG GCC AGC TAT GAA GCC GTA GTC AGT GGC ACC AAG GTG              1659
Met Val Ala Thr Ala Ser Tyr Glu Ala Val Val Ser Gly Thr Lys Val
        1210                1215                1220

TTG GAG ATG ACT CTG CTG CCT GAG AAC AAC ATG GCG GCC AAC ATT GAC              1707
Leu Glu Met Thr Leu Leu Pro Glu Asn Asn Met Ala Ala Asn Ile Asp
    1225                1230                1235

TGC GCG GGA ATC CTG AAG CTT CGG AAT TCA GAC ATT GAG CTT CGG AAG              1755
Cys Ala Gly Ile Leu Lys Leu Arg Asn Ser Asp Ile Glu Leu Arg Lys
1240                1245                1250                1255

GGT GAG ACG GAC ATC GGG CGC AAA AAC ACA CGT GTA CGG CTG GTG TTC              1803
Gly Glu Thr Asp Ile Gly Arg Lys Asn Thr Arg Val Arg Leu Val Phe
                1260                1265                1270

CGG GTA CAC GTG CCC CAG GGC GGC GGG AAG GTC GTC TCA GTA CAG GCA              1851
Arg Val His Val Pro Gln Gly Gly Gly Lys Val Val Ser Val Gln Ala
            1275                1280                1285

GCA TCG GTG CCC ATC GAG TGC TCC CAG CGC TCA GCC CAG GAG CTG CCC              1899
Ala Ser Val Pro Ile Glu Cys Ser Gln Arg Ser Ala Gln Glu Leu Pro
        1290                1295                1300

CAG GTG GAG GCC TAC AGC CCC AGT GCC TGC TCT GTG AGA GGA GGC GAG              1947
Gln Val Glu Ala Tyr Ser Pro Ser Ala Cys Ser Val Arg Gly Gly Glu
    1305                1310                1315

GAA CTG GTA CTG ACC GGC TCC AAC TTC CTG CCA GAC TCC AAG GTG GTG              1995
Glu Leu Val Leu Thr Gly Ser Asn Phe Leu Pro Asp Ser Lys Val Val
1320                1325                1330                1335

TTC ATT GAG AGG GGT CCT GAT GGG AAG CTG CAA TGG GAG GAG GAG GCC              2043
Phe Ile Glu Arg Gly Pro Asp Gly Lys Leu Gln Trp Glu Glu Glu Ala
                1340                1345                1350

ACA GTG AAC CGA CTG CAG AGC AAC GAG GTG ACG CTG ACC CTG ACT GTC              2091
```

```
        Thr Val Asn Arg Leu Gln Ser Asn Glu Val Thr Leu Thr Leu Thr Val
                        1355                1360                1365

CCC GAG TAC AGC AAC AAG AGG GTT TCC CGG CCA GTC CAG GTC TAC TTT          2139
Pro Glu Tyr Ser Asn Lys Arg Val Ser Arg Pro Val Gln Val Tyr Phe
        1370                1375                1380

TAT GTC TCC AAT GGG CGG AGG AAA CGC AGT CCT ACC CAG AGT TTC AGG          2187
Tyr Val Ser Asn Gly Arg Arg Lys Arg Ser Pro Thr Gln Ser Phe Arg
        1385                1390                1395

TTT CTG CCT GTG ATC TGC AAA GAG GAG CCC CTA CCG GAC TCA TCT CTG          2235
Phe Leu Pro Val Ile Cys Lys Glu Glu Pro Leu Pro Asp Ser Ser Leu
1400                1405                1410                    1415

CGG GGT TTC CCT TCA GCA TCG GCA ACC CCC TTT GGC ACT GAC ATG GAC          2283
Arg Gly Phe Pro Ser Ala Ser Ala Thr Pro Phe Gly Thr Asp Met Asp
                1420                1425                1430

TTC TCA CCA CCC AGG CCC CCC TAC CCC TCC TAT CCC CAT GAA GAC CCT          2331
Phe Ser Pro Pro Arg Pro Pro Tyr Pro Ser Tyr Pro His Glu Asp Pro
        1435                1440                1445

GCT TGC GAA ACT CCT TAC CTA TCA GAA GGC TTC GGC TAT GGC ATG CCC          2379
Ala Cys Glu Thr Pro Tyr Leu Ser Glu Gly Phe Gly Tyr Gly Met Pro
        1450                1455                1460

CCT CTG TAC CCC CAG ACG GGG CCC CCA CCA TCC TAC AGA CCG GGC CTG          2427
Pro Leu Tyr Pro Gln Thr Gly Pro Pro Pro Ser Tyr Arg Pro Gly Leu
        1465                1470                1475

CGG ATG TTC CCT GAG ACT AGG GGT ACC ACA GGT TGT GCC CAA CCA CCT          2475
Arg Met Phe Pro Glu Thr Arg Gly Thr Thr Gly Cys Ala Gln Pro Pro
1480                1485                1490                    1495

GCA GTT TCC TTC CTT CCC CGC CCC TTC CCT AGT GAC CCG TAT GGA GGG          2523
Ala Val Ser Phe Leu Pro Arg Pro Phe Pro Ser Asp Pro Tyr Gly Gly
                1500                1505                1510

CGG GGC TCC TCT TTC CCC CTG GGG CTG CCA TTC TCT CCG CCA GCC CCC          2571
Arg Gly Ser Ser Phe Pro Leu Gly Leu Pro Phe Ser Pro Pro Ala Pro
        1515                1520                1525

TTT CGG CCG CCT CCT CTT CCT GCA TCC CCA CCG CTT GAA GGC CCC TTC          2619
Phe Arg Pro Pro Pro Leu Pro Ala Ser Pro Pro Leu Glu Gly Pro Phe
        1530                1535                1540

CCT TCC CAG AGT GAT GTG CAT CCC CTA CCT GCT GAG GGA TAC AAT AAG          2667
Pro Ser Gln Ser Asp Val His Pro Leu Pro Ala Glu Gly Tyr Asn Lys
        1545                1550                1555

GTA GGG CCA GGC TAT GGC CCT GGG GAG GGG GCT CCG GAG CAG GAG AAA          2715
Val Gly Pro Gly Tyr Gly Pro Gly Glu Gly Ala Pro Glu Gln Glu Lys
1560                1565                1570                    1575

TCC AGG GGT GGC TAC AGC AGC GGC TTT CGA GAC AGT GTC CCT ATC CAG          2763
Ser Arg Gly Gly Tyr Ser Ser Gly Phe Arg Asp Ser Val Pro Ile Gln
                1580                1585                1590

GGT ATC ACG CTG GAG GAA GTG AGT GAG ATC ATT GGC CGA GAC CTG AGT          2811
Gly Ile Thr Leu Glu Glu Val Ser Glu Ile Ile Gly Arg Asp Leu Ser
        1595                1600                1605

GGC TTC CCT GCA CCT CCT GGA GAA GAG CCT CCT GCC TGA ACCACGTGAA           2860
Gly Phe Pro Ala Pro Pro Gly Glu Glu Pro Pro Ala  *
        1610                1615                1620

CTGTCATCAC CTGGCAACCC C                                                  2881
```

( 2 ) INFORMATION FOR SEQ ID NO:6:

( i ) SEQUENCE CHARACTERISTICS:
        ( A ) LENGTH: 902 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Gly Ala Ala Ser Cys Glu Asp Glu Glu Leu Glu Phe Lys Leu Val
 1               5                  10                  15
Phe Gly Glu Glu Lys Glu Ala Pro Pro Leu Gly Ala Gly Gly Leu Gly
             20                  25                  30
Glu Glu Leu Asp Ser Glu Asp Ala Pro Pro Cys Cys Arg Leu Ala Leu
             35                  40                  45
Gly Glu Pro Pro Pro Tyr Gly Ala Ala Pro Ile Gly Ile Pro Arg Pro
         50                  55                  60
Pro Pro Pro Arg Pro Gly Met His Ser Pro Pro Arg Pro Ala Pro
 65                  70                  75                  80
Ser Pro Gly Thr Trp Glu Ser Gln Pro Ala Arg Ser Val Arg Leu Gly
                 85                  90                      95
Gly Pro Gly Gly Gly Ala Gly Gly Ala Gly Gly Gly Arg Val Leu Glu
             100                 105                 110
Cys Pro Ser Ile Arg Ile Thr Ser Ile Ser Pro Thr Pro Glu Pro Pro
             115                 120                 125
Ala Ala Leu Glu Asp Asn Pro Asp Ala Trp Gly Asp Gly Ser Pro Arg
     130                 135                 140
Asp Tyr Pro Pro Pro Glu Gly Phe Gly Gly Tyr Arg Glu Ala Gly Ala
 145                 150                 155                 160
Gln Gly Gly Gly Ala Phe Phe Ser Pro Ser Pro Gly Ser Ser Ser Leu
             165                 170                 175
Ser Ser Trp Ser Phe Phe Ser Asp Ala Ser Asp Glu Ala Ala Leu Tyr
             180                 185                 190
Ala Ala Cys Asp Glu Val Glu Ser Glu Leu Asn Glu Ala Ala Ser Arg
             195                 200                 205
Phe Gly Leu Gly Ser Pro Leu Pro Ser Pro Arg Ala Ser Pro Arg Pro
     210                 215                 220
Trp Thr Pro Glu Asp Pro Trp Ser Leu Tyr Gly Pro Ser Pro Gly Gly
 225                 230                 235                 240
Arg Gly Pro Glu Asp Ser Trp Leu Leu Leu Ser Ala Pro Gly Pro Thr
             245                 250                 255
Pro Ala Ser Pro Arg Pro Ala Ser Pro Cys Gly Lys Arg Arg Tyr Ser
             260                 265                 270
Ser Ser Gly Thr Pro Ser Ser Ala Ser Pro Ala Leu Ser Arg Arg Gly
             275                 280                 285
Ser Leu Gly Glu Glu Gly Ser Glu Pro Pro Pro Pro Pro Leu Pro
     290                 295                 300
Leu Ala Arg Asp Pro Gly Ser Pro Gly Pro Phe Asp Tyr Val Gly Ala
 305                 310                 315                 320
Pro Pro Ala Glu Ser Ile Pro Gln Lys Thr Arg Arg Thr Ser Ser Glu
             325                 330                 335
Gln Ala Val Ala Leu Pro Arg Ser Glu Glu Pro Ala Ser Cys Asn Gly
             340                 345                 350
Lys Leu Pro Leu Gly Ala Glu Glu Ser Val Ala Pro Pro Gly Gly Ser
             355                 360                 365
Arg Lys Glu Val Ala Gly Met Asp Tyr Leu Ala Val Pro Ser Pro Leu
 370                 375                 380
Ala Trp Ser Lys Ala Arg Ile Gly Gly His Ser Pro Ile Phe Arg Thr
 385                 390                 395                 400
Ser Ala Leu Pro Pro Leu Asp Trp Pro Leu Pro Ser Gln Tyr Glu Gln
             405                 410                 415
Leu Glu Leu Arg Ile Glu Val Gln Pro Arg Ala His His Arg Ala His
```

```
                              420                      425                         430
Tyr Glu Thr Glu Gly Ser Arg Gly Ala Val Lys Ala Ala Pro Gly Gly
            435                 440                 445
His Pro Val Val Lys Leu Leu Gly Tyr Ser Glu Lys Pro Leu Thr Leu
450                         455                 460
Gln Met Phe Ile Gly Thr Ala Asp Glu Arg Asn Leu Arg Pro His Ala
465                 470                     475                         480
Phe Tyr Gln Val His Arg Ile Thr Gly Lys Met Val Ala Thr Ala Ser
                485                     490                     495
Tyr Glu Ala Val Val Ser Gly Thr Lys Val Leu Glu Met Thr Leu Leu
                500                 505                 510
Pro Glu Asn Asn Met Ala Ala Asn Ile Asp Cys Ala Gly Ile Leu Lys
            515                 520                 525
Leu Arg Asn Ser Asp Ile Glu Leu Arg Lys Gly Glu Thr Asp Ile Gly
530                     535                     540
Arg Lys Asn Thr Arg Val Arg Leu Val Phe Arg Val His Val Pro Gln
545                 550                     555                         560
Gly Gly Gly Lys Val Val Ser Val Gln Ala Ala Ser Val Pro Ile Glu
                565                 570                 575
Cys Ser Gln Arg Ser Ala Gln Glu Leu Pro Gln Val Glu Ala Tyr Ser
            580                 585                 590
Pro Ser Ala Cys Ser Val Arg Gly Gly Glu Glu Leu Val Leu Thr Gly
        595                 600                 605
Ser Asn Phe Leu Pro Asp Ser Lys Val Val Phe Ile Glu Arg Gly Pro
        610                 615                 620
Asp Gly Lys Leu Gln Trp Glu Glu Glu Ala Thr Val Asn Arg Leu Gln
625                     630                 635                     640
Ser Asn Glu Val Thr Leu Thr Leu Thr Val Pro Glu Tyr Ser Asn Lys
                645                 650                 655
Arg Val Ser Arg Pro Val Gln Val Tyr Phe Tyr Val Ser Asn Gly Arg
            660                 665                 670
Arg Lys Arg Ser Pro Thr Gln Ser Phe Arg Phe Leu Pro Val Ile Cys
        675                 680                 685
Lys Glu Glu Pro Leu Pro Asp Ser Ser Leu Arg Gly Phe Pro Ser Ala
690                 695                 700
Ser Ala Thr Pro Phe Gly Thr Asp Met Asp Phe Ser Pro Pro Arg Pro
705                 710                 715                     720
Pro Tyr Pro Ser Tyr Pro His Glu Asp Pro Ala Cys Glu Thr Pro Tyr
                725                 730                 735
Leu Ser Glu Gly Phe Gly Tyr Gly Met Pro Pro Leu Tyr Pro Gln Thr
            740                 745                 750
Gly Pro Pro Pro Ser Tyr Arg Pro Gly Leu Arg Met Phe Pro Glu Thr
        755                 760                 765
Arg Gly Thr Thr Gly Cys Ala Gln Pro Pro Ala Val Ser Phe Leu Pro
    770                 775                 780
Arg Pro Phe Pro Ser Asp Pro Tyr Gly Gly Arg Gly Ser Ser Phe Pro
785                 790                 795                     800
Leu Gly Leu Pro Phe Ser Pro Pro Ala Pro Phe Arg Pro Pro Pro Leu
            805                 810                 815
Pro Ala Ser Pro Pro Leu Glu Gly Pro Phe Pro Ser Gln Ser Asp Val
        820                 825                 830
His Pro Leu Pro Ala Glu Gly Tyr Asn Lys Val Gly Pro Gly Tyr Gly
    835                 840                 845
```

| | | | | | | | | | | | | | | |
|---|---|---|---|---|---|---|---|---|---|---|---|---|---|---|
| Pro | Gly | Glu | Gly | Ala | Pro | Glu | Gln | Glu | Lys | Ser | Arg | Gly | Gly | Tyr | Ser |
| | 850 | | | | 855 | | | | 860 | | | | | |
| Ser | Gly | Phe | Arg | Asp | Ser | Val | Pro | Ile | Gln | Gly | Ile | Thr | Leu | Glu | Glu |
| 865 | | | | | 870 | | | | 875 | | | | | 880 |
| Val | Ser | Glu | Ile | Ile | Gly | Arg | Asp | Leu | Ser | Gly | Phe | Pro | Ala | Pro | Pro |
| | | | | 885 | | | | | 890 | | | | | 895 | |
| Gly | Glu | Glu | Pro | Pro | Ala | | | | | | | | | | |
| | | | 900 | | | | | | | | | | | | |

( 2 ) INFORMATION FOR SEQ ID NO:7:

( i ) SEQUENCE CHARACTERISTICS:
( A ) LENGTH: 2406 base pairs
( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 211..2337

( x i ) SEQUENCE DESCRIPTION: SEQ ID NO:7:

```
CGGCTGCGGT  TCCTGGTGCT  GCTCGGCGCG  CGGCCAGCTT  TCGGAACGGA  ACGCTCGGCG      60

TCGCGGGCCC  CGCCCGGAAA  GTTTGCCGTG  GAGTCGCGAC  CTCTTGGCCC  GCGCGGCCCG     120

GCATGAAGCG  GCGTTGAGGA  GCTGCTGCCG  CCGCTTGCCG  CTGCCGCCGC  CGCCGCCTGA     180

GGAGGAGCTG  CAGCACCCTG  GGCCACGCCG  ATG  ACT  ACT  GCA  AAC  TGT  GGC  GCC   234
                                    Met  Thr  Thr  Ala  Asn  Cys  Gly  Ala
                                     905                           910
```

| CAC | GAC | GAG | CTC | GAC | TTC | AAA | CTC | GTC | TTT | GGC | GAG | GAC | GGG | GCG | CCG | 282 |
|---|---|---|---|---|---|---|---|---|---|---|---|---|---|---|---|---|
| His | Asp | Glu | Leu | Asp | Phe | Lys | Leu | Val | Phe | Gly | Glu | Asp | Gly | Ala | Pro | |
| | | | 915 | | | | | 920 | | | | | 925 | | | |

| GCG | CCG | CCG | CCC | CCG | GGC | TCG | CGG | CCT | GCA | GAT | CTT | GAG | CCA | GAT | GAT | 330 |
|---|---|---|---|---|---|---|---|---|---|---|---|---|---|---|---|---|
| Ala | Pro | Pro | Pro | Pro | Gly | Ser | Arg | Pro | Ala | Asp | Leu | Glu | Pro | Asp | Asp | |
| | | 930 | | | | 935 | | | | 940 | | | | | | |

| TGT | GCA | TCC | ATT | TAC | ATC | TTT | AAT | GTA | GAT | CCA | CCT | CCA | TCT | ACT | TTA | 378 |
|---|---|---|---|---|---|---|---|---|---|---|---|---|---|---|---|---|
| Cys | Ala | Ser | Ile | Tyr | Ile | Phe | Asn | Val | Asp | Pro | Pro | Pro | Ser | Thr | Leu | |
| | 945 | | | | | 950 | | | | | 955 | | | | | |

| ACC | ACA | CCA | CTT | TGC | TTA | CCA | CAT | CAT | GGA | TTA | CCG | TCT | CAC | TCT | TCT | 426 |
|---|---|---|---|---|---|---|---|---|---|---|---|---|---|---|---|---|
| Thr | Thr | Pro | Leu | Cys | Leu | Pro | His | His | Gly | Leu | Pro | Ser | His | Ser | Ser | |
| 960 | | | | | 965 | | | | | 970 | | | | | 975 | |

| GTT | TTG | TCA | CCA | TCG | TTT | CAG | CTC | CAA | AGT | CAC | AAA | AAC | TAT | GAA | GGA | 474 |
|---|---|---|---|---|---|---|---|---|---|---|---|---|---|---|---|---|
| Val | Leu | Ser | Pro | Ser | Phe | Gln | Leu | Gln | Ser | His | Lys | Asn | Tyr | Glu | Gly | |
| | | | | 980 | | | | | 985 | | | | | 990 | | |

| ACT | TGT | GAG | ATT | CCT | GAA | TCT | AAA | TAT | AGC | CCA | TTA | GGT | GGT | CCC | AAA | 522 |
|---|---|---|---|---|---|---|---|---|---|---|---|---|---|---|---|---|
| Thr | Cys | Glu | Ile | Pro | Glu | Ser | Lys | Tyr | Ser | Pro | Leu | Gly | Gly | Pro | Lys | |
| | | | 995 | | | | | 1000 | | | | | 1005 | | | |

| CCC | TTT | GAG | TGC | CCA | AGT | ATT | CAA | ATT | ACA | TCT | ATC | TCT | CCT | AAC | TGT | 570 |
|---|---|---|---|---|---|---|---|---|---|---|---|---|---|---|---|---|
| Pro | Phe | Glu | Cys | Pro | Ser | Ile | Gln | Ile | Thr | Ser | Ile | Ser | Pro | Asn | Cys | |
| | | 1010 | | | | 1015 | | | | 1020 | | | | | | |

| CAT | CAA | GAA | TTA | GAT | GCA | CAT | GAA | GAT | GAC | CTA | CAG | ATA | AAT | GAC | CCA | 618 |
|---|---|---|---|---|---|---|---|---|---|---|---|---|---|---|---|---|
| His | Gln | Glu | Leu | Asp | Ala | His | Glu | Asp | Asp | Leu | Gln | Ile | Asn | Asp | Pro | |
| | 1025 | | | | 1030 | | | | | 1035 | | | | | | |

| GAA | CGG | GAA | TTT | TTG | GAA | AGG | CCT | TCT | AGA | GAT | CAT | CTC | TAT | CTT | CCT | 666 |
|---|---|---|---|---|---|---|---|---|---|---|---|---|---|---|---|---|
| Glu | Arg | Glu | Phe | Leu | Glu | Arg | Pro | Ser | Arg | Asp | His | Leu | Tyr | Leu | Pro | |
| 1040 | | | | | 1045 | | | | | 1050 | | | | | 1055 | |

| CTT | GAG | CCA | TCC | TAC | CGG | GAG | TCT | TCT | CTT | AGT | CCT | AGT | CCT | GCC | AGC | 714 |
|---|---|---|---|---|---|---|---|---|---|---|---|---|---|---|---|---|
| Leu | Glu | Pro | Ser | Tyr | Arg | Glu | Ser | Ser | Leu | Ser | Pro | Ser | Pro | Ala | Ser | |
| | | | | 1060 | | | | | 1065 | | | | | 1070 | | |

```
AGC  ATC  TCT  TCT  AGG  AGT  TGG  TTC  TCT  GAT  GCA  TCT  TCT  TGT  GAA  TCG     762
```

| | |
|---|---|
| Ser Ile Ser Ser Arg Ser Trp Phe Ser Asp Ala Ser Ser Cys Glu Ser<br>1075 1080 1085 | |
| CTT TCA CAT ATT TAT GAT GAT GTG GAC TCA GAG TTG AAT GAA GCT GCA<br>Leu Ser His Ile Tyr Asp Asp Val Asp Ser Glu Leu Asn Glu Ala Ala<br>1090 1095 1100 | 810 |
| GCC CGA TTT ACC CTT GGA TCC CCT CTG ACT TCT CCT GGT GGC TCT CCA<br>Ala Arg Phe Thr Leu Gly Ser Pro Leu Thr Ser Pro Gly Gly Ser Pro<br>1105 1110 1115 | 858 |
| GGG GGC TGC CCT GGA GAA GAA ACT TGG CAT CAA CAG TAT GGA CTT GGA<br>Gly Gly Cys Pro Gly Glu Glu Thr Trp His Gln Gln Tyr Gly Leu Gly<br>1120 1125 1130 1135 | 906 |
| CAC TCA TTA TCA CCC AGG CAA TCT CCT TGC CAC TCT CCT AGA TCC AGT<br>His Ser Leu Ser Pro Arg Gln Ser Pro Cys His Ser Pro Arg Ser Ser<br>1140 1145 1150 | 954 |
| GTC ACT GAT GAG AAT TGG CTG AGC CCC AGG CCA GCC TCA GGA CCC TCA<br>Val Thr Asp Glu Asn Trp Leu Ser Pro Arg Pro Ala Ser Gly Pro Ser<br>1155 1160 1165 | 1002 |
| TCA AGG CCC ACA TCC CCC TGT GGG AAA CGG AGG CAC TCC AGT GCT GAA<br>Ser Arg Pro Thr Ser Pro Cys Gly Lys Arg Arg His Ser Ser Ala Glu<br>1170 1175 1180 | 1050 |
| GTT TGT TAT GCT GGG TCC CTT TCA CCC CAT CAC TCA CCT GTT CCT TCA<br>Val Cys Tyr Ala Gly Ser Leu Ser Pro His His Ser Pro Val Pro Ser<br>1185 1190 1195 | 1098 |
| CCT GGT CAC TCC CCC AGG GGA AGT GTG ACA GAA GAT ACG TGG CTC AAT<br>Pro Gly His Ser Pro Arg Gly Ser Val Thr Glu Asp Thr Trp Leu Asn<br>1200 1205 1210 1215 | 1146 |
| GCT TCT GTC CAT GGT GGG TCA GGC CTT GGC CCT GCA GTT TTT CCA TTT<br>Ala Ser Val His Gly Gly Ser Gly Leu Gly Pro Ala Val Phe Pro Phe<br>1220 1225 1230 | 1194 |
| CAG TAC TGT GTA GAG ACT GAC ATC CCT CTC AAA ACA AGG AAA ACT TCT<br>Gln Tyr Cys Val Glu Thr Asp Ile Pro Leu Lys Thr Arg Lys Thr Ser<br>1235 1240 1245 | 1242 |
| GAA GAT CAA GCT GCC ATA CTA CCA GGA AAA TTA GAG CTG TGT TCA GAT<br>Glu Asp Gln Ala Ala Ile Leu Pro Gly Lys Leu Glu Leu Cys Ser Asp<br>1250 1255 1260 | 1290 |
| GAC CAA GGG AGT TTA TCA CCA GCC CGG GAG ACT TCA ATA GAT GAT GGC<br>Asp Gln Gly Ser Leu Ser Pro Ala Arg Glu Thr Ser Ile Asp Asp Gly<br>1265 1270 1275 | 1338 |
| CTT GGA TCT CAG TAT CCT TTA AAG AAA GAT TCA TGT GGT GAT CAG TTT<br>Leu Gly Ser Gln Tyr Pro Leu Lys Lys Asp Ser Cys Gly Asp Gln Phe<br>1280 1285 1290 1295 | 1386 |
| CTT TCA GTT CCT TCA CCC TTT ACC TGG AGC AAA CCA AAG CCT GGC CAC<br>Leu Ser Val Pro Ser Pro Phe Thr Trp Ser Lys Pro Lys Pro Gly His<br>1300 1305 1310 | 1434 |
| ACC CCT ATA TTT CGC ACA TCT TCA TTA CCT CCA CTA GAC TGG CCT TTA<br>Thr Pro Ile Phe Arg Thr Ser Ser Leu Pro Pro Leu Asp Trp Pro Leu<br>1315 1320 1325 | 1482 |
| CCA GCT CAT TTT GGA CAA TGT GAA CTG AAA ATA GAA GTG CAA CCT AAA<br>Pro Ala His Phe Gly Gln Cys Glu Leu Lys Ile Glu Val Gln Pro Lys<br>1330 1335 1340 | 1530 |
| ACT CAT CAT CGA GCC CAT TAT GAA ACT GAA GGT AGC CGA GGG GCA GTA<br>Thr His His Arg Ala His Tyr Glu Thr Glu Gly Ser Arg Gly Ala Val<br>1345 1350 1355 | 1578 |
| AAA GCA TCT ACT GGG GGA CAT CCT GTT GTG AAG CTC CTG GGC TAT AAC<br>Lys Ala Ser Thr Gly Gly His Pro Val Val Lys Leu Leu Gly Tyr Asn<br>1360 1365 1370 1375 | 1626 |
| GAA AAG CCA ATA AAT CTA CAA ATG TTT ATT GGG ACA GCA GAT GAT CGA<br>Glu Lys Pro Ile Asn Leu Gln Met Phe Ile Gly Thr Ala Asp Asp Arg<br>1380 1385 1390 | 1674 |
| TAT TTA CGA CCT CAT GCA TTT TAC CAG GTG CAT CGA ATC ACT GGG AAG | 1722 |

|   |   |   |   |   |   |   |   |   |   |   |   |   |   |   |   |   |
|---|---|---|---|---|---|---|---|---|---|---|---|---|---|---|---|---|
| Tyr | Leu | Arg | Pro | His | Ala | Phe | Tyr | Gln | Val | His | Arg | Ile | Thr | Gly | Lys | |
|  |  | 1395 |  |  |  |  | 1400 |  |  |  |  | 1405 |  |  |  |

```
ACA GTC GCT ACT GCA AGC CAA GAG ATA ATA ATT GCC AGT ACA AAA GTT   1770
Thr Val Ala Thr Ala Ser Gln Glu Ile Ile Ile Ala Ser Thr Lys Val
    1410            1415                1420

CTG GAA ATT CCA CTT CTT CCT GAA AAT AAT ATG TCA GCC AGT ATT GAT   1818
Leu Glu Ile Pro Leu Leu Pro Glu Asn Asn Met Ser Ala Ser Ile Asp
1425            1430                1435

TGT GCA GGT ATT TTG AAA CTC CGC AAT TCA GAT ATA GAA CTT CGA AAA   1866
Cys Ala Gly Ile Leu Lys Leu Arg Asn Ser Asp Ile Glu Leu Arg Lys
1440            1445                1450                1455

GGA GAA ACT GAT ATT GGC AGA AAG AAT ACT AGA GTA CGA CTT GTG TTT   1914
Gly Glu Thr Asp Ile Gly Arg Lys Asn Thr Arg Val Arg Leu Val Phe
                1460                1465                1470

CGT GTA CAC ATC CCA CAG CCC AGT GGA AAA GTC CTT TCT CTG CAG ATA   1962
Arg Val His Ile Pro Gln Pro Ser Gly Lys Val Leu Ser Leu Gln Ile
            1475                1480                1485

GCC TCT ATA CCC GTT GAG TGC TCC CAG CGG TCT GCT CAA GAA CTT CCT   2010
Ala Ser Ile Pro Val Glu Cys Ser Gln Arg Ser Ala Gln Glu Leu Pro
        1490                1495                1500

CAT ATT GAG AAG TAC AGT ATC AAC AGT TGT TCT GTA AAT GGA GGT CAT   2058
His Ile Glu Lys Tyr Ser Ile Asn Ser Cys Ser Val Asn Gly Gly His
    1505                1510                1515

GAA ATG GTT GTG ACT GGA TCT AAT TTT CTT CCA GAA TCC AAA ATC ATT   2106
Glu Met Val Val Thr Gly Ser Asn Phe Leu Pro Glu Ser Lys Ile Ile
1520                1525                1530                1535

TTT CTT GAA AAA GGA CAA GAT GGA CGA CCT CAG TGG GAG GTA GAA GGG   2154
Phe Leu Glu Lys Gly Gln Asp Gly Arg Pro Gln Trp Glu Val Glu Gly
                1540                1545                1550

AAG ATA ATC AGG GAA AAA TGT CAA GGG GCT CAC ATT GTC CTT GAA GTT   2202
Lys Ile Ile Arg Glu Lys Cys Gln Gly Ala His Ile Val Leu Glu Val
            1555                1560                1565

CCT CCA TAT CAT AAC CCA GCA GTT ACA GCT GCA GTG CAG GTG CAC TTT   2250
Pro Pro Tyr His Asn Pro Ala Val Thr Ala Ala Val Gln Val His Phe
        1570                1575                1580

TAT CTT TGC AAT GGC AAG AGG AAA AAA AGC CAG TCT CAA CGT TTT ACT   2298
Tyr Leu Cys Asn Gly Lys Arg Lys Lys Ser Gln Ser Gln Arg Phe Thr
    1585                1590                1595

TAT ACA CCA GGT ACG AGG AGT CAT GAT GGT TTA CTA TAG AGCTTTCTTT   2347
Tyr Thr Pro Gly Thr Arg Ser His Asp Gly Leu Leu *
1600                1605                1610

CCTAATGAAT AAAAAGTTAT TTAACGAACA AAAAAAAAAA AAAAAAAAAA AAAAAAAA   2406
```

( 2 ) INFORMATION FOR SEQ ID NO:8:

( i ) SEQUENCE CHARACTERISTICS:
        ( A ) LENGTH: 708 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Thr Thr Ala Asn Cys Gly Ala His Asp Glu Leu Asp Phe Lys Leu
1               5                   10                  15

Val Phe Gly Glu Asp Gly Ala Pro Ala Pro Pro Pro Gly Ser Arg
                20                  25                  30

Pro Ala Asp Leu Glu Pro Asp Asp Cys Ala Ser Ile Tyr Ile Phe Asn
            35                  40                  45

Val Asp Pro Pro Pro Ser Thr Leu Thr Thr Pro Leu Cys Leu Pro His
        50                  55                  60
```

| | | | | | | | | | | | | | | | |
|---|---|---|---|---|---|---|---|---|---|---|---|---|---|---|---|
| His | Gly | Leu | Pro | Ser | His | Ser | Ser | Val | Leu | Ser | Pro | Ser | Phe | Gln | Leu |
| 65 | | | | 70 | | | | 75 | | | | | | | 80 |
| Gln | Ser | His | Lys | Asn | Tyr | Glu | Gly | Thr | Cys | Glu | Ile | Pro | Glu | Ser | Lys |
| | | | | 85 | | | | | 90 | | | | | 95 | |
| Tyr | Ser | Pro | Leu | Gly | Gly | Pro | Lys | Pro | Phe | Glu | Cys | Pro | Ser | Ile | Gln |
| | | | | 100 | | | | | 105 | | | | | 110 | |
| Ile | Thr | Ser | Ile | Ser | Pro | Asn | Cys | His | Gln | Glu | Leu | Asp | Ala | His | Glu |
| | | | 115 | | | | | 120 | | | | | 125 | | |
| Asp | Asp | Leu | Gln | Ile | Asn | Asp | Pro | Glu | Arg | Glu | Phe | Leu | Glu | Arg | Pro |
| | 130 | | | | | 135 | | | | | | 140 | | | |
| Ser | Arg | Asp | His | Leu | Tyr | Leu | Pro | Leu | Glu | Pro | Ser | Tyr | Arg | Glu | Ser |
| 145 | | | | | 150 | | | | | 155 | | | | | 160 |
| Ser | Leu | Ser | Pro | Ser | Pro | Ala | Ser | Ser | Ile | Ser | Ser | Arg | Ser | Trp | Phe |
| | | | | 165 | | | | | 170 | | | | | 175 | |
| Ser | Asp | Ala | Ser | Ser | Cys | Glu | Ser | Leu | Ser | His | Ile | Tyr | Asp | Asp | Val |
| | | | 180 | | | | | 185 | | | | | 190 | | |
| Asp | Ser | Glu | Leu | Asn | Glu | Ala | Ala | Ala | Arg | Phe | Thr | Leu | Gly | Ser | Pro |
| | | 195 | | | | | 200 | | | | | 205 | | | |
| Leu | Thr | Ser | Pro | Gly | Gly | Ser | Pro | Gly | Gly | Cys | Pro | Gly | Glu | Glu | Thr |
| | 210 | | | | | 215 | | | | | 220 | | | | |
| Trp | His | Gln | Gln | Tyr | Gly | Leu | Gly | His | Ser | Leu | Ser | Pro | Arg | Gln | Ser |
| 225 | | | | | 230 | | | | | 235 | | | | | 240 |
| Pro | Cys | His | Ser | Pro | Arg | Ser | Ser | Val | Thr | Asp | Glu | Asn | Trp | Leu | Ser |
| | | | | 245 | | | | | 250 | | | | | 255 | |
| Pro | Arg | Pro | Ala | Ser | Gly | Pro | Ser | Ser | Arg | Pro | Thr | Ser | Pro | Cys | Gly |
| | | | 260 | | | | | 265 | | | | | 270 | | |
| Lys | Arg | Arg | His | Ser | Ser | Ala | Glu | Val | Cys | Tyr | Ala | Gly | Ser | Leu | Ser |
| | | 275 | | | | | 280 | | | | | 285 | | | |
| Pro | His | His | Ser | Pro | Val | Pro | Ser | Pro | Gly | His | Ser | Pro | Arg | Gly | Ser |
| | 290 | | | | | 295 | | | | | 300 | | | | |
| Val | Thr | Glu | Asp | Thr | Trp | Leu | Asn | Ala | Ser | Val | His | Gly | Gly | Ser | Gly |
| 305 | | | | | 310 | | | | | 315 | | | | | 320 |
| Leu | Gly | Pro | Ala | Val | Phe | Pro | Phe | Gln | Tyr | Cys | Val | Glu | Thr | Asp | Ile |
| | | | | 325 | | | | | 330 | | | | | 335 | |
| Pro | Leu | Lys | Thr | Arg | Lys | Thr | Ser | Glu | Asp | Gln | Ala | Ala | Ile | Leu | Pro |
| | | | 340 | | | | | 345 | | | | | 350 | | |
| Gly | Lys | Leu | Glu | Leu | Cys | Ser | Asp | Asp | Gln | Gly | Ser | Leu | Ser | Pro | Ala |
| | | 355 | | | | | 360 | | | | | 365 | | | |
| Arg | Glu | Thr | Ser | Ile | Asp | Asp | Gly | Leu | Gly | Ser | Gln | Tyr | Pro | Leu | Lys |
| | 370 | | | | | 375 | | | | | 380 | | | | |
| Lys | Asp | Ser | Cys | Gly | Asp | Gln | Phe | Leu | Ser | Val | Pro | Ser | Pro | Phe | Thr |
| 385 | | | | | 390 | | | | | 395 | | | | | 400 |
| Trp | Ser | Lys | Pro | Lys | Pro | Gly | His | Thr | Pro | Ile | Phe | Arg | Thr | Ser | Ser |
| | | | | 405 | | | | | 410 | | | | | 415 | |
| Leu | Pro | Pro | Leu | Asp | Trp | Pro | Leu | Pro | Ala | His | Phe | Gly | Gln | Cys | Glu |
| | | | 420 | | | | | 425 | | | | | 430 | | |
| Leu | Lys | Ile | Glu | Val | Gln | Pro | Lys | Thr | His | His | Arg | Ala | His | Tyr | Glu |
| | | 435 | | | | | 440 | | | | | 445 | | | |
| Thr | Glu | Gly | Ser | Arg | Gly | Ala | Val | Lys | Ala | Ser | Thr | Gly | Gly | His | Pro |
| | 450 | | | | | 455 | | | | | 460 | | | | |
| Val | Val | Lys | Leu | Leu | Gly | Tyr | Asn | Glu | Lys | Pro | Ile | Asn | Leu | Gln | Met |
| 465 | | | | | 470 | | | | | 475 | | | | | 480 |
| Phe | Ile | Gly | Thr | Ala | Asp | Asp | Arg | Tyr | Leu | Arg | Pro | His | Ala | Phe | Tyr |

```
                        485                         490                          495
Gln  Val  His  Arg  Ile  Thr  Gly  Lys  Thr  Val  Ala  Thr  Ala  Ser  Gln  Glu
                    500                      505                      510
Ile  Ile  Ile  Ala  Ser  Thr  Lys  Val  Leu  Glu  Ile  Pro  Leu  Leu  Pro  Glu
               515                      520                      525
Asn  Asn  Met  Ser  Ala  Ser  Ile  Asp  Cys  Ala  Gly  Ile  Leu  Lys  Leu  Arg
          530                      535                      540
Asn  Ser  Asp  Ile  Glu  Leu  Arg  Lys  Gly  Glu  Thr  Asp  Ile  Gly  Arg  Lys
545                      550                      555                           560
Asn  Thr  Arg  Val  Arg  Leu  Val  Phe  Arg  Val  His  Ile  Pro  Gln  Pro  Ser
                    565                      570                      575
Gly  Lys  Val  Leu  Ser  Leu  Gln  Ile  Ala  Ser  Ile  Pro  Val  Glu  Cys  Ser
               580                      585                      590
Gln  Arg  Ser  Ala  Gln  Glu  Leu  Pro  His  Ile  Glu  Lys  Tyr  Ser  Ile  Asn
          595                      600                      605
Ser  Cys  Ser  Val  Asn  Gly  Gly  His  Glu  Met  Val  Val  Thr  Gly  Ser  Asn
     610                      615                      620
Phe  Leu  Pro  Glu  Ser  Lys  Ile  Ile  Phe  Leu  Glu  Lys  Gly  Gln  Asp  Gly
625                      630                      635                           640
Arg  Pro  Gln  Trp  Glu  Val  Glu  Gly  Lys  Ile  Ile  Arg  Glu  Lys  Cys  Gln
                    645                      650                           655
Gly  Ala  His  Ile  Val  Leu  Glu  Val  Pro  Pro  Tyr  His  Asn  Pro  Ala  Val
               660                      665                      670
Thr  Ala  Ala  Val  Gln  Val  His  Phe  Tyr  Leu  Cys  Asn  Gly  Lys  Arg  Lys
          675                      680                      685
Lys  Ser  Gln  Ser  Gln  Arg  Phe  Thr  Tyr  Thr  Pro  Gly  Thr  Arg  Ser  His
     690                      695                      700
Asp  Gly  Leu  Leu
705
```

( 2 ) INFORMATION FOR SEQ ID NO:09:

( i ) SEQUENCE CHARACTERISTICS:
        ( A ) LENGTH: 2647 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 211..2427

( x i ) SEQUENCE DESCRIPTION: SEQ ID NO:09:

```
CGGCTGCGGT TCCTGGTGCT GCTCGGCGCG CGGCCAGCTT TCGGAACGGA ACGCTCGGCG         60

TCGCGGGCCC CGCCCGGAAA GTTTGCCGTG GAGTCGCGAC CTCTTGGCCC GCGCGGCCCG        120

GCATGAAGCG GCGTTGAGGA GCTGCTGCCG CCGCTTGCCG CTGCCGCCGC CGCCGCCTGA        180

GGAGGAGCTG CAGCACCCTG GGCCACGCCG ATG ACT ACT GCA AAC TGT GGC GCC        234
                                Met Thr Thr Ala Asn Cys Gly Ala
                                  1               5

CAC GAC GAG CTC GAC TTC AAA CTC GTC TTT GGC GAG GAC GGG GCG CCG         282
His Asp Glu Leu Asp Phe Lys Leu Val Phe Gly Glu Asp Gly Ala Pro
         10                  15                  20

GCG CCG CCG CCC CCG GGC TCG CGG CCT GCA GAT CTT GAG CCA GAT GAT         330
Ala Pro Pro Pro Pro Gly Ser Arg Pro Ala Asp Leu Glu Pro Asp Asp
 25                  30                  35                  40

TGT GCA TCC ATT TAC ATC TTT AAT GTA GAT CCA CCT CCA TCT ACT TTA         378
```

```
Cys Ala Ser Ile Tyr Ile Phe Asn Val Asp Pro Pro Pro Ser Thr Leu
             45              50                     55

ACC ACA CCA CTT TGC TTA CCA CAT CAT GGA TTA CCG TCT CAC TCT TCT    426
Thr Thr Pro Leu Cys Leu Pro His His Gly Leu Pro Ser His Ser Ser
             60              65                     70

GTT TTG TCA CCA TCG TTT CAG CTC CAA AGT CAC AAA AAC TAT GAA GGA    474
Val Leu Ser Pro Ser Phe Gln Leu Gln Ser His Lys Asn Tyr Glu Gly
             75              80                     85

ACT TGT GAG ATT CCT GAA TCT AAA TAT AGC CCA TTA GGT GGT CCC AAA    522
Thr Cys Glu Ile Pro Glu Ser Lys Tyr Ser Pro Leu Gly Gly Pro Lys
         90              95                    100

CCC TTT GAG TGC CCA AGT ATT CAA ATT ACA TCT ATC TCT CCT AAC TGT    570
Pro Phe Glu Cys Pro Ser Ile Gln Ile Thr Ser Ile Ser Pro Asn Cys
105             110                 115                    120

CAT CAA GAA TTA GAT GCA CAT GAA GAT CTA CAG ATA AAT GAC CCA         618
His Gln Glu Leu Asp Ala His Glu Asp Leu Gln Ile Asn Asp Pro
                125                 130                    135

GAA CGG GAA TTT TTG GAA AGG CCT TCT AGA GAT CAT CTC TAT CTT CCT    666
Glu Arg Glu Phe Leu Glu Arg Pro Ser Arg Asp His Leu Tyr Leu Pro
                140                 145                    150

CTT GAG CCA TCC TAC CGG GAG TCT TCT CTT AGT CCT AGT CCT GCC AGC    714
Leu Glu Pro Ser Tyr Arg Glu Ser Ser Leu Ser Pro Ser Pro Ala Ser
            155                 160                 165

AGC ATC TCT TCT AGG AGT TGG TTC TCT GAT GCA TCT TCT TGT GAA TCG    762
Ser Ile Ser Ser Arg Ser Trp Phe Ser Asp Ala Ser Ser Cys Glu Ser
    170                 175                 180

CTT TCA CAT ATT TAT GAT GAT GTG GAC TCA GAG TTG AAT GAA GCT GCA    810
Leu Ser His Ile Tyr Asp Asp Val Asp Ser Glu Leu Asn Glu Ala Ala
185                 190                 195                    200

GCC CGA TTT ACC CTT GGA TCC CCT CTG ACT TCT CCT GGT GGC TCT CCA    858
Ala Arg Phe Thr Leu Gly Ser Pro Leu Thr Ser Pro Gly Gly Ser Pro
                205                 210                    215

GGG GGC TGC CCT GGA GAA GAA ACT TGG CAT CAA CAG TAT GGA CTT GGA    906
Gly Gly Cys Pro Gly Glu Glu Thr Trp His Gln Gln Tyr Gly Leu Gly
            220                 225                 230

CAC TCA TTA TCA CCC AGG CAA TCT CCT TGC CAC TCT CCT AGA TCC AGT    954
His Ser Leu Ser Pro Arg Gln Ser Pro Cys His Ser Pro Arg Ser Ser
            235                 240                 245

GTC ACT GAT GAG AAT TGG CTG AGC CCC AGG CCA GCC TCA GGA CCC TCA   1002
Val Thr Asp Glu Asn Trp Leu Ser Pro Arg Pro Ala Ser Gly Pro Ser
            250                 255                 260

TCA AGG CCC ACA TCC CCC TGT GGG AAA CGG AGG CAC TCC AGT GCT GAA   1050
Ser Arg Pro Thr Ser Pro Cys Gly Lys Arg Arg His Ser Ser Ala Glu
265             270                 275                    280

GTT TGT TAT GCT GGG TCC CTT TCA CCC CAT CAC TCA CCT GTT CCT TCA   1098
Val Cys Tyr Ala Gly Ser Leu Ser Pro His His Ser Pro Val Pro Ser
                285                 290                    295

CCT GGT CAC TCC CCC AGG GGA AGT GTG ACA GAA GAT ACG TGG CTC AAT   1146
Pro Gly His Ser Pro Arg Gly Ser Val Thr Glu Asp Thr Trp Leu Asn
            300                 305                 310

GCT TCT GTC CAT GGT GGG TCA GGC CTT GGC CCT GCA GTT TTT CCA TTT   1194
Ala Ser Val His Gly Gly Ser Gly Leu Gly Pro Ala Val Phe Pro Phe
            315                 320                 325

CAG TAC TGT GTA GAG ACT GAC ATC CCT CTC AAA ACA AGG AAA ACT TCT   1242
Gln Tyr Cys Val Glu Thr Asp Ile Pro Leu Lys Thr Arg Lys Thr Ser
            330                 335                 340

GAA GAT CAA GCT GCC ATA CTA CCA GGA AAA TTA GAG CTG TGT TCA GAT   1290
Glu Asp Gln Ala Ala Ile Leu Pro Gly Lys Leu Glu Leu Cys Ser Asp
345                 350                 355                    360

GAC CAA GGG AGT TTA TCA CCA GCC CGG GAG ACT TCA ATA GAT GAT GGC   1338
```

```
Asp Gln Gly Ser Leu Ser Pro Ala Arg Glu Thr Ser Ile Asp Asp Gly
            365             370             375

CTT GGA TCT CAG TAT CCT TTA AAG AAA GAT TCA TGT GGT GAT CAG TTT   1386
Leu Gly Ser Gln Tyr Pro Leu Lys Lys Asp Ser Cys Gly Asp Gln Phe
            380             385             390

CTT TCA GTT CCT TCA CCC TTT ACC TGG AGC AAA CCA AAG CCT GGC CAC   1434
Leu Ser Val Pro Ser Pro Phe Thr Trp Ser Lys Pro Lys Pro Gly His
            395             400             405

ACC CCT ATA TTT CGC ACA TCT TCA TTA CCT CCA CTA GAC TGG CCT TTA   1482
Thr Pro Ile Phe Arg Thr Ser Ser Leu Pro Pro Leu Asp Trp Pro Leu
    410                 415             420

CCA GCT CAT TTT GGA CAA TGT GAA CTG AAA ATA GAA GTG CAA CCT AAA   1530
Pro Ala His Phe Gly Gln Cys Glu Leu Lys Ile Glu Val Gln Pro Lys
425             430             435             440

ACT CAT CAT CGA GCC CAT TAT GAA ACT GAA GGT AGC CGA GGG GCA GTA   1578
Thr His His Arg Ala His Tyr Glu Thr Glu Gly Ser Arg Gly Ala Val
            445             450             455

AAA GCA TCT ACT GGG GGA CAT CCT GTT GTG AAG CTC CTG GGC TAT AAC   1626
Lys Ala Ser Thr Gly Gly His Pro Val Val Lys Leu Leu Gly Tyr Asn
            460             465             470

GAA AAG CCA ATA AAT CTA CAA ATG TTT ATT GGG ACA GCA GAT GAT CGA   1674
Glu Lys Pro Ile Asn Leu Gln Met Phe Ile Gly Thr Ala Asp Asp Arg
        475             480             485

TAT TTA CGA CCT CAT GCA TTT TAC CAG GTG CAT CGA ATC ACT GGG AAG   1722
Tyr Leu Arg Pro His Ala Phe Tyr Gln Val His Arg Ile Thr Gly Lys
            490             495             500

ACA GTC GCT ACT GCA AGC CAA GAG ATA ATA ATT GCC AGT ACA AAA GTT   1770
Thr Val Ala Thr Ala Ser Gln Glu Ile Ile Ile Ala Ser Thr Lys Val
505             510             515             520

CTG GAA ATT CCA CTT CTT CCT GAA AAT AAT ATG TCA GCC AGT ATT GAT   1818
Leu Glu Ile Pro Leu Leu Pro Glu Asn Asn Met Ser Ala Ser Ile Asp
            525             530             535

TGT GCA GGT ATT TTG AAA CTC CGC AAT TCA GAT ATA GAA CTT CGA AAA   1866
Cys Ala Gly Ile Leu Lys Leu Arg Asn Ser Asp Ile Glu Leu Arg Lys
            540             545             550

GGA GAA ACT GAT ATT GGC AGA AAG AAT ACT AGA GTA CGA CTT GTG TTT   1914
Gly Glu Thr Asp Ile Gly Arg Lys Asn Thr Arg Val Arg Leu Val Phe
        555             560             565

CGT GTA CAC ATC CCA CAG CCC AGT GGA AAA GTC CTT TCT CTG CAG ATA   1962
Arg Val His Ile Pro Gln Pro Ser Gly Lys Val Leu Ser Leu Gln Ile
570             575             580

GCC TCT ATA CCC GTT GAG TGC TCC CAG CGG TCT GCT CAA GAA CTT CCT   2010
Ala Ser Ile Pro Val Glu Cys Ser Gln Arg Ser Ala Gln Glu Leu Pro
585             590             595             600

CAT ATT GAG AAG TAC AGT ATC AAC AGT TGT TCT GTA AAT GGA GGT CAT   2058
His Ile Glu Lys Tyr Ser Ile Asn Ser Cys Ser Val Asn Gly Gly His
            605             610             615

GAA ATG GTT GTG ACT GGA TCT AAT TTT CTT CCA GAA TCC AAA ATC ATT   2106
Glu Met Val Val Thr Gly Ser Asn Phe Leu Pro Glu Ser Lys Ile Ile
            620             625             630

TTT CTT GAA AAA GGA CAA GAT GGA CGA CCT CAG TGG GAG GTA GAA GGG   2154
Phe Leu Glu Lys Gly Gln Asp Gly Arg Pro Gln Trp Glu Val Glu Gly
            635             640             645

AAG ATA ATC AGG GAA AAA TGT CAA GGG GCT CAC ATT GTC CTT GAA GTT   2202
Lys Ile Ile Arg Glu Lys Cys Gln Gly Ala His Ile Val Leu Glu Val
            650             655             660

CCT CCA TAT CAT AAC CCA GCA GTT ACA GCT GCA GTG CAG GTG CAC TTT   2250
Pro Pro Tyr His Asn Pro Ala Val Thr Ala Ala Val Gln Val His Phe
665             670             675             680

TAT CTT TGC AAT GGC AAG AGG AAA AAA AGC CAG TCT CAA CGT TTT ACT   2298
```

```
            Tyr Leu Cys Asn Gly Lys Arg Lys Lys Ser Gln Ser Gln Arg Phe Thr
                          685                 690                 695

TAT ACA CCA GTT TTG ATG AAG CAA GAA CAC AGA GAA GAG ATT GAT TTG                2346
Tyr Thr Pro Val Leu Met Lys Gln Glu His Arg Glu Glu Ile Asp Leu
            700                 705                 710

TCT TCA GTT CCA ACT TTG CCA CAG ACC TCT CGG CAA ACT CTG CTC GGG                2394
Ser Ser Val Pro Thr Leu Pro Gln Thr Ser Arg Gln Thr Leu Leu Gly
            715                 720                 725

TCT CAG CCT CCT TCA GCT TCT CCT CCA ACA GTT TGATCTCCTC TTCATATTTA              2447
Ser Gln Pro Pro Ser Ala Ser Pro Pro Thr Val
            730                 735

TCTTCTTTGG TGGAATACTT GTCCGCCTGG GCCTCCAGGG ATTTCAAGTT GTTGGTAACA              2507

ATTTTCAGCT CCTCCTCTAG GTCCCCACAT TTACTCTCGG CCACCTCAGC CCTCTCCTCC              2567

GAGCGCTCCA GCTCTCCTTC CAGGATCACC AGCTTCCTGG CCACCTCTTC ATATTTGCGG              2627

TCTGAATCCT CAGCGATGTG                                                          2647
```

( 2 ) INFORMATION FOR SEQ ID NO:10:

( i ) SEQUENCE CHARACTERISTICS:
        ( A ) LENGTH: 739 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Met Thr Thr Ala Asn Cys Gly Ala His Asp Glu Leu Asp Phe Lys Leu
 1               5                  10                  15

Val Phe Gly Glu Asp Gly Ala Pro Ala Pro Pro Pro Gly Ser Arg
                20                  25                  30

Pro Ala Asp Leu Glu Pro Asp Cys Ala Ser Ile Tyr Ile Phe Asn
            35                  40                  45

Val Asp Pro Pro Pro Ser Thr Leu Thr Thr Pro Leu Cys Leu Pro His
     50                  55                  60

His Gly Leu Pro Ser His Ser Ser Val Leu Ser Pro Ser Phe Gln Leu
 65                  70                  75                  80

Gln Ser His Lys Asn Tyr Glu Gly Thr Cys Glu Ile Pro Glu Ser Lys
                85                  90                  95

Tyr Ser Pro Leu Gly Gly Pro Lys Pro Phe Glu Cys Pro Ser Ile Gln
                100                 105                 110

Ile Thr Ser Ile Ser Pro Asn Cys His Gln Glu Leu Asp Ala His Glu
            115                 120                 125

Asp Asp Leu Gln Ile Asn Asp Pro Glu Arg Glu Phe Leu Glu Arg Pro
     130                 135                 140

Ser Arg Asp His Leu Tyr Leu Pro Leu Glu Pro Ser Tyr Arg Glu Ser
145                 150                 155                 160

Ser Leu Ser Pro Ser Pro Ala Ser Ser Ile Ser Ser Arg Ser Trp Phe
                165                 170                 175

Ser Asp Ala Ser Ser Cys Glu Ser Leu Ser His Ile Tyr Asp Asp Val
            180                 185                 190

Asp Ser Glu Leu Asn Glu Ala Ala Ala Arg Phe Thr Leu Gly Ser Pro
     195                 200                 205

Leu Thr Ser Pro Gly Gly Ser Pro Gly Gly Cys Pro Gly Glu Glu Thr
210                 215                 220

Trp His Gln Gln Tyr Gly Leu Gly His Ser Leu Ser Pro Arg Gln Ser
225                 230                 235                 240
```

| | | | | | | | | | | | | | | | |
|---|---|---|---|---|---|---|---|---|---|---|---|---|---|---|---|
|Pro|Cys|His|Ser|Pro 245|Arg|Ser|Ser|Val|Thr 250|Asp|Glu|Asn|Trp|Leu 255|Ser|
|Pro|Arg|Pro|Ala 260|Ser|Gly|Pro|Ser|Ser 265|Arg|Pro|Thr|Ser|Pro 270|Cys|Gly|
|Lys|Arg|Arg|His 275|Ser|Ser|Ala|Glu 280|Val|Cys|Tyr|Ala|Gly 285|Ser|Leu|Ser|
|Pro|His 290|His|Ser|Pro|Val|Pro 295|Ser|Pro|Gly|His|Ser 300|Pro|Arg|Gly|Ser|
|Val 305|Thr|Glu|Asp|Thr|Trp 310|Leu|Asn|Ala|Ser|Val 315|His|Gly|Gly|Ser|Gly 320|
|Leu|Gly|Pro|Ala|Val|Phe 325|Pro|Phe|Gln|Tyr 330|Cys|Val|Glu|Thr|Asp 335|Ile|
|Pro|Leu|Lys|Thr 340|Arg|Lys|Thr|Ser|Glu 345|Asp|Gln|Ala|Ala|Ile 350|Leu|Pro|
|Gly|Lys|Leu 355|Glu|Leu|Cys|Ser|Asp 360|Asp|Gln|Gly|Ser|Leu 365|Ser|Pro|Ala|
|Arg|Glu 370|Thr|Ser|Ile|Asp|Asp 375|Gly|Leu|Gly|Ser|Gln 380|Tyr|Pro|Leu|Lys|
|Lys 385|Asp|Ser|Cys|Gly|Asp 390|Gln|Phe|Leu|Ser|Val 395|Pro|Ser|Pro|Phe|Thr 400|
|Trp|Ser|Lys|Pro|Lys 405|Pro|Gly|His|Thr|Pro 410|Ile|Phe|Arg|Thr|Ser 415|Ser|
|Leu|Pro|Pro|Leu 420|Asp|Trp|Pro|Leu|Pro 425|Ala|His|Phe|Gly|Gln 430|Cys|Glu|
|Leu|Lys|Ile 435|Glu|Val|Gln|Pro|Lys 440|Thr|His|His|Arg|Ala 445|His|Tyr|Glu|
|Thr|Glu 450|Gly|Ser|Arg|Gly|Ala 455|Val|Lys|Ala|Ser|Thr 460|Gly|Gly|His|Pro|
|Val 465|Val|Lys|Leu|Leu|Gly 470|Tyr|Asn|Glu|Lys|Pro 475|Ile|Asn|Leu|Gln|Met 480|
|Phe|Ile|Gly|Thr|Ala 485|Asp|Asp|Arg|Tyr|Leu 490|Arg|Pro|His|Ala|Phe 495|Tyr|
|Gln|Val|His|Arg 500|Ile|Thr|Gly|Lys|Thr 505|Val|Ala|Thr|Ala|Ser 510|Gln|Glu|
|Ile|Ile|Ile 515|Ala|Ser|Thr|Lys|Val 520|Leu|Glu|Ile|Pro|Leu 525|Leu|Pro|Glu|
|Asn|Asn 530|Met|Ser|Ala|Ser|Ile 535|Asp|Cys|Ala|Gly|Ile 540|Leu|Lys|Leu|Arg|
|Asn 545|Ser|Asp|Ile|Glu|Leu 550|Arg|Lys|Gly|Glu|Thr 555|Asp|Ile|Gly|Arg|Lys 560|
|Asn|Thr|Arg|Val|Arg 565|Leu|Val|Phe|Arg|Val 570|His|Ile|Pro|Gln|Pro 575|Ser|
|Gly|Lys|Val|Leu 580|Ser|Leu|Gln|Ile|Ala 585|Ser|Ile|Pro|Val|Glu 590|Cys|Ser|
|Gln|Arg|Ser 595|Ala|Gln|Glu|Leu|Pro 600|His|Ile|Glu|Lys|Tyr 605|Ser|Ile|Asn|
|Ser|Cys 610|Ser|Val|Asn|Gly|Gly 615|His|Glu|Met|Val|Val 620|Thr|Gly|Ser|Asn|
|Phe 625|Leu|Pro|Glu|Ser|Lys 630|Ile|Ile|Phe|Leu|Glu 635|Lys|Gly|Gln|Asp|Gly 640|
|Arg|Pro|Gln|Trp|Glu 645|Val|Glu|Gly|Lys|Ile 650|Ile|Arg|Glu|Lys|Cys 655|Gln|
|Gly|Ala|His|Ile|Val 660|Leu|Glu|Val|Pro|Pro 665|Tyr|His|Asn|Pro|Ala 670|Val|

```
Thr Ala Ala Val Gln Val His Phe Tyr Leu Cys Asn Gly Lys Arg Lys
        675                 680                 685

Lys Ser Gln Ser Gln Arg Phe Thr Tyr Thr Pro Val Leu Met Lys Gln
    690                 695                 700

Glu His Arg Glu Glu Ile Asp Leu Ser Ser Val Pro Thr Leu Pro Gln
705                 710                 715                 720

Thr Ser Arg Gln Thr Leu Leu Gly Ser Gln Pro Pro Ser Ala Ser Pro
            725                 730                 735

Pro Thr Val
```

( 2 ) INFORMATION FOR SEQ ID NO:11:

( i ) SEQUENCE CHARACTERISTICS:
       ( A ) LENGTH: 3969 base pairs
       ( B ) TYPE: nucleic acid
       ( C ) STRANDEDNESS: double
       ( D ) TOPOLOGY: linear ( i i ) MOLECULE TYPE: cDNA ( i x ) FEATURE:
       ( A ) NAME/KEY: CDS
       ( B ) LOCATION: 211..3414

( x i ) SEQUENCE DESCRIPTION: SEQ ID NO:11:

```
CGGCTGCGGT TCCTGGTGCT GCTCGGCGCG CGGCCAGCTT TCGGAACGGA ACGCTCGGCG      60

TCGCGGGCCC CGCCCGGAAA GTTTGCCGTG GAGTCGCGAC CTCTTGGCCC GCGCGGCCCG     120

GCATGAAGCG GCGTTGAGGA GCTGCTGCCG CCGCTTGCCG CTGCCGCCGC CGCCGCCTGA     180

GGAGGAGCTG CAGCACCCTG GGCCACGCCG ATG ACT ACT GCA AAC TGT GGC GCC     234
                                 Met Thr Thr Ala Asn Cys Gly Ala
                                 740                 745

CAC GAC GAG CTC GAC TTC AAA CTC GTC TTT GGC GAG GAC GGG GCG CCG     282
His Asp Glu Leu Asp Phe Lys Leu Val Phe Gly Glu Asp Gly Ala Pro
    750                 755                 760

GCG CCG CCG CCC CCG GGC TCG CGG CCT GCA GAT CTT GAG CCA GAT GAT     330
Ala Pro Pro Pro Pro Gly Ser Arg Pro Ala Asp Leu Glu Pro Asp Asp
765                 770                 775

TGT GCA TCC ATT TAC ATC TTT AAT GTA GAT CCA CCT CCA TCT ACT TTA     378
Cys Ala Ser Ile Tyr Ile Phe Asn Val Asp Pro Pro Pro Ser Thr Leu
780                 785                 790                 795

ACC ACA CCA CTT TGC TTA CCA CAT CAT GGA TTA CCG TCT CAC TCT TCT     426
Thr Thr Pro Leu Cys Leu Pro His His Gly Leu Pro Ser His Ser Ser
            800                 805                 810

GTT TTG TCA CCA TCG TTT CAG CTC CAA AGT CAC AAA AAC TAT GAA GGA     474
Val Leu Ser Pro Ser Phe Gln Leu Gln Ser His Lys Asn Tyr Glu Gly
        815                 820                 825

ACT TGT GAG ATT CCT GAA TCT AAA TAT AGC CCA TTA GGT GGT CCC AAA     522
Thr Cys Glu Ile Pro Glu Ser Lys Tyr Ser Pro Leu Gly Gly Pro Lys
    830                 835                 840

CCC TTT GAG TGC CCA AGT ATT CAA ATT ACA TCT ATC TCT CCT AAC TGT     570
Pro Phe Glu Cys Pro Ser Ile Gln Ile Thr Ser Ile Ser Pro Asn Cys
845                 850                 855

CAT CAA GAA TTA GAT GCA CAT GAA GAT GAC CTA CAG ATA AAT GAC CCA     618
His Gln Glu Leu Asp Ala His Glu Asp Asp Leu Gln Ile Asn Asp Pro
860                 865                 870                 875

GAA CGG GAA TTT TTG GAA AGG CCT TCT AGA GAT CAT CTC TAT CTT CCT     666
Glu Arg Glu Phe Leu Glu Arg Pro Ser Arg Asp His Leu Tyr Leu Pro
            880                 885                 890

CTT GAG CCA TCC TAC CGG GAG TCT TCT CTT AGT CCT AGT CCT GCC AGC     714
Leu Glu Pro Ser Tyr Arg Glu Ser Ser Leu Ser Pro Ser Pro Ala Ser
```

|  |  |
|---|---|
| AGC ATC TCT TCT AGG AGT TGG TTC TCT GAT GCA TCT TCT TGT GAA TCG<br>Ser Ile Ser Ser Arg Ser Trp Phe Ser Asp Ala Ser Ser Cys Glu Ser<br>910  915  920 | 762 |
| CTT TCA CAT ATT TAT GAT GAT GTG GAC TCA GAG TTG AAT GAA GCT GCA<br>Leu Ser His Ile Tyr Asp Asp Val Asp Ser Glu Leu Asn Glu Ala Ala<br>925  930  935 | 810 |
| GCC CGA TTT ACC CTT GGA TCC CCT CTG ACT TCT CCT GGT GGC TCT CCA<br>Ala Arg Phe Thr Leu Gly Ser Pro Leu Thr Ser Pro Gly Gly Ser Pro<br>940  945  950  955 | 858 |
| GGG GGC TGC CCT GGA GAA GAA ACT TGG CAT CAA CAG TAT GGA CTT GGA<br>Gly Gly Cys Pro Gly Glu Glu Thr Trp His Gln Gln Tyr Gly Leu Gly<br>960  965  970 | 906 |
| CAC TCA TTA TCA CCC AGG CAA TCT CCT TGC CAC TCT CCT AGA TCC AGT<br>His Ser Leu Ser Pro Arg Gln Ser Pro Cys His Ser Pro Arg Ser Ser<br>975  980  985 | 954 |
| GTC ACT GAT GAG AAT TGG CTG AGC CCC AGG CCA GCC TCA GGA CCC TCA<br>Val Thr Asp Glu Asn Trp Leu Ser Pro Arg Pro Ala Ser Gly Pro Ser<br>990  995  1000 | 1002 |
| TCA AGG CCC ACA TCC CCC TGT GGG AAA CGG AGG CAC TCC AGT GCT GAA<br>Ser Arg Pro Thr Ser Pro Cys Gly Lys Arg Arg His Ser Ser Ala Glu<br>1005  1010  1015 | 1050 |
| GTT TGT TAT GCT GGG TCC CTT TCA CCC CAT CAC TCA CCT GTT CCT TCA<br>Val Cys Tyr Ala Gly Ser Leu Ser Pro His His Ser Pro Val Pro Ser<br>1020  1025  1030  1035 | 1098 |
| CCT GGT CAC TCC CCC AGG GGA AGT GTG ACA GAA GAT ACG TGG CTC AAT<br>Pro Gly His Ser Pro Arg Gly Ser Val Thr Glu Asp Thr Trp Leu Asn<br>1040  1045  1050 | 1146 |
| GCT TCT GTC CAT GGT GGG TCA GGC CTT GGC CCT GCA GTT TTT CCA TTT<br>Ala Ser Val His Gly Gly Ser Gly Leu Gly Pro Ala Val Phe Pro Phe<br>1055  1060  1065 | 1194 |
| CAG TAC TGT GTA GAG ACT GAC ATC CCT CTC AAA ACA AGG AAA ACT TCT<br>Gln Tyr Cys Val Glu Thr Asp Ile Pro Leu Lys Thr Arg Lys Thr Ser<br>1070  1075  1080 | 1242 |
| GAA GAT CAA GCT GCC ATA CTA CCA GGA AAA TTA GAG CTG TGT TCA GAT<br>Glu Asp Gln Ala Ala Ile Leu Pro Gly Lys Leu Glu Leu Cys Ser Asp<br>1085  1090  1095 | 1290 |
| GAC CAA GGG AGT TTA TCA CCA GCC CGG GAG ACT TCA ATA GAT GAT GGC<br>Asp Gln Gly Ser Leu Ser Pro Ala Arg Glu Thr Ser Ile Asp Asp Gly<br>1100  1105  1110  1115 | 1338 |
| CTT GGA TCT CAG TAT CCT TTA AAG AAA GAT TCA TGT GGT GAT CAG TTT<br>Leu Gly Ser Gln Tyr Pro Leu Lys Lys Asp Ser Cys Gly Asp Gln Phe<br>1120  1125  1130 | 1386 |
| CTT TCA GTT CCT TCA CCC TTT ACC TGG AGC AAA CCA AAG CCT GGC CAC<br>Leu Ser Val Pro Ser Pro Phe Thr Trp Ser Lys Pro Lys Pro Gly His<br>1135  1140  1145 | 1434 |
| ACC CCT ATA TTT CGC ACA TCT TCA TTA CCT CCA CTA GAC TGG CCT TTA<br>Thr Pro Ile Phe Arg Thr Ser Ser Leu Pro Pro Leu Asp Trp Pro Leu<br>1150  1155  1160 | 1482 |
| CCA GCT CAT TTT GGA CAA TGT GAA CTG AAA ATA GAA GTG CAA CCT AAA<br>Pro Ala His Phe Gly Gln Cys Glu Leu Lys Ile Glu Val Gln Pro Lys<br>1165  1170  1175 | 1530 |
| ACT CAT CAT CGA GCC CAT TAT GAA ACT GAA GGT AGC CGA GGG GCA GTA<br>Thr His His Arg Ala His Tyr Glu Thr Glu Gly Ser Arg Gly Ala Val<br>1180  1185  1190  1195 | 1578 |
| AAA GCA TCT ACT GGG GGA CAT CCT GTT GTG AAG CTC CTG GGC TAT AAC<br>Lys Ala Ser Thr Gly Gly His Pro Val Val Lys Leu Leu Gly Tyr Asn<br>1200  1205  1210 | 1626 |
| GAA AAG CCA ATA AAT CTA CAA ATG TTT ATT GGG ACA GCA GAT GAT CGA<br>Glu Lys Pro Ile Asn Leu Gln Met Phe Ile Gly Thr Ala Asp Asp Arg | 1674 |

```
                    1215                        1220                         1225
TAT  TTA  CGA  CCT  CAT  GCA  TTT  TAC  CAG  GTG  CAT  CGA  ATC  ACT  GGG  AAG        1722
Tyr  Leu  Arg  Pro  His  Ala  Phe  Tyr  Gln  Val  His  Arg  Ile  Thr  Gly  Lys
          1230                    1235                         1240

ACA  GTC  GCT  ACT  GCA  AGC  CAA  GAG  ATA  ATA  ATT  GCC  AGT  ACA  AAA  GTT        1770
Thr  Val  Ala  Thr  Ala  Ser  Gln  Glu  Ile  Ile  Ile  Ala  Ser  Thr  Lys  Val
          1245                    1250                         1255

CTG  GAA  ATT  CCA  CTT  CTT  CCT  GAA  AAT  AAT  ATG  TCA  GCC  AGT  ATT  GAT        1818
Leu  Glu  Ile  Pro  Leu  Leu  Pro  Glu  Asn  Asn  Met  Ser  Ala  Ser  Ile  Asp
1260                    1265                         1270                    1275

TGT  GCA  GGT  ATT  TTG  AAA  CTC  CGC  AAT  TCA  GAT  ATA  GAA  CTT  CGA  AAA        1866
Cys  Ala  Gly  Ile  Leu  Lys  Leu  Arg  Asn  Ser  Asp  Ile  Glu  Leu  Arg  Lys
               1280                    1285                         1290

GGA  GAA  ACT  GAT  ATT  GGC  AGA  AAG  AAT  ACT  AGA  GTA  CGA  CTT  GTG  TTT        1914
Gly  Glu  Thr  Asp  Ile  Gly  Arg  Lys  Asn  Thr  Arg  Val  Arg  Leu  Val  Phe
          1295                    1300                         1305

CGT  GTA  CAC  ATC  CCA  CAG  CCC  AGT  GGA  AAA  GTC  CTT  TCT  CTG  CAG  ATA        1962
Arg  Val  His  Ile  Pro  Gln  Pro  Ser  Gly  Lys  Val  Leu  Ser  Leu  Gln  Ile
               1310                    1315                         1320

GCC  TCT  ATA  CCC  GTT  GAG  TGC  TCC  CAG  CGG  TCT  GCT  CAA  GAA  CTT  CCT        2010
Ala  Ser  Ile  Pro  Val  Glu  Cys  Ser  Gln  Arg  Ser  Ala  Gln  Glu  Leu  Pro
          1325                    1330                         1335

CAT  ATT  GAG  AAG  TAC  AGT  ATC  AAC  AGT  TGT  TCT  GTA  AAT  GGA  GGT  CAT        2058
His  Ile  Glu  Lys  Tyr  Ser  Ile  Asn  Ser  Cys  Ser  Val  Asn  Gly  Gly  His
1340                    1345                         1350                    1355

GAA  ATG  GTT  GTG  ACT  GGA  TCT  AAT  TTT  CTT  CCA  GAA  TCC  AAA  ATC  ATT        2106
Glu  Met  Val  Val  Thr  Gly  Ser  Asn  Phe  Leu  Pro  Glu  Ser  Lys  Ile  Ile
          1360                    1365                         1370

TTT  CTT  GAA  AAA  GGA  CAA  GAT  GGA  CGA  CCT  CAG  TGG  GAG  GTA  GAA  GGG        2154
Phe  Leu  Glu  Lys  Gly  Gln  Asp  Gly  Arg  Pro  Gln  Trp  Glu  Val  Glu  Gly
               1375                    1380                         1385

AAG  ATA  ATC  AGG  GAA  AAA  TGT  CAA  GGG  GCT  CAC  ATT  GTC  CTT  GAA  GTT        2202
Lys  Ile  Ile  Arg  Glu  Lys  Cys  Gln  Gly  Ala  His  Ile  Val  Leu  Glu  Val
          1390                    1395                         1400

CCT  CCA  TAT  CAT  AAC  CCA  GCA  GTT  ACA  GCT  GCA  GTG  CAG  GTG  CAC  TTT        2250
Pro  Pro  Tyr  His  Asn  Pro  Ala  Val  Thr  Ala  Ala  Val  Gln  Val  His  Phe
1405                    1410                         1415

TAT  CTT  TGC  AAT  GGC  AAG  AGG  AAA  AAA  AGC  CAG  TCT  CAA  CGT  TTT  ACT        2298
Tyr  Leu  Cys  Asn  Gly  Lys  Arg  Lys  Lys  Ser  Gln  Ser  Gln  Arg  Phe  Thr
1420                    1425                         1430                    1435

TAT  ACA  CCA  GTT  TTG  ATG  AAG  CAA  GAA  CAC  AGA  GAA  GAG  ATT  GAT  TTG        2346
Tyr  Thr  Pro  Val  Leu  Met  Lys  Gln  Glu  His  Arg  Glu  Glu  Ile  Asp  Leu
                              1440                    1445                    1450

TCT  TCA  GTT  CCA  TCT  TTG  CCT  GTG  CCT  CAT  CCT  GCT  CAG  ACC  CAG  AGG        2394
Ser  Ser  Val  Pro  Ser  Leu  Pro  Val  Pro  His  Pro  Ala  Gln  Thr  Gln  Arg
                    1455                    1460                         1465

CCT  TCC  TCT  GAT  TCA  GGG  TGT  TCA  CAT  GAC  AGT  GTA  CTG  TCA  GGA  CAG        2442
Pro  Ser  Ser  Asp  Ser  Gly  Cys  Ser  His  Asp  Ser  Val  Leu  Ser  Gly  Gln
                         1470                    1475                    1480

AGA  AGT  TTG  ATT  TGC  TCC  ATC  CCA  CAA  ACA  TAT  GCA  TCC  ATG  GTG  ACC        2490
Arg  Ser  Leu  Ile  Cys  Ser  Ile  Pro  Gln  Thr  Tyr  Ala  Ser  Met  Val  Thr
          1485                    1490                         1495

TCA  TCC  CAT  CTG  CCA  CAG  TTG  CAG  TGT  AGA  GAT  GAG  AGT  GTT  AGT  AAA        2538
Ser  Ser  His  Leu  Pro  Gln  Leu  Gln  Cys  Arg  Asp  Glu  Ser  Val  Ser  Lys
1500                    1505                         1510                    1515

GAA  CAG  CAT  ATG  ATT  CCT  TCT  CCA  ATT  GTA  CAC  CAG  CCT  TTT  CAA  GTC        2586
Glu  Gln  His  Met  Ile  Pro  Ser  Pro  Ile  Val  His  Gln  Pro  Phe  Gln  Val
          1520                    1525                         1530

ACA  CCA  ACA  CCT  CCT  GTG  GGG  TCT  TCC  TAT  CAG  CCT  ATG  CAA  ACT  AAT        2634
Thr  Pro  Thr  Pro  Pro  Val  Gly  Ser  Ser  Tyr  Gln  Pro  Met  Gln  Thr  Asn
```

|  | 1535 |  |  |  | 1540 |  |  |  |  | 1545 |  |  |  |  |  |
|---|---|---|---|---|---|---|---|---|---|---|---|---|---|---|---|
| GTT | GTG | TAC | AAT | GGA | CCA | ACT | TGT | CTT | CCT | ATT | AAT | GCT | GCC | TCT | AGT | 2682 |
| Val | Val | Tyr | Asn | Gly | Pro | Thr | Cys | Leu | Pro | Ile | Asn | Ala | Ala | Ser | Ser |  |
|  |  |  | 1550 |  |  |  | 1555 |  |  |  |  | 1560 |  |  |  |  |
| CAA | GAA | TTT | GAT | TCA | GTT | TTG | TTT | CAG | CAG | GAT | GCA | ACT | CTT | TCT | GGT | 2730 |
| Gln | Glu | Phe | Asp | Ser | Val | Leu | Phe | Gln | Gln | Asp | Ala | Thr | Leu | Ser | Gly |  |
|  | 1565 |  |  |  |  | 1570 |  |  |  |  | 1575 |  |  |  |  |  |
| TTA | GTG | AAT | CTT | GGC | TGT | CAA | CCA | CTG | TCA | TCC | ATA | CCA | TTT | CAT | TCT | 2778 |
| Leu | Val | Asn | Leu | Gly | Cys | Gln | Pro | Leu | Ser | Ser | Ile | Pro | Phe | His | Ser |  |
| 1580 |  |  |  |  | 1585 |  |  |  |  | 1590 |  |  |  |  | 1595 |  |
| TCA | AAT | TCA | GGC | TCA | ACA | GGA | CAT | CTC | TTA | GCC | CAT | ACA | CCT | CAT | TCT | 2826 |
| Ser | Asn | Ser | Gly | Ser | Thr | Gly | His | Leu | Leu | Ala | His | Thr | Pro | His | Ser |  |
|  |  |  |  | 1600 |  |  |  |  | 1605 |  |  |  |  | 1610 |  |  |
| GTG | CAT | ACC | CTG | CCT | CAT | CTG | CAA | TCA | ATG | GGA | TAT | CAT | TGT | TCA | AAT | 2874 |
| Val | His | Thr | Leu | Pro | His | Leu | Gln | Ser | Met | Gly | Tyr | His | Cys | Ser | Asn |  |
|  |  |  | 1615 |  |  |  |  | 1620 |  |  |  |  | 1625 |  |  |  |
| ACA | GGA | CAA | AGA | TCT | CTT | TCT | TCT | CCA | GTG | GCT | GAC | CAG | ATT | ACA | GGT | 2922 |
| Thr | Gly | Gln | Arg | Ser | Leu | Ser | Ser | Pro | Val | Ala | Asp | Gln | Ile | Thr | Gly |  |
|  |  | 1630 |  |  |  |  | 1635 |  |  |  |  | 1640 |  |  |  |  |
| CAG | CCT | TCG | TCT | CAG | TTA | CAA | CCT | ATT | ACA | TAT | GGT | CCT | TCA | CAT | TCA | 2970 |
| Gln | Pro | Ser | Ser | Gln | Leu | Gln | Pro | Ile | Thr | Tyr | Gly | Pro | Ser | His | Ser |  |
|  | 1645 |  |  |  |  | 1650 |  |  |  |  | 1655 |  |  |  |  |  |
| GGG | TCT | GCT | ACA | ACA | GCT | TCC | CCA | GCA | GCT | TCT | CAT | CCC | TTG | GCT | AGT | 3018 |
| Gly | Ser | Ala | Thr | Thr | Ala | Ser | Pro | Ala | Ala | Ser | His | Pro | Leu | Ala | Ser |  |
| 1660 |  |  |  |  | 1665 |  |  |  |  | 1670 |  |  |  |  | 1675 |  |
| TCA | CCG | CTT | TCT | GGG | CCA | CCA | TCT | CCT | CAG | CTT | CAG | CCT | ATG | CCT | TAC | 3066 |
| Ser | Pro | Leu | Ser | Gly | Pro | Pro | Ser | Pro | Gln | Leu | Gln | Pro | Met | Pro | Tyr |  |
|  |  |  |  | 1680 |  |  |  |  | 1685 |  |  |  |  | 1690 |  |  |
| CAA | TCT | CCT | AGC | TCA | GGA | ACT | GCC | TCA | TCA | CCG | TCT | CCA | GCC | ACC | AGA | 3114 |
| Gln | Ser | Pro | Ser | Ser | Gly | Thr | Ala | Ser | Ser | Pro | Ser | Pro | Ala | Thr | Arg |  |
|  |  |  | 1695 |  |  |  |  | 1700 |  |  |  |  | 1705 |  |  |  |
| ATG | CAT | TCT | GGA | CAG | CAC | TCA | ACT | CAA | GCA | CAA | AGT | ACG | GGC | CAG | GGG | 3162 |
| Met | His | Ser | Gly | Gln | His | Ser | Thr | Gln | Ala | Gln | Ser | Thr | Gly | Gln | Gly |  |
|  |  | 1710 |  |  |  |  | 1715 |  |  |  |  | 1720 |  |  |  |  |
| GGT | CTT | TCT | GCA | CCT | TCA | TCC | TTA | ATA | TGT | CAC | AGT | TTG | TGT | GAT | CCA | 3210 |
| Gly | Leu | Ser | Ala | Pro | Ser | Ser | Leu | Ile | Cys | His | Ser | Leu | Cys | Asp | Pro |  |
|  | 1725 |  |  |  |  | 1730 |  |  |  |  | 1735 |  |  |  |  |  |
| GCG | TCA | TTT | CCA | CCT | GAT | GGG | GCA | ACT | GTG | AGC | ATT | AAA | CCT | GAA | CCA | 3258 |
| Ala | Ser | Phe | Pro | Pro | Asp | Gly | Ala | Thr | Val | Ser | Ile | Lys | Pro | Glu | Pro |  |
| 1740 |  |  |  |  | 1745 |  |  |  |  | 1750 |  |  |  |  | 1755 |  |
| GAA | GAT | CGA | GAG | CCT | AAC | TTT | GCA | ACC | ATT | GGT | CTG | CAG | GAC | ATC | ACT | 3306 |
| Glu | Asp | Arg | Glu | Pro | Asn | Phe | Ala | Thr | Ile | Gly | Leu | Gln | Asp | Ile | Thr |  |
|  |  |  |  | 1760 |  |  |  |  | 1765 |  |  |  |  | 1770 |  |  |
| TTA | GAT | GAT | GAC | CAA | TTT | ATA | TCT | GAC | TTG | GAA | CAC | CAG | CCA | TCA | GGT | 3354 |
| Leu | Asp | Asp | Asp | Gln | Phe | Ile | Ser | Asp | Leu | Glu | His | Gln | Pro | Ser | Gly |  |
|  |  |  | 1775 |  |  |  |  | 1780 |  |  |  |  | 1785 |  |  |  |
| TCA | GCA | GAG | AAA | TGG | CCT | AAC | CAC | AGT | GTG | CTC | TCA | TGT | CCA | GCT | CCT | 3402 |
| Ser | Ala | Glu | Lys | Trp | Pro | Asn | His | Ser | Val | Leu | Ser | Cys | Pro | Ala | Pro |  |
|  |  | 1790 |  |  |  |  | 1795 |  |  |  |  | 1800 |  |  |  |  |
| TTC | TGG | AGA | ATC | TAGAGGTGAA | CGAGATAATT | GGGAGAGACA | TGTCCAGAT |  |  |  |  |  |  |  |  | 3454 |
| Phe | Trp | Arg | Ile |  |  |  |  |  |  |  |  |  |  |  |  |  |
|  |  | 1805 |  |  |  |  |  |  |  |  |  |  |  |  |  |  |

```
TTCTGTTTCC CAAGGAGCAG GGGTGAGCAG GCAGGCTCCC CTCCCGAGTC CTGAGTCCCT      3514

GGATTTAGGA AGATCTGATG GGCTCTAACA GTGCTTACTG CAGCCTTGTG TCCACCACCA      3574

ACTTCTCAGC ATGTTTCTCT CCTTGGACCT TGGGTTTCCA ACTCTGCAGC CTTCAGGTCT      3634

GGGGCCAGGA GTGGGACCCA CCATTTGTGG GGAAAGTAGC ATTCCTCCAC CTCAGGCCTT      3694

GGGTAGATTT GGCAAAAGAA CAGGAGCAGC ATAGGCTGTT TGAGCTTTGG GGAAATGAAC      3754
```

```
TTTGCTTTTT ATATTTAACT AGGATACTTT TATATGATGG GTGCTTTGAG TGTGAATGCA    3814

GCAGGCTCTC TTGTTTCCGA GGTGCTGCTT TTGCAGGTGA CCTGGTTACT TAGCTAGGAT    3874

TGGTGATTTG TACTGCTTTA TGGTCATTTG AAGGGCCCTT TAGTTTTTAT GATAATTTTT    3934

AAAATAGGAA CTTTGATAA  GACCTTCTAG AAGCC                              3969
```

( 2 ) INFORMATION FOR SEQ ID NO:12:

( i ) SEQUENCE CHARACTERISTICS:
        ( A ) LENGTH: 1068 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Thr Thr Ala Asn Cys Gly Ala His Asp Glu Leu Asp Phe Lys Leu
 1               5                  10                  15

Val Phe Gly Glu Asp Gly Ala Pro Ala Pro Pro Pro Gly Ser Arg
                20                  25                  30

Pro Ala Asp Leu Glu Pro Asp Cys Ala Ser Ile Tyr Ile Phe Asn
                35                  40                  45

Val Asp Pro Pro Pro Ser Thr Leu Thr Thr Pro Leu Cys Leu Pro His
    50                  55                  60

His Gly Leu Pro Ser His Ser Ser Val Leu Ser Pro Ser Phe Gln Leu
 65                  70                  75                  80

Gln Ser His Lys Asn Tyr Glu Gly Thr Cys Glu Ile Pro Glu Ser Lys
                85                  90                  95

Tyr Ser Pro Leu Gly Gly Pro Lys Pro Phe Glu Cys Pro Ser Ile Gln
                100                 105                 110

Ile Thr Ser Ile Ser Pro Asn Cys His Gln Glu Leu Asp Ala His Glu
            115                 120                 125

Asp Asp Leu Gln Ile Asn Asp Pro Glu Arg Glu Phe Leu Glu Arg Pro
    130                 135                 140

Ser Arg Asp His Leu Tyr Leu Pro Leu Glu Pro Ser Tyr Arg Glu Ser
145                 150                 155                 160

Ser Leu Ser Pro Ser Pro Ala Ser Ser Ile Ser Ser Arg Ser Trp Phe
                165                 170                 175

Ser Asp Ala Ser Ser Cys Glu Ser Leu Ser His Ile Tyr Asp Asp Val
            180                 185                 190

Asp Ser Glu Leu Asn Glu Ala Ala Ala Arg Phe Thr Leu Gly Ser Pro
    195                 200                 205

Leu Thr Ser Pro Gly Gly Ser Pro Gly Gly Cys Pro Gly Glu Glu Thr
210                 215                 220

Trp His Gln Gln Tyr Gly Leu Gly His Ser Leu Ser Pro Arg Gln Ser
225                 230                 235                 240

Pro Cys His Ser Pro Arg Ser Ser Val Thr Asp Glu Asn Trp Leu Ser
                245                 250                 255

Pro Arg Pro Ala Ser Gly Pro Ser Ser Arg Pro Thr Ser Pro Cys Gly
                260                 265                 270

Lys Arg Arg His Ser Ser Ala Glu Val Cys Tyr Ala Gly Ser Leu Ser
        275                 280                 285

Pro His His Ser Pro Val Pro Ser Pro Gly His Ser Pro Arg Gly Ser
    290                 295                 300

Val Thr Glu Asp Thr Trp Leu Asn Ala Ser Val His Gly Gly Ser Gly
305                 310                 315                 320
```

-continued

| | | | | | | | | | | | | | |
|---|---|---|---|---|---|---|---|---|---|---|---|---|---|
| Leu | Gly | Pro | Ala | Val | Phe | Pro | Phe | Gln | Tyr | Cys | Val | Glu | Thr | Asp | Ile |
| | | | | 325 | | | | | 330 | | | | 335 |
| Pro | Leu | Lys | Thr | Arg | Lys | Thr | Ser | Glu | Asp | Gln | Ala | Ala | Ile | Leu | Pro |
| | | | 340 | | | | | 345 | | | | | 350 | | |
| Gly | Lys | Leu | Glu | Leu | Cys | Ser | Asp | Asp | Gln | Gly | Ser | Leu | Ser | Pro | Ala |
| | | | 355 | | | | | 360 | | | | 365 | | | |
| Arg | Glu | Thr | Ser | Ile | Asp | Asp | Gly | Leu | Gly | Ser | Gln | Tyr | Pro | Leu | Lys |
| | | 370 | | | | 375 | | | | | 380 | | | | |
| Lys | Asp | Ser | Cys | Gly | Asp | Gln | Phe | Leu | Ser | Val | Pro | Ser | Pro | Phe | Thr |
| 385 | | | | | 390 | | | | | 395 | | | | | 400 |
| Trp | Ser | Lys | Pro | Lys | Pro | Gly | His | Thr | Pro | Ile | Phe | Arg | Thr | Ser | Ser |
| | | | | 405 | | | | | 410 | | | | | 415 | |
| Leu | Pro | Pro | Leu | Asp | Trp | Pro | Leu | Pro | Ala | His | Phe | Gly | Gln | Cys | Glu |
| | | | 420 | | | | | 425 | | | | | 430 | | |
| Leu | Lys | Ile | Glu | Val | Gln | Pro | Lys | Thr | His | His | Arg | Ala | His | Tyr | Glu |
| | | 435 | | | | | 440 | | | | | 445 | | | |
| Thr | Glu | Gly | Ser | Arg | Gly | Ala | Val | Lys | Ala | Ser | Thr | Gly | Gly | His | Pro |
| | 450 | | | | 455 | | | | | 460 | | | | | |
| Val | Val | Lys | Leu | Leu | Gly | Tyr | Asn | Glu | Lys | Pro | Ile | Asn | Leu | Gln | Met |
| 465 | | | | | 470 | | | | | 475 | | | | | 480 |
| Phe | Ile | Gly | Thr | Ala | Asp | Asp | Arg | Tyr | Leu | Arg | Pro | His | Ala | Phe | Tyr |
| | | | | 485 | | | | | 490 | | | | | 495 | |
| Gln | Val | His | Arg | Ile | Thr | Gly | Lys | Thr | Val | Ala | Thr | Ala | Ser | Gln | Glu |
| | | | 500 | | | | | 505 | | | | | 510 | | |
| Ile | Ile | Ile | Ala | Ser | Thr | Lys | Val | Leu | Glu | Ile | Pro | Leu | Leu | Pro | Glu |
| | | 515 | | | | | 520 | | | | | 525 | | | |
| Asn | Asn | Met | Ser | Ala | Ser | Ile | Asp | Cys | Ala | Gly | Ile | Leu | Lys | Leu | Arg |
| | 530 | | | | 535 | | | | | 540 | | | | | |
| Asn | Ser | Asp | Ile | Glu | Leu | Arg | Lys | Gly | Glu | Thr | Asp | Ile | Gly | Arg | Lys |
| 545 | | | | | 550 | | | | | 555 | | | | | 560 |
| Asn | Thr | Arg | Val | Arg | Leu | Val | Phe | Arg | Val | His | Ile | Pro | Gln | Pro | Ser |
| | | | | 565 | | | | | 570 | | | | | 575 | |
| Gly | Lys | Val | Leu | Ser | Leu | Gln | Ile | Ala | Ser | Ile | Pro | Val | Glu | Cys | Ser |
| | | | 580 | | | | | 585 | | | | | 590 | | |
| Gln | Arg | Ser | Ala | Gln | Glu | Leu | Pro | His | Ile | Glu | Lys | Tyr | Ser | Ile | Asn |
| | | 595 | | | | | 600 | | | | | 605 | | | |
| Ser | Cys | Ser | Val | Asn | Gly | Gly | His | Glu | Met | Val | Val | Thr | Gly | Ser | Asn |
| | 610 | | | | | 615 | | | | | 620 | | | | |
| Phe | Leu | Pro | Glu | Ser | Lys | Ile | Ile | Phe | Leu | Glu | Lys | Gly | Gln | Asp | Gly |
| 625 | | | | | 630 | | | | | 635 | | | | | 640 |
| Arg | Pro | Gln | Trp | Glu | Val | Glu | Gly | Lys | Ile | Ile | Arg | Glu | Lys | Cys | Gln |
| | | | | 645 | | | | | 650 | | | | | 655 | |
| Gly | Ala | His | Ile | Val | Leu | Glu | Val | Pro | Pro | Tyr | His | Asn | Pro | Ala | Val |
| | | | 660 | | | | | 665 | | | | | 670 | | |
| Thr | Ala | Ala | Val | Gln | Val | His | Phe | Tyr | Leu | Cys | Asn | Gly | Lys | Arg | Lys |
| | | 675 | | | | | 680 | | | | | 685 | | | |
| Lys | Ser | Gln | Ser | Gln | Arg | Phe | Thr | Tyr | Thr | Pro | Val | Leu | Met | Lys | Gln |
| | 690 | | | | | 695 | | | | | 700 | | | | |
| Glu | His | Arg | Glu | Glu | Ile | Asp | Leu | Ser | Ser | Val | Pro | Ser | Leu | Pro | Val |
| 705 | | | | | 710 | | | | | 715 | | | | | 720 |
| Pro | His | Pro | Ala | Gln | Thr | Gln | Arg | Pro | Ser | Ser | Asp | Ser | Gly | Cys | Ser |
| | | | | 725 | | | | | 730 | | | | | 735 | |
| His | Asp | Ser | Val | Leu | Ser | Gly | Gln | Arg | Ser | Leu | Ile | Cys | Ser | Ile | Pro |
| | | | 740 | | | | | 745 | | | | | 750 | | |

```
Gln Thr Tyr Ala Ser Met Val Thr Ser Ser His Leu Pro Gln Leu Gln
        755                 760                 765

Cys Arg Asp Glu Ser Val Ser Lys Glu Gln His Met Ile Pro Ser Pro
770                 775                 780

Ile Val His Gln Pro Phe Gln Val Thr Pro Thr Pro Pro Val Gly Ser
785                 790                 795                 800

Ser Tyr Gln Pro Met Gln Thr Asn Val Val Tyr Asn Gly Pro Thr Cys
                805                 810                 815

Leu Pro Ile Asn Ala Ala Ser Ser Gln Glu Phe Asp Ser Val Leu Phe
                820                 825                 830

Gln Gln Asp Ala Thr Leu Ser Gly Leu Val Asn Leu Gly Cys Gln Pro
            835                 840                 845

Leu Ser Ser Ile Pro Phe His Ser Ser Asn Ser Gly Ser Thr Gly His
    850                 855                 860

Leu Leu Ala His Thr Pro His Ser Val His Thr Leu Pro His Leu Gln
865                 870                 875                 880

Ser Met Gly Tyr His Cys Ser Asn Thr Gly Gln Arg Ser Leu Ser Ser
                885                 890                 895

Pro Val Ala Asp Gln Ile Thr Gly Gln Pro Ser Ser Gln Leu Gln Pro
            900                 905                 910

Ile Thr Tyr Gly Pro Ser His Ser Gly Ser Ala Thr Thr Ala Ser Pro
    915                 920                 925

Ala Ala Ser His Pro Leu Ala Ser Ser Pro Leu Ser Gly Pro Pro Ser
930                 935                 940

Pro Gln Leu Gln Pro Met Pro Tyr Gln Ser Pro Ser Ser Gly Thr Ala
945                 950                 955                 960

Ser Ser Pro Ser Pro Ala Thr Arg Met His Ser Gly Gln His Ser Thr
                965                 970                 975

Gln Ala Gln Ser Thr Gly Gln Gly Gly Leu Ser Ala Pro Ser Ser Leu
            980                 985                 990

Ile Cys His Ser Leu Cys Asp Pro Ala Ser Phe Pro Pro Asp Gly Ala
        995                 1000                1005

Thr Val Ser Ile Lys Pro Glu Pro Glu Asp Arg Glu Pro Asn Phe Ala
1010                1015                1020

Thr Ile Gly Leu Gln Asp Ile Thr Leu Asp Asp Gln Phe Ile Ser
1025                1030                1035                1040

Asp Leu Glu His Gln Pro Ser Gly Ser Ala Glu Lys Trp Pro Asn His
                1045                1050                1055

Ser Val Leu Ser Cys Pro Ala Pro Phe Trp Arg Ile
            1060                1065
```

( 2 ) INFORMATION FOR SEQ ID NO:13:

( i ) SEQUENCE CHARACTERISTICS:
    ( A ) LENGTH: 27 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:13:

```
Asp Ile Glu Leu Arg Lys Gly Glu Thr Asp Ile Gly Arg Lys Asn Thr
1               5                   10                  15

Arg Val Arg Leu Val Phe Arg Val His Xaa Pro
        20                  25
```

(2) INFORMATION FOR SEQ ID NO:14:

(i) SEQUENCE CHARACTERISTICS:
       (A) LENGTH: 13 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:14:

```
Pro Xaa Glu Cys Ser Gln Arg Ser Ala Xaa Glu Leu Pro
 1           5                        10
```

(2) INFORMATION FOR SEQ ID NO:15:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:15:

GGAAAATTTT    10

(2) INFORMATION FOR SEQ ID NO:16:

(i) SEQUENCE CHARACTERISTICS:
       (A) LENGTH: 10 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:16:

GGAAAAACTG    10

(2) INFORMATION FOR SEQ ID NO:17:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:17:

TACATTGGAA AATTTTATTA CAC    23

(2) INFORMATION FOR SEQ ID NO:18:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:18:

GGAGGAAAAA CTGTTTCATA CAGAAGGCGT    30

NUCLEAR FACTORS AND BINDING ASSAYS

This is a division of application Ser. No. 08/396,479 filed Mar. 02, 1995, now U.S. Pat. No. 5,612,455 which is a continuation-in-part application of Ser. No. 08/270,653 filed on Jul. 5, 1994, now abandoned.

INTRODUCTION

1. Field of the Invention

The field of this invention is human transcription factors of activated T-cells.

2. Background

Identifying and developing new pharmaceuticals is a multibillion dollar industry in the U.S. alone. Gene specific transcription factors provide a promising class of targets for novel therapeutics directed to these and other human diseases. Urgently needed are efficient methods of identifying pharmacological agents or drugs which are active at the level of gene transcription. If amenable to automated, cost-effective, high throughput drug screening, such methods would have immediate application in a broad range of domestic and international pharmaceutical and biotechnology drug development programs.

Immunosuppression is therapeutically desirable in a wide variety of circumstances including transplantation, allergy and other forms of hypersensitivity, autoimmunity, etc. Cyclosporin, a widely used drug for effecting immunosuppression, is believed to act by inhibiting a calcineurin, a phosphatase which activates certain nuclear factors of activated T-cells (NFATs). However, because of side effects and toxicity, clinical indications of cyclosporin (and the more recently developed FK506) are limited.

Accordingly, it is desired to identify agents which more specifically interfere with the function of hNFATs. Unfortunately, the reagents necessary for the development of high-throughput screening assays for such therapeutics are unavailable.

3. Relevant Literature

Nolan (Jun. 17, 1994) Cell 77, 1–20 provides a recent review and commentary on molecular interactions of hNFAT proteins. Northrop et at. (Jun. 9, 1994) Nature 369, 497–502 report the cloning of a cDNA encoding human NFATc. McCaffrey et al. (Oct. 29, 1993) Science 262, 750–754 report the cloning of a fragment of a gene encoding a murine NFATp$_1$.

SUMMARY OF THE INVENTION

The invention provides methods and compositions for identifying lead compounds and pharmacological agents useful in the diagnosis or treatment of disease associated with the expression of one or more genes modulated by a transcription complex containing a human nuclear factor of activated T-cells (hNFAT). Several forms of hNFAT are provided including hNFATs designated hNFATp$_1$, hNFATp$_2$, hNFATc, hNFAT3, hNFAT4a, hNFAT4b and hNFAT4c. The invention also provides isolated nucleic acid encoding the subject hNFATs, vectors and cells comprising such nucleic acids, and methods of recombinantly producing polypeptides comprising hNFAT. The invention also provides hNFAT-specific binding reagents such as hNFAT-specific antibodies.

Methods using the disclosed hNFATs in drug development programs involve combining a selected hNFAT with a natural intracellular hNFAT binding target and a candidate pharmacological agent. Natural intracellular binding targets include transcription factors, such as AP1 proteins and nucleic acids encoding a hNFAT binding sequence. The resultant mixture is incubated under conditions whereby, but for the presence of the candidate pharmacological agent, the hNFAT selectively binds the target. Then the presence or absence of selective binding between the hNFAT and target is detected. A wide variety of alternative embodiments of the general methods using hNFATs are disclosed. The methods are particularly suited to high-throughput screening where one or more steps are performed by a computer controlled electromechanical robot comprising an axial rotatable arm and the solid substrate is a portion of a well of a microtiter plate.

| | | hNFAT SEQ ID NOS: |
|---|---|---|
| hNFATp$_1$ | cDNA | SEQ ID NO: 1 |
| hNFATp$_1$ | protein | SEQ ID NO: 2 |
| hNFATp$_2$ | cDNA | SEQ ID NO: 1, bases 1–356 and 868–3478 |
| hNFATp$_2$ | protein | SEQ ID NO: 2, residues 220–921 |
| hNFATc | cDNA | SEQ ID NO: 3 |
| hNFATc | protein | SEQ ID NO: 4 |
| hNFAT3 | cDNA | SEQ ID NO: 5 |
| hNFAT3 | protein | SEQ ID NO: 6 |
| hNFAT4a | cDNA | SEQ ID NO: 7 |
| hNFAT4a | protein | SEQ ID NO: 8 |
| hNFAT4b | cDNA | SEQ ID NO: 9 |
| hNFAT4b | protein | SEQ ID NO: 10 |
| hNFAT4c | cDNA | SEQ ID NO: 11 |
| hNFAT4c | protein | SEQ ID NO: 12 |

DETAILED DESCRIPTION OF THE INVENTION

The invention provides methods and compositions relating to human NFATs. The subject hNFATs include regulators of cytokine gene expression that modulate immune system function. As such, hNFATs and HNFAT-encoding nucleic acids provide important targets for therapeutic intervention.

hNFATs derive from human cells, comprise invariant hNFAT rel domain peptides (see, Table 1)and share at least 50% pair-wise rel sequence identity with each of the disclosed hNFAT sequences. Invariant hNFAT rel domain peptides include from the N-terminal end of the rel domain, HHRAHYETEGSRGAVKA (SEQ ID NO:2, residues 419–435), PHAFYQVHRITGK (SEQ ID NO:2, residues 470–482), IDCAGILKLRN (SEQ ID NO:2, residues 513–523), DIELRKGETDIGRKNTRVRLVFRVHX$_1$P (SEQ ID NO: 13), and PX$_2$ECSQRSAX$_3$ELP (SEQ ID NO: 14), where each X$_1$ and X$_2$ is hydrophobic residue such as valine or isoleucine, and X$_3$ is any residue, but preferably glutamine or histidine.

TABLE 1 hNFAT rel domains
NFATp (SEQ ID NO: 2, residues 388–678)
NFATc (SEQ ID NO: 4, residues 406–697)
NFAT3 (SEQ ID NO: 6, residues 397–686)
NFAT4b/c (SEQ ID NO: 10, residues 411–700)

| | | |
|---|---|---|
| NFATp    | IPVTASLPPLEWPLSSQSGSYELRIEVQPKPHHRAHYETEGSRGAVKAPT | 50 |
| NFATc    | SYMSPTLPALDWQLPSHSGPYELRIEVQPKSHHRAHYETEGSRGAVKASA | 50 |
| NFAT3    | IFRTSALPPLDWPLPSQYEQLELRIEVQPRAHHRAHYETEGSRGAVKAAP | 50 |
| NFAT4b/c | IFRTSSLPPLDWPLPAHPGQCELKIEVQPKTHHRAHYETEGSRGAVKAST | 50 |
| NFATp    | GGHPVVQLHGYMENKPLGLQIFIGTADERILKPHAFYQVHRITGKTVTTT | 100 |
| NFATc    | GGHPIVQLHGYLENEPLMLQLFIGTADDRLLRPHAFYQVHRITGKTVSTT | 100 |
| NFAT3    | GGHPVVKLLGYS-EKPLTLQMFIGTADERNLRPHAFYQVHRITGKMVATA | 99 |
| NFAT4b/c | GGHPVVKLLGYN-EKPINLQMFIGTADDRYLRPHAFYQVHRITGKTVATA | 99 |
| NFATp    | SYEKIVGNTKVLEIPLEPKNNMRATIDCAGILKLRNADIELRKGETDIGR | 150 |
| NFATc    | SHEAILSNTKVLEIPLLPENSMRAVIDCAGILKLRNSDIELRKGETDIGR | 150 |
| NFAT3    | SYEAVVSGTKVLEMTLLPENNMAANIDCAGILKLRNSDIELRKGETDIGR | 149 |
| NFAT4b/c | SQEIIIASTKVLEIPLLPENNMSASIDCAGILKLRNSDIELRKGETDIGR | 149 |
| NFATp    | KNTRVRLVFRVHIPESSGRIVSLQTASNPIECSQRSAHELPMVERQDTDS | 200 |
| NFATc    | KNTRVRLVFRVHVPQPSGRTLSLQVASNPIECSQRSAQELPLVEKQSTDS | 200 |
| NFAT3    | KNTRVRLVFRVHVPQGGGKVVSVQAASVPIECSQRSAQELPQVEAYSPSA | 199 |
| NFAT4b/c | KNTRVRLVFRVHIPQPSGKVLSLQIASIPVECSQRSAQELPHIEKYSINS | 199 |
| NFATp    | CLVYGGQQMILTGQNFTSESKVVFTEKTTDGQQIWEMEATVDKDKSQPNM | 250 |
| NFATc    | YPVVGGKKMVLSGHNFLQDSKVIFVEKAPDGHHVWEMEAKTDRDLCKPNS | 250 |
| NFAT3    | CSVRGGEELVLTGSNFLPDSKVVFIERGPDGKLQWEEEATVNRLQSNEVT | 249 |
| NFAT4b/c | CSVNGGHEMVVTGSNFLPESKIIFLEKGQDGRPQWEVEGKIIREKCQGAH | 249 |
| NFATp    | LFVEIPEYRNKHIRTPVKVNFYVINGKRKRSQPQHFTYHPV | 291 |
| NFATc    | LVVEIPPFRNQRITSPVHVSFYVCNGKRKRSQYQRFTYLPA | 291 |
| NFAT3    | LTLTVPEYSNKRVSRPVQVYFYVSNGRRKRSPTQSFRFLPV | 290 |
| NFAT4b/c | IVLEVPPYHNPAVTAAVQVHFYLCNGKRKKSQSQRFTYTPV | 290 |

In addition to the shared rel domains, some hNFATs have smaller regions of sequence similarity on the terminal side of the rel domains. For example, the amino terminal regions of hNFAT 4a, 4b and 4c and hNFATc have several regions of similarity (Table 2). The two largest regions (designated regions A and B in Table 2) contain 23 of 41 and 24 of 45 identical amino acids between the two proteins. hNFATp and hNFAT3 also have similarity to other hNFAT proteins in this region (Table 2). The homology between hNFAT3 and hNFAT 4a, 4b and 4c extends about 25 amino acids upstream of the rel region (designated region C in Table 2).

sequences and the 50% pair-wise rel domain identity, cDNAs of hNFAT transcripts typically share substantially overall sequence identity with one or more of the disclosed hNFAT sequences.

The subject hNFAT fragments have one or more hNFAT-specific binding affinities, including the ability to specifically bind at least one natural human intracellular hNFAT-specific binding target or a hNFAT-specific binding agent such as a hNFAT-specific antibody or a hNFAT-specific binding agent identified in assays such as described below. Accordingly, the specificity of hNFAT fragment specific

TABLE 2 hNFAT regions 5' to the rel domain

| | | | |
|---|---|---|---|
| A | NFATc    | PSTATLSLPSLEAYRDPS-CLSPASSLSSRSCNSEASSYES | 195 |
|   | NFAT4a   | PSRDHLYLPLEPSYRESSLSPSPASSISSRSWFSDASSCES | 189 |
|   | NFATc (SEQ ID NO: 4, residues 152–191) | | |
|   | NFAT4a (SEQ ID NO: 8, residues 144–184) | | |
| B | NFATc    | SPQHSPSTSPRASVTEESWLGAR-----SSRPASPCNKRKYSLNG | 272 |
|   | NFAT4a   | SPRQSPCHSPRSSVTDENWLSPRPASGPSSRPTSPCGKRRSSAEV | 281 |
|   | NFATc (SEQ ID NO: 4, residues 233–272) | | |
|   | NFAT4a (SEQ ID NO: 8, residues 236–281) | | |
|   | NFATc    | SSRPASPCNKRKYSLNG | 272 |
|   | NFAT3    | SPRPASPCGKRRYSSSG | 275 |
|   | NFATc (SEQ ID NO: 4, residues 256–272) | | |
|   | NFAT3 (SEQ ID NO: 6, residues 259–275) | | |
|   | NFATc    | SPQHSPSTSPRASVTEESWLGARSSRP | 272 |
|   | NFATp    | SPRTSPIMSPRTSLAEDSCLGRHSPVP | 239 |
|   | NFATc (SEQ ID NO: 4, residues 233–259) | | |
|   | NFATp (SEQ ID NO: 2, residues 213–239) | | |
| C | NFAT3    | RKEVAGMDYLAVPSPLAWSKARIGGHSP | 396 |
|   | NFAT4a   | KKDSCGDQFLSVPSPFTWSKPKPG-HTP | 410 |
|   | NFAT3 (SEQ ID NO: 6, residues 369–396) | | |
|   | NFAT4a (SEQ ID NO: 8, residues 384–410) | | |

Nucleic acids encoding hNFATs may be isolated from human cells by screening cDNA libraries for human immune cells with probes or PCR primers derived from the disclosed hNFAT genes. In addition to the invariant hNFAT rel binding agents is confirmed by ensuring non-cross-reactivity with other NFATs. Furthermore, preferred hNFAT fragments are capable of eliciting an antibody capable of specifically binding an hNFAT. Methods for making immunogenic peptides through the use of conjugates, adjuvants, etc. and methods for eliciting antibodies, e.g. immunizing rabbits, are well known.

Exemplary natural intracellular binding targets include nucleic acids which comprise one or more hNFAT DNA binding sites. Functional hNFAT binding sites have been found in the promoters or enhancers of several different cytokine genes including IL-2, IL-4, IL-3, GM-CSF, and TNF-a and are often located next to AP-1 binding sites, which are recognized by members of the fos and jun families of transcription factors. Typically, the AP-1 binding sites adjacent to hNFAT sites are low affinity sites, and AP-1 proteins cannot bind them independently. However, many NF-AT and AP-1 protein combinations are capable of cooperatively binding to DNA. Furthermore, cell-type specificity of cytokine gene transcription is often controlled, at least in part, by the combinations of hNFAT and AP-1 proteins present in those cells. For example, there are different classes of T cells that secrete different sets of cytokines: e.g. TH1 cells produce IL-2 and IFN-g, while TH2 cells produce IL-4, IL-5, and IL-6. hNFAT binding sites are involved in the regulation of both TH1 and TH2 cytokines. Further, differential expression of the cytokine gene in T cell subsets is controlled the combinatorial interactions of hNFAT and AP-1 proteins.

In addition to DNA binding sites and other transcription factors such as AP1, other natural intracellular binding targets include cytoplasmic proteins such as ankyrin repeat containing hNFAT inhibitors, protein serine/threonine kinases, etc., and fragments of such targets which are capable of hNFAT-specific binding. Other natural hNFAT binding targets are readily identified by screening cells, membranes and cellular extracts and fractions with the disclosed materials and methods and by other methods known in the art. For example, two-hybrid screening using hNFAT fragments are used to identify intracellular targets which specifically bind such fragments. Preferred hNFAT fragments retain the ability to specifically bind at least one of an hNFAT DNA binding site and can preferably cooperatively bind with AP 1. Convenient ways to verify the ability of a given hNFAT fragment to specifically bind such targets include in vitro labelled binding assays such as described below, and EMSAs.

A wide variety of molecular and biochemical methods are available for generating and expressing hNFAT fragments, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, New York, N.Y., 1992) or that are otherwise known in the art. For example, hNFAT or fragments thereof may be obtained by chemical synthesis, expression in bacteria such as E. coli and eukaryotes such as yeast or vaccinia or baculovirus-based expression systems, etc., depending on the size, nature and quantity of the hNFAT or fragment. The subject hNFAT fragments are of length sufficient to provide a novel peptide. As used herein, such peptides are at least 5, usually at least about 6, more usually at least about 8, most usually at least about 10 amino acids. hNFAT fragments may be present in a free state or bound to other components such as blocking groups to chemically insulate reactive groups (e.g. amines, carboxyls, etc.) of the peptide, fusion peptides or polypeptides (i.e. the peptide may be present as a portion of a larger polypeptide), etc.

The subject hNFAT fragments maintain binding affinity of not less than six, preferably not less than four, more preferably not less than two orders of magnitude less than the binding equilibrium constant of a full-length native hNFAT to the binding target under similar conditions. Particular hNFAT fragments or deletion mutants are shown to function in a dominant-negative fashion. Such fragments provide therapeutic agents, e.g. when delivered by intracellular immunization—transfection of susceptible cells with nucleic acids encoding such mutants.

The claimed hNFAT and hNFAT fragments are isolated, partially pure or pure and are typically recombinantly produced. As used herein, an "isolated" peptide is unaccompanied by at least some of the material with which it is associated in its natural state and constitutes at least about 0.5%, preferably at least about 2%, and more preferably at least about 5% by weight of the total protein (including peptide) in a given sample; a partially pure peptide constitutes at least about 10%, preferably at least about 30%, and more preferably at least about 60% by weight of the total protein in a given sample; and a pure peptide constitutes at least about 70%, preferably at least about 90%, and more preferably at least about 95 % by weight of the total protein in a given sample.

Preferred hNFAT fragments comprise at least a functional portion of the rel domain. There are several different biochemical functions that are mediated by the rel and hNFAT rel-similarity domains: DNA binding, dimerization, interaction with B-zip proteins, interaction with inhibitor proteins, and nuclear localization. Other rel family proteins have been shown to physically interact with AP-1 (fos and jun) proteins (Stein et al., EMBO J. 12, 1993). The rel homology domain is necessary for this interaction and the B-zip region of the AP-1 proteins is involved in this protein-protein interaction. The specificity in the ability of hNFAT and AP-1 family members to interact is related to the tissue specific and cell type specific regulation of gene expression governed by these proteins. The rel and rel-similarity domains also interact with members of the I-kB family of inhibitor proteins including I-kB-like ankyrin repeat proteins (reviewed in Beg and Baldwin, Genes and Dev., 1993). The C-terminal half or the rel domain is involved the interaction with I-kB. There are 5 related I-kB-like proteins which are characterized by having multiple copies of a 33 amino acid sequence motif called the ankyrin repeat.

The invention provides hNFAT-specific binding agents, methods of identifying and making such agents, and their use in diagnosis, therapy and pharmaceutical development. For example, hNFAT-specific agents are useful in a variety of diagnostic applications, especially where disease or disease prognosis is associated with immune disfunction resulting from improper expression of hNFAT. Novel hNFAT-specific binding agents include hNFAT-specific antibodies and other natural intracellular binding agents identified with assays such as one- and two-hybrid screens; non-natural intracellular binding agents identified in screens of chemical libraries, etc.

Generally, hNFAT-specificity of the binding target is shown by binding equilibrium constants. Such targets are capable of selectively binding a hNFAT, i.e. with an equilibrium constant at least about $10^4$ $M^{-1}$, preferably at least about $10^6$ $M^{-1}$, more preferably at least about $10^8$ $M^{-1}$. A wide variety of cell-based and cell-free assays may be used to demonstrate hNFAT-specific binding. Cell based assays include one and two-hybrid screens, mediating or competitively inhibiting hNFAT-mediated transcription, etc. Preferred are rapid in vitro, cell-free assays such as mediating or inhibiting hNFAT-protein (e.g. hNFAT-AP1 binding), hNFAT-nucleic acid binding, immunoassays, etc. Other useful screening assays for hNFAT/hNFAT fragment-target binding include fluorescence resonance energy transfer (FRET), electrophoretic mobility shift analysis (EMSA), etc.

The invention also provides nucleic acids encoding the subject hNFAT and hNFAT fragments, which nucleic acids may be part of hNFAT-expression vectors and may be incorporated into recombinant cells for expression and screening, transgenic animals for functional studies (e.g. the efficacy of candidate drugs for disease associated with expression of a hNFAT), etc. In addition, the invention provides nucleic acids sharing substantial sequence similarity with that of one or more wild-type hNFAT nucleic acids. Substantially identical or homologous nucleic acid sequences hybridize to their respective complements under high stringency conditions, for example, at 55° C. and hybridization buffer comprising 50% formamide in 0.9M saline/0.09M sodium citrate (SSC) buffer and remain bound when subject to washing at 55° C. with the SSC/formamide buffer. Where the sequences diverge, the differences are preferably silent, i.e. or a nucleotide change providing a redundant codon, or conservative, i.e. a nucleotide change providing a conservative amino acid substitution.

The subject nucleic acids find a wide variety of applications including use as hybridization probes, PCR primers, therapeutic nucleic acids, etc. for use in detecting the presence of hNFAT genes and gene transcripts, for detecting or amplifying nucleic acids with substantial sequence similarity such as hNFAT homology and structural analogs, and for gene therapy applications. Given the subject probes, materials and methods for probing cDNA and genetic libraries and recovering homology are known in the art. Preferred libraries are derived from human immune cells, especially cDNA libraries from differentiated and activated human lymphoid cells. In one application, the subject nucleic acids find use as hybridization probes for identifying hNFAT cDNA homologs with substantial sequence similarity. These homologs in turn provide additional hNFATs and hNFAT fragments for use in binding assays and therapy as described herein. hNFAT encoding nucleic acids also find applications in gene therapy. For example, nucleic acids encoding dominant-negative hNFAT mutants are cloned into a virus and the virus used to transfect and confer disease resistance to the transfected cells.

Therapeutic hNFAT nucleic acids are used to modulate, usually reduce, cellular expression or intracellular concentration or availability of active hNFAT. These nucleic acids are typically antisense: single-stranded sequences comprising complements of the disclosed hNFAT nucleic acids. Antisense modulation of hNFAT expression may employ hNFAT antisense nucleic acids operably linked to gene regulatory sequences. Cell are transfected with a vector comprising an hNFAT sequence with a promoter sequence oriented such that transcription of the gene yields an antisense transcript capable of binding to endogenous hNFAT encoding mRNA. Transcription of the antisense nucleic acid may be constitutive or inducible and the vector may provide for stable extrachromosomal maintenance or integration. Alternatively, single-stranded antisense nucleic acids that bind to genomic DNA or mRNA encoding a hNFAT or hNFAT fragment may be administered to the target cell, in or temporarily isolated from a host, at a concentration that results in a substantial reduction in hNFAT expression. For gene therapy involving the transfusion of hNFAT transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The subject nucleic acids are often recombinant, meaning they comprise a sequence joined to a nucleotide other than that which it is joined to on a natural chromosome. An isolated nucleic acid constitutes at least about 0.5 %, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

The invention provides efficient methods of identifying pharmacological agents or drugs which are active at the level of hNFAT modulatable cellular function, particularly hNFAT mediated interleukin signal transduction. Generally, these screening methods involve assaying for compounds which interfere with hNFAT activity such as hNFAT-AP1 binding, hNFAT-DNA binding, etc. The methods are amenable to automated, cost-effective high throughput drug screening and have immediate application in a broad range of domestic and international pharmaceutical and biotechnology drug development programs.

Target therapeutic indications are limited only in that the target cellular function (e.g. gene expression) be subject to modulation, usually inhibition, by disruption of the formation of a complex (e.g. transcription complex) comprising a hNFAT or hNFAT fragment and one or more natural hNFAT intracellular binding targets. Since a wide variety of genes are subject to hNFAT regulated gene transcription, target indications may include infection, metabolic disease, genetic disease, cell growth and regulatory disfunction, such as neoplasia, inflammation, hypersensitivity, etc. Frequently, the target indication is related to either immune dysfunction or selective immune suppression.

A wide variety of assays for binding agents are provided including labelled in vitro protein-protein and protein-DNA binding assay, electrophoretic mobility shift assays, immunoassays for protein binding or transcription complex formation, cell based assays such as one, two and three hybrid screens, expression assays such as transcription assays, etc. For example, three-hybrid screens are used to rapidly examine the effect of transfected nucleic acids, which may, for example, encode combinatorial peptide libraries or antisense molecules, on the intracellular binding of hNFAT or hNFAT fragments to intracellular hNFAT targets. Convenient reagents for such assays (e.g. GAL4 fusion partners) are known in the art.

hNFAT or hNFAT fragments used in the methods are usually added in an isolated, partially pure or pure form and are typically recombinantly produced. The hNFAT or fragment may be part of a fusion product with another peptide or polypeptide, e.g. a polypeptide that is capable of providing or enhancing protein—protein binding, sequence-specific nucleic acid binding or stability under assay conditions (e.g. a tag for detection or anchoring).

The assay mixtures comprise at least a portion of a natural intracellular hNFAT binding target such as AP1 or a nucleic acid comprising a sequence which shares sufficient sequence similarity with a gene or gene regulatory region to which the native hNFAT naturally binds to provide sequence-specific binding of the hNFAT or hNFAT fragment. Such a nucleic acid may further comprise one or more sequences which facilitate the binding of a second transcription factor or fragment thereof which cooperatively binds the nucleic acid with the hNFAT (i.e. at least one increases the affinity or specificity of the DNA binding of the other). While native binding targets may be used, it is frequently preferred to use portions (e.g. peptides, nucleic acid fragments) or analogs (i.e. agents which mimic the hNFAT binding properties of the natural binding target for the purposes of the assay) thereof so long as the portion provides binding affinity and avidity to the hNFAT conveniently measurable in the assay. Binding sequences for other transcription factors may be found in sources such as the Transcription Factor Database of the National Center for Biotechnology Information at the National Library for Medicine, in Faisst and Meyer (1991) Nucleic Acids Research 20, 3–26, and others known to those skilled in this art.

Where used, the nucleic acid portion bound by the peptide (s) may be continuous or segmented and is usually linear and double-stranded DNA, though circular plasmids or other nucleic acids or structural analogs may be substituted so long as hNFAT sequence-specific binding is retained. In some applications, supercoiled DNA provides optimal sequence-specific binding and is preferred. The nucleic acid may be of arty length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp. Additional nucleotides may be used to provide structure which enhances or decreased binding or stability, etc. For example, combinatorial DNA binding can be effected by including two or more DNA binding sites for different or the same transcription factor on the oligonucleotide. This allows for the study of cooperative or synergistic DNA binding of two or more factors. In addition, the nucleic acid can comprise a cassette into which transcription factor binding sites are conveniently spliced for use in the subject assays.

The assay mixture also comprises a candidate pharmacological agent. Generally a plurality of assay mixtures are run in parallel with different agent concentrations to obtain a differential response to the various concentrations. Typically, one of these concentrations serves as a negative control, i.e. at zero concentration or below the limits of assay detection. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of the functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like. Where the agent is or is encoded by a transfected nucleic acid, said nucleic acid is typically DNA or RNA.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the hNFAT specifically binds the cellular binding target, portion or analog. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of specific binding between the hNFAT and one or more binding targets is detected by any convenient way. For cell-free binding type assays, a separation step is often used to separate bound from unbound components. The separation step may be accomplished in a variety of ways. Conveniently, at least one of the components is immobilized on a solid substrate which may be any solid from which the unbound components may be conveniently separated. The solid substrate may be made of a wide variety of materials and in a wide variety of shapes, e.g. microtiter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. For cell based assays such as one, two, and three hybrid screens, the transcript resulting from hNFAT-target binding usually encodes a directly or indirectly detectable product (e.g.

galactosidase activity, luciferase activity, etc.). For cell-free binding assays, one of the components usually comprises or is coupled to a label. A wide variety of labels may be employed—essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. The methods are particularly suited to automated high throughput drug screening. Candidate agents shown to inhibit hNFAT-target binding or transcription complex formation provide valuable reagents to the pharmaceutical industries for animal and human trials.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microtiter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microliter plates. Of course, useful agents are identified with a range of other assays (e.g. gel shifts, etc.) employing the subject hNFAT and hNFAT fragments.

The subject hNFAT and hNFAT fragments and nucleic acids provide a wide variety of uses in addition to the in vitro binding assays described above. For example, cell-based assays are provided which involve transfecting a T-cell expressing cell with an hNFAT inducible antigen receptor expressing cell with an hNFAT inducible reporter such as luciferase. Agents which modulate hNFAT mediated cell function are then detected through a change in the reporter.

The following examples are offered by way of illustration and not by way of limitation.

EXPERIMENTAL

Investigation of the antigen inducible expression of the IL-2 gene led to the discovery of the regulatory transcription factor NFAT (Nuclear Factor of Activated T cells) (Durand et al. 1988; Shaw et al. 1988). Like several other transcription factors involved in mediating signal transduction, the activity of NFAT is regulated by subcellular localization. In resting T cells NFAT activity is restricted to cytoplasm; stimulation of the T cell receptor leads to translocation of NFAT to the nucleus. Movement of NFAT to the nucleus is dependent on the activation of the calcium-regulated phosphatase calcineurin (Clipstone and Crabtree 1992). The immunosuppressive drugs cyclosporin and FK506 inhibit the activity of calcineurin, and thereby prevent the nuclear localization of NFAT and subsequent activation of cytokine gene expression (reviewed in (Schreiber and Crabtree 1992).

Activation of the T cell antigen receptor induces two signalling pathways required for IL-2 induction, one is the cyclosporin-sensitive, calcium-dependent pathway and the other relies on the activation of protein kinase C (PKC). Antigenic stimulation of these pathways can be mimicked by treating cells with a calcium ionophore and a phorbol ester. The PKC-inducible activity was found to be mediated by fos and jun proteins (Jain et al. 1992; Northrop et al. 1993). The NFAT binding site in the IL-2 promoter is adjacent to a weak binding site for AP-1 proteins, and NFAT and AP-1 proteins bind cooperatively to this composite element (Jain et al. 1993; Northrop et al. 1993). The transcriptional activation mediated by AP-1 proteins through this site appears to be critical for IL-2 expression in activated T cells. There are several different combinations of fos and jun family members that can interact with NFAT to bind DNA (Boise et al. 1993; Northrop et al. 1993; Jain et al. 1994; Yaseen et al. 1994). Therefore, the composition of the AP-1 complex that interacts with NFAT may vary in different cell types and different stages of T cell activation. NFAT was originally reported to be a T cell specific transcription factor critical for the restricted expression of IL-2 (Shaw et al. 1988). More recently, NFAT activity was detected in B cells (Brabletz et al. 1991; Yaseen et al. 1993; Choi et al. 1994; Venkataraman et al. 1994). This is consistent with the finding that, in transgenic mice, the major sites of expression of a reporter gene regulated by the IL-2 NFAT/AP-1 site are activated T and B cells (Verweij et at. 1990).

In addition to IL-2, NFAT sites have been discovered in the promoters of several other cytokine genes, including IL-4 (Chuvpilo et al. 1993; Szabo et al. 1993; Rooney et al. 1994), IL-3 (Cockerill et al. 1993), GM-CSF (Masuda et al. 1993), and TNF-a (Goldfeld et al. 1993). Thus, it appears that NFAT proteins are involved in the coordinate regulation of many different cytokines in activated lymphocytes. As with IL-2, most of the NFAT sites in other cytokine promoters are composite elements that also contain AP-1 binding sites (Rao, 1994).

Distinct genes encoding NFAT proteins have now been isolated (Jain et al. 1993; McCaffrey et al. 1993; Northrop et al. 1994; Hoey et al., in press). Two of these genes, designated NFATp and NFATc, encode related proteins that are highly similar to each other within a 290 amino acid domain. This NFAT homology region shares weak sequence similarity with the DNA binding and dimerization domain of the rel family of transcription factors (reviewed in (Nolan 1994). There is evidence that both NFATp and NFATc may be involved in mediating transcriptional regulation in activated T cells. For example, NFATp forms a specific complex on DNA with fos and jun that activates transcription in vitro (McCaffrey et al. 1993). NFATc has been shown to activate IL-2 expression by a cotransfection assay in T cells (Northrop et al. 1994). Furthermore, both proteins appears to be modified by calcineurin (Jain et al 1993; Northrop et al. 1994). In addition to NFATp and NFATc, we have isolated two new members of the human NFAT gene family. We have used these clones to examine the tissue distribution of the different NFAT genes. We have also expressed and purified the DNA binding domains of the NFAT family proteins and investigated their biochemical activities.

Results

1. Cloning of Human NFAT Genes cDNA libraries were prepared from Jurkat T cells and human peripheral blood lymphocytes, and screened using a probe derived from the rel similarity region of the murine NFATp gene (McCaffrey et al. 1993). Cross-hybridizing clones were isolated, sequenced, and determined to be derived from 4 distinct genes.

One of the genes isolated in this study is related to the murine NFATp gene (McCaffrey et al. 1993), and another is identical to the NFATc gene (Northrop et al. 1994). We have isolated two classes of NFATp cDNAs which are the result of alternative splicing upstream of the rel domain. One form is similar to the cDNA reported by McCaffrey et al., while the other is alternatively spliced downstream of the rel similarity region; in particular, this form is missing an exon encoding the region near the N-terminus of the protein (SEQ ID NO: 1, base pairs 357–867) and has a different initiating methionine (SEQ ID NO: 1, base pairs 880–882).

In addition to these previously identified genes, we cloned two novel members of the NFAT gene family, hereby designated as NFAT3 and NFAT4. The NFAT3 sequence was obtained from three overlapping cDNAs spanning 2880 bp, and deduced to encode a protein of 902 amino acids. We obtained three classes of NFAT4 cDNAs that resulted from alternative splicing downstream of the rel homology domain. These three types of cDNAs encode proteins that vary in sequence and length at their C-terminal ends. The three forms are designated NFAT4a, NFAT4b, and NFAT4c. The positions of splice junctions in the coding regions are after proline 699 in NFAT4a and after valine 700 and proline 716 in NFAT4b and NFAT4c.

All of the NFAT genes are at least 65% identical to each other within a 290 amino acid domain. This domain is related to the DNA binding and dimerization domain of the rel family of transcription factors (Nolan 1994; Northrop et al. 1994). Among the different NFAT genes, the N-terminal and central portions of the rel similarity domain are more highly conserved than the C-terminus.

Aside from the strikingly similar rel domains shared by all four NFAT genes, the NFAT family members have smaller regions of sequence similarity on the amino terminal side of the rel domains. The amino terminal regions of NFAT4 and NFATc have several regions of significant similarity. The two largest regions contain 23 of 41 and 24 of 45 identical amino acids between the two proteins. Both of these regions are rich in serine and proline residues. NFATp and NFAT3 also have some similarity to the other NFAT proteins in this region, although it is less extensive than that shared between NFAT4 and NFATc. The homology between NFAT3 and NFAT4 extends about 25 amino acids upstream of the rel similarity region.

2. Expression Patterns of the NFAT Genes

On the basis of previous reports, expression of NFAT genes was expected to be restricted to lymphocytes (Shaw et al. 1988; Verweij et al. 1990; McCaffrey et al. 1993; Northrop et al. 1994). The expression of each NFAT gene was tested by Northern blot using RNA from sixteen different human tissues. For NFATp, expression of an mRNA approximately 7.5 kb was detected in almost all human tissues. The expression was slightly higher in PBLs and placenta. NFATc expression was also detected at a low level in several different tissues. The NFATc probe hybridized to two bands of approximately 2.7 and 4.5 kb. Surprisingly, the 4.5 kb NFATc transcript was strongly expressed in skeletal muscle. The 2.7 kb mRNA appears to correspond to the previously described NFATc clone (Northrop et al. 1994).

NFAT3 exhibited a very complicated expression pattern with at least 3 major RNA bands between 3 and 5 kb. The major sites of NFAT3 expression were observed outside the immune system. NFAT3 was highly expressed in placenta, lung, kidney, testis and ovary. In contrast, NFAT3 expression was very weak in spleen and thymus and undetectable in PBLs.

NFAT4 was expressed predominately as a 6.5 kb message. Like NFATc it was strongly expressed in skeletal muscle. NFAT4 also displayed relatively high expression in thymus. The probe for the NFAT4 northerns contained the 3' half of the NFAT homology region as well as downstream regions from the NFAT4c class of cDNA. This probe should hybridize to all three classes of NFAT4 transcripts. Only one form is detected in the Northern blots, suggesting that the 4c class is the most abundant transcript.

These results indicate that each of the NFAT genes is expressed in a distinct tissue-specific pattern. Furthermore, none of the NFAT genes are restricted to lymphocytes.

3. DNA Binding Activity of the NFAT Proteins

The rel similarity regions along with a small amount of flanking sequences of each of the four classes of NFAT proteins were expressed in *E. coli*. Each of the 4 proteins was well expressed and soluble. The proteins were purified to near homogeneity by DNA affinity chromatography (Kadonaga and Tjian 1986). The binding site used for purification was a high affinity NFAT site derived from the IL-4 promoter with the core binding sequence GGAAAATTTT (SEQ ID NO: 15) (Rooney et al. 1994).

The binding specificities of the NFAT proteins were tested on two known functional binding sites, the IL-4 promoter NFAT site and the NFAT binding site in the distal antigen response element from the IL-2 promoter (Durand et al. 1988; Shaw et al. 1988). All the proteins were able to bind the IL-4 promoter site. NFATp, NFATc, and NFAT3 recognized this sequence with very similar affinity, while NFAT4 bound this sequence with lower affinity (>10-fold) than the other three proteins in this assay. NFAT4 protein may have a different optimum binding sequence than the other NFAT proteins.

The same amounts of the four NFAT proteins were tested on the NFAT binding site from the IL-2 promoter. This NFAT site (GGAAAAACTG) (SEQ ID NO:16) has three differences relative to the IL-4 site which make it a weaker site for all four NFAT proteins. The NFAT proteins differ in their ability to recognize this site independently. NFATp had the highest relative affinity for the IL-2 binding site, while NFATc and NFAT3 bound weakly to this site and NFAT4 binding was not detectable in this assay.

The IL-2 NFAT site is part of a composite element that is adjacent to a weak AP-1 site (TGTTTCA) (Jain et al. 1992; Northrop et al. 1993). To determine if there were any differences in the ability of NFAT proteins to interact with AP-1, the four NFAT proteins were tested with AP-1 for binding to the IL-2 site. When tested alone all the NFAT proteins, as well as the AP-1 proteins, bound relatively weakly to the IL-2 composite element. The combination of c-jun and fra1 with each of the four NFAT proteins resulted in highly cooperative DNA binding. In the presence of the AP-1 protein the four NFAT proteins bound to the IL-2 site with very similar affinity. In all cases, jun homodimers were not as effective as jun-fra1 heterodimers in promoting cooperative binding in the gel shift assay. These results indicate that the DNA binding and protein interaction specificity of the NFAT proteins are very similar. Indeed, the interactions of the four NFAT proteins with these AP-1 proteins appear to be identical. NFAT4 did not bind independently to this site, but recognized this site with the same affinity as the other NFAT proteins in the presence of AP-1.

4. Transcriptional Activation by the NFAT Poteins

Having established that the DNA binding properties of the four NFAT proteins are quite similar, we investigated their transcriptional activation potentials. We used a transient transfection assay into Jurkat T cells to measure the ability of the NFAT proteins to activate the IL-2 promoter. The IL-2 promoter was chosen because it is a critical regulatory target for NFAT and has at least two functional NFAT binding sites (Randak et al. 1990). Activation of this promoter by antigenic stimulation can be mimicked by treatment with phorbol esters, such as phorbol 12-myristate 13 acetate (PMA), together with ionomycin, a calcium ionophore.

Each of the four NFAT genes was transfected into Jurkat cells, and their ability to activate the IL-2 promoter was tested with various combinations of PMA and ionomycin. Treatment of the cells with PMA plus ionomycin induced strong activation by the endogenous NFAT proteins in Jurkat cells. Transfection of each of the four of the NFAT genes resulted in an additional stimulation the IL-2 promoter between 4- and 8-fold. Activation of the IL-2 promoter by each of the NFAT proteins was dependent on both PMA and ionomycin.

We also tested the ability of NFAT to activate transcription in COS and HepG2 cells using a synthetic reporter gene consisting three copies of an NFAT/AP-1 composite element. Transfection of each of the four NFAT into HepG2 cells resulted in activation of the reporter gene of at least 20-fold in the presence of PMA and ionomycin. In contrast to Jurkat cells, NFAT3 was more potent than the others in the HepG2 transfections, resulting in 140-fold activation. Another difference between the results of HepG2 and Jurkat cells is that the NFAT proteins appeared to activate transcription in the absence of PMA or calcium ionophore.

In COS cells NFAT3 produced a striking 50-fold activation that was observed independently of PMA and ionomycin treatment. NFAT3 was found to stimulate transcription in COS cells much more strongly than the other proteins.

5. NFAT Proteins are Active as Monomers

There are many similar features of the NFAT and rel families of transcription factors. Rel proteins form homo- and heterodimers in solution, and dimerization is required for DNA binding (reviewed in Baeuerle and Henkel 1994). The C-terminal half of the rel homology domain is thought to be involved in mediating dimerization. Since the similarity between NFAT and the rel families extends throughout the 300 amino acid rel domain, and the rel domain of the NF-kB proteins is sufficient for dimer formation, we expected that the NFAT proteins might also be function as dimers. To test this idea we determined the native masses of the NFAT proteins by gel filtration chromatography and glycerol gradient centrifugation. For these experiments we used the rel similarity regions of NFATp and NFATc that were expressed in *E. coli* and purified by DNA affinity chromatography. The molecular weights of these proteins are 40.4 and 35.6 kD, respectively. As a control we used purified NF-kB p50 protein that is known to exist as a stable dimer in solution (Baeuerle and Baltimore 1989). The p50 protein is 45.8 kD calculated from its amino acid sequence.

On both the gel filtration column and the glycerol gradient, the NFATp and NFATc rel domains migrated at a position close to their actual molecular weight. Under the same conditions, p50 behaved as species that was larger than its monomer molecular weight. The data from the gel filtration column was used to calculate the Stokes radius of each protein, and the S values were determined by glycerol gradient sedimentation. These two properties were used to calculate the apparent molecular size of the proteins (Siegel and Monty 1966; Thompson et al. 1991). The apparent molecular sizes of the NFATp and NFATc rel domains were determined to be 42 kD and 32 kD respectively. These values are close to the monomer molecular weight for both NFAT proteins. As expected, p50 exhibited an apparent molecular size close to that of a dimer.

After determining that NFAT rel domains were monomers in solution, we then considered the possibility that NFAT proteins might form dimers when bound to DNA. To address this question we carried out gel mobility shift assays with two different sized versions of NFATc translated in vitro (Hope and Struhl 1987). The shorter version contains the rel similarity region and a small amount of flanking residues and is referred to as NFATc-309. This construct is equivalent to the one that was expressed in *E. coli*. The larger version, NFATc-589, contains additional N-terminal sequences. When expressed individually in a rabbit reticulocyte lysate both versions of NFATc were active and produced protein-DNA complexes with different mobilities. When the two different NFATc proteins were mixed by co-translation the same protein-DNA complexes were apparent and no intermediate species was detectable, as would be expected if the proteins were forming dimers on the DNA. These results suggest that NFAT proteins are capable of sequence-specific DNA binding as monomers.

Methods

1. Isolation of Human NFAT Clones

Peripheral blood lymphocytes (PBLs) were isolated from 2 units of blood (obtained from Irwin Memorial Blood Bank, San Francisco) by fractionation on sodium metrizoate/polysaccharide (Lymphoprep, Nycomed) gradients. Jurkat T cells were grown in RPMI+10% fetal bovine serum. Total RNA was isolated from Jurkat cells or peripheral blood lymphocytes according to the Guanidinium-HCl method (Chomczynski and Sacchi 1987). Poly-A+RNA was purified using oligo-dT magnetic beads (Promega). Random primed and oligo-dT primed libraries were prepared from both Jurkat and PBL RNA samples. The cDNA libraries were constructed in the vector Lambda ZAPII (Stratagene) according to the protocol supplied by the manufacturer. The cDNA was size selected for greater than 1 kb by electrophoresis a on 5 % polyacrylamide gel prior to ligation. Each library contained approximately $2 \times 10^6$ recombinant clones. Each of the four libraries was screened independently under the same conditions.

The probe for the initial library screen was a 372 bp fragment derived by PCR from the C-terminal half of the rel homology domain of the mouse NFATp gene. This region corresponds to amino acids 370 through 496 in the published mNFATp sequence (McCaffrey et al. 1993). The fragment was labeled by random priming and hybridized in 1M NaCl, 50 mM Tris pH 7.4, 2 mM EDTA, 10× Denhardt's, 0.05% SDS, and 50 mg/ml salmon sperm DNA at 60° C. The filters were washed first in 2× SSC, 0.1% SDS, and then in 1× SSC, 0.1% SDS at 60° C. Hybridizing clones were purified and converted into Bluescript plasmid DNA clones. The DNA sequence was determined using thermal cycle sequencing and the Applied Biosystems 373A sequencer. Approximately 50 clones were isolated from the first set of screens. Sequence analysis and cross-hybridization experiments indicated that these clones were derived from 4 distinct genes. For NFAT4, additional cDNA clones were obtained from a skeletal muscle cDNA library (Stratagene). The 5' ends of the cDNA clones were obtained from a Jurkat cDNA library prepared as described above with gene specific primers for each of the NFAT genes.

2. Northerns

The northern blots with mRNA isolated from human tissues were purchased from Clontech. DNA probes were labeled by random priming and hybridized in 5× SSPE, 10× Denhardt's, 50% formamide, 2% SDS, 100 mg/ml salmon sperm DNA at 42° C. The filters were washed in 2× SSC/0.05% SDS at room temperature, and subsequently in 0.1× SSC/0.1% SDS at 60° C. For NFATp the probe was 1.2 kb cDNA fragment containing the entire rel similarity region of NFATp. For NFATc, the probe was a 291 nucleotide PCR fragment corresponding to the 3' end of rel similarity region (amino acids 597 to 693 (Northrop et al. 1994). For NFATc, a different set of blots was hybridized with a 0.8 kb cDNA fragment located upstream of the rel domain. The two different NFATc probes produced identical results. For NFAT3, the probe was a 0.6 kb fragment located downstream of the rel similarity region corresponding to the region encoding amino acid 720 through the 3' end of the clone. For NFAT4, the probe was a 1.3 kb cDNA fragment corresponding to residue 549 to 963 from the 4c class of cDNAs.

3. Protein Expression and Purification

E. coli expression vectors for each NFAT protein were constructed in the T7 polymerase expression vector pT7-HMK, which has an eight amino acid heart muscle kinase (hmk) site at the N-terminus. NdeI sites were introduced by PCR using mutagenic oligonucleotides in the coding regions upstream of the NFAT rel domains, and these restriction sites were subsequently used for cloning into pT7-HMK. The sizes of the different proteins (without the hmk sequences) are as follows: NFATp, 353 amino acids (the residues homologous to 185 through 537 according to McCaffrey et al. 1993); NFATc, 309 amino acids (amino acids 408 through 716 according to Northrop et al. 1994); NFAT3, 345 amino acids (residues 400 through 744); NFAT4, 316 amino acids (residues 393 through 708).

Proteins were expressed using the T7 polymerase expression system in the strain BL21(DE3) (Studier and Moffat 1986). Expression was induced by addition of 0.4 mM IPTG, and the cultures were shaken for 4 hours at room temperature. The cells were harvested, washed in PBS, resuspended in 0.4M KCl-HEG (25 mM HEPES pH 7.9; 0.1 mM EDTA; 10% glycerol; 0.2% NP-40; 2 mM DTT, 0.2 mM PMSF, 0.2 mM sodium metabisulfite) and lysed by two cycles of freeze- thawing followed by sonication. The lysate was spun in 10 min to remove insoluble material. NFAT proteins were purified from the soluble fractions of the extracts by DNA affinity chromatography (Kadonaga and Tjian 1986). The binding site sequence for the affinity resin was from the IL-4 promoter, TACATTGGAAAATTTTAT-TACAC (SEQ ID NO:17). The DNA was biotinylated on one strand and coupled to avidin agarose beads (Sigma) at a concentration of approximately 1 mg DNA/ml. Approximately 10 mg of E. coli extracts containing the recombinant NFAT proteins were loaded on 1.5 ml DNA columns equilibrated with 0.1M KCl-HEG. The columns were washed successively with 0.1, 0.2, and 0.4M HEG. The specifically bound NFAT proteins were eluted with 1.0M KCl-HEG.

Fra-1 was expressed in E. coli from the vector pET11 (Novagen). The protein was purified from the soluble fraction to approximately 80% homogeneity by fractionation on heparin-sepharose. c-Jun protein was expressed in E. coli and purified from the insoluble portion of the extract as previously described (Bohmann and Tjian, 1989). The concentrations of the purified proteins were determined by comparing the intensity of coomassie staining with the staining intensity of BSA standards.

4. DNA Binding Experiments

Electrophoretic mobility shift assays were performed with the indicated amounts of proteins in 50 mM KCl, 25 mM HEPES, 0.05 mM EDTA, 5% glycerol, 1 mM DTT with 1 mg of poly(dI-dC) and 100 ng of BSA. The binding reactions and electrophoresis were carried out at room temperature. The samples were run on a 5% polyacrylamide, 0.5× TBE gel at 200 V.

5. Transfections

The full-length coding regions for each of the NFAT genes were subcloned into the RSV expression vector pREP4 (Invitrogen). The reporter plasmid was pXIL2-Luc (constructed by Jim Fraser). It contains the IL-2 promoter (−326 to +47, as in Durand et al 1988) upstream of the luciferase gene. Approximately $1 \times 10^6$ Jurkat cells were transiently transfected by lipofection (Lipofectin, Gibco/BRL). Twenty hours after transfection the cells were treated with 25 ng/ml PMA and 2 mM ionomycin, and the cells were harvested 8 hours after induction. Transfection efficiencies were standardized by co-transfection of pRSV-bgal and subsequent determination of bgal activity. Each transfection contained 2 mg of expression vector, 5 mg of luciferase reporter, and 1 mg of bgal plasmid and 10 ml of lipofectin. COS-7 and HepG2 cells were transfected by a modification of the calcium phosphate method (Chen and Okayama 1987). The reporter gene contained three copies of the antigen response element (−286 to −257) upstream of the herpes virus tk minimal promoter (−50 to +28) in the luciferase vector pGL2 (Promega).

6. Gel Filtration Columns and Glycerol Gradients

Protein samples were run on a 2.4 ml Superdex-200 column using the Pharmacia Smart system. The column was equilibrated with 0.5M KCl-HEG at a flow rate of 80 ml/min. The elution volumes of purified NFATc, NFATp, and p50 were determined relative to those of molecular weight standards. Purified p50 was provided by Zhaodan Cao. The following molecular weight standards (10 mg) were chromatographed on separate runs: thyroglobulin (669 kD), b-amylase (200 kD), BSA (66 kD), carbonic anhydrase (29 kD), and cytochrome c (12 kD). The elution volume ($V_e$) was converted to $K_{av}$ by the equation, $K_{av}=(V_e-V_o)/V_i$, where $V_o$ is the void volume and $V_i$ is the included volume. The Stokes radii were determined from a plot of $(-\log K_{av})^{1/2}$ vs. the Stokes radii of the standards (Ackers 1970).

The S values were determined by glycerol gradient centrifugation. Five ml 10–30% glycerol gradients were prepared using a Beckman density gradient former. The samples were centrifuged in a SW50Ti rotor at 39,000 rpm for 40 hours. After centrifugation, 200-ml fractions were collected and analyzed by gel electrophoresis and coomassie staining. The S values were determined by their sedimentation positions relative to the standards. Native molecular sizes were determined from the Stokes radii (a), S values (s), and the partial specific volumes (V) by the method of Siegel and Monty using the equation M=6pNas/1–V (Siegel and Monty 1966, Thompson et al. 1991).

7. References Cited in Experimental Section

Ackers (1970) *Adv. Prof. Chem.* 24:343–446; Baeuerle and Baltimore (1989) *Genes & Dev.* 3:1689–1698; Baeuerle and Henkel (1994) *Annu. Rev. Immunol.* 12:141–179; Boise et al. (1993) *Mol. Cell. Biol.* 13:1911–1919; Brabletz et al. (1991) *Nucl. Acids Res.* 19:61–67; Chen and Okayama (1987) *Mol. Cell. Biol.* 7:2745–2752; Choi et al. (1994) *Immunity* 1:179–187; Chomczynski and Sacchi (1987) *Anal. Biochem.* 162: 156–159; Chuvpilo et al. (1993) *Nucl. Acids Res.* 21:5694–5704; Clipstone and Crabtree (1992) *Nature* 357:695–697; Cockerill et al. (1993) *Proc. Natl. Acad. Sci. USA* 90:2466–2470; Durand et al. (1988) *Mol. Cell. Biol.* 8:1715–1724; Goldfeld et al. (1993) *J. Exp. Med.* 178:1365–1379; Grabstein et al. (1994) *Science* 264:965–968; Hohlfeld and Engel (1994) *Immunol. Today* 15:269–274; Hoyos et al. (1989) *Science* 244:457–460; Hope and Struhl (1987) *EMBO J.* 6:2781–2784; Jain et al. (1992) *Nature* 356:801–803; Jain et al. (1993) *Nature* 365:352–355; Jain et al. (1993) *J. Immunol.* 151:837–848; Jain et al. (1994) *Mol. Cell. Biol.* 14:1566–1574; Kadonaga and Tjian (1986) *Proc. Natl. Acad. Sci. USA* 83:5889–5893; Masuda (1993) *Mol. Cell. Biol.* 13:7399–7407; McCaffrey et al. (1993) *Science* 262:750–754; McCaffrey et al. (1993) *J. Biol. Chem.* 268:3747–3752; Mouzaki and Rungger (1994) *Blood* 84:2612–2621; Nolan (1994) *Cell* 77:795–798; Northrop (1994) *Nature* 369:497–502; Northrop (1993) *J. Biol. Chem.* 268:2917–2293; Randak (1990) *EMBO J.* 9:2529–2536; Rooney (1994) *EMBO J.* 13:625–633; Schreiber and Crabtree (1992) *Immunol. Today* 13:136–142; Shaw (1988) *Science* 241:202–205; Siegel and Monty (1966) *Biochim. Biophys. Acta* 112:346–362; Studier and Moffat (1986) *J. Mol. Biol.* 189:113–130; Szabo (1993) *Mol. Cell. Biol.* 13:4793–4805; Thompson et al . (1991) *Science* 253:762–768; Venkataraman et al. (1994) *Immunity* 1:189–196; Verweij et al. (1990) *J. Biol. Chem* 265:15788–15795; Yaseen et al. (1994) *Mol. Cell. Biol.* 14:6886–6895; and Yaseen et al. (1993) *J. Biol. Chem.* 268:14285–14293.

The following examples are offered by way of illustration and not by way of limitation.

EXAMPLES

1. Protocol for hNFAT-hNFAT Dependent Transcription Factor Binding Assay.

A. Reagents:

hNFAT: 20 µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P hNFAT 10× stock: $10^{-8}$–$10^{-6}$M "cold" hNFAT homolog supplemented with 200,000–250,000 cpm of labeled hNFAT homolog (Beckman counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of Assay Plates:

Coat with 120 µl of stock NF-AT per well overnight at 4° C.
Wash 2× with 200 µl PBS.
Block with 150 µl of blocking buffer.
Wash 2× with 200 µl PBS.

C. Assay:

Add 80 µl assay buffer/well.
Add 10 µl compound or extract.
Add 10 µl $^{33}$P-NFAT (20,000–25,000 cpm/0.3 pmoles/well= $3\times10^{-9}$M final concentration).
Shake at 25° C. for 15 min.
Incubate additional 45 min. at 25° C.
Stop the reaction by washing 4× with 200 µl PBS.
Add 150 µl scintillation cocktail.
Count in Topcount.

D. Controls for all Assays (Located on each Plate):

a. Non-specific binding (no hNFAT added)
b. cold hNFAT at 80% inhibition.

2. Protocol for hNFAT-AP1 Dependent Transcription Factor Binding Assay.

A. Reagents:

fos-jun heterodimers (junB and fra1): 20 µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P hNFAT 10× stock: $10^{-8}$–$10^{-6}$M "cold" hNFAT homolog supplemented with 200,000–250,000 cpm of labeled hNFAT homolog (Beckman counter). Place in the 4° C. microfridge during screening.
Protease inhibitor cocktail (1000×): 10 mg Trypsin Inhibitor (BMB #109894), 10 mg Aprotinin (BMB #236624), 25 mg Benzamidine (Sigma #B-6056), 25 mg Leupeptin (BMB #1017128), 10 mg APMSF (BMB #917575), and 2 mM NaVo$_3$ (Sigma #S-6508) in 10 ml of PBS.

B. Preparation of Assay Plates:

Coat with 120 µl of stock fos-jun heterodimers per well overnight at 4° C.
Wash 2× with 200 µl PBS.
Block with 150 µl of blocking buffer.
Wash 2× with 200 µl PBS.

C. Assay:

Add 80 µl assay buffer/well.
Add 10 µl compound or extract.
Add 10 µl $^{33}$P-NFAT (20,000–25,000 cpm/0.3 pmoles/well= $3\times10^{-9}$M final concentration).
Shake at 25° C. for 15 min.
Incubate additional 45 min. at 25° C.
Stop the reaction by washing 4× with 200 µl PBS.
Add 150 µl scintillation cocktail.
Count in Topcount.

D. Controls for all assays (located on each plate):

a. Non-specific binding (no hNFAT added)
b. cold hNFAT at 80% inhibition.

3. Protocol for hNFAT-fos-jun Dependent Transcription Factor—DNA Binding Assay.

A. Reagents:

Neutralite Avidin: 20 µg/ml in PBS.
Blocking buffer: 5% BSA, 0.5% Tween 20 in PBS; 1 hr, RT.
Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
$^{33}$P hNFAT 10× stock: $10^{-6}$–$10^{-8}$M "cold" hNFAT homolog supplemented with 200,000–250,000 cpm of labeled hNFAT homolog (Beckman counter) and $10^{-6}$–$10^{-8}$M fos-jun heterodimers. Place in the 4° C. microfridge during screening.
Protease inhibitor cocktail (1000×): 10 mg Trypsin Inhibitor (BMB #109894), 10 mg Aprotinin (BMB #236624), mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

Oligonucleotide stock: (specific biotinylated). Biotinylated oligo at 17 pmole/μl AP1-NFAT site: (BIOTIN)-GG AGG AAA AAC TGT TTC ATA CAG AAG GCG T (SEQ ID NO:18)

B. Preparation of Assay Plates:

Coat with 120 μl of stock N-Avidin per well overnight at 4° C.

Wash 2× with 200 μl PBS.
Block with 150 μl of blocking buffer.
Wash 2× with 200 μl PBS.

C. Assay:

Add 40 μl assay buffer/well.
Add 10 μl compound or extract.
Add 10 μl $^{33}$P-NFAT (20,000–25,000 cpm/0.1–10 pmoles/well=$10^{-9}$–$10^{-7}$M final concentration).
Shake at 25° C. for 15 min.
Incubate additional 45 min. at 25° C.
Add 40 μl oligo mixture (1.0 pmoles/40 μl in assay buffer with 1 ng of ss-DNA)
Incubate 1 hr at RT.
Stop the reaction by washing 4× with 200 μl PBS.
Add 150 μl scintillation cocktail.
Count in Topcount.

D. Controls for all Assays (Located on each Plate):
a. Non-specific binding (no oligo added)
b. Specific soluble oligo at 80% inhibition.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated nucleic acid encoding a human nuclear factor of activated T-cells, hNFAT, protein comprising hNFATp$_1$(SEQ ID NO:2), hNFATp$_2$ (SEQ ID NO:2, residues 220–921), hNFAT3 (SEQ ID NO:6), hNFAT4b (SEQ ID NO:10) or hNFAT4c (SEQ ID NO:12).

2. The isolated nucleic acid of claim 1, wherein said protein comprises hNFATp$_1$(SEQ ID NO:2).

3. The isolated nucleic acid of claim 1, wherein said protein comprises hNFATp$_2$ (SEQ ID NO:2, residues 220–921).

4. The isolated nucleic acid of claim 1, wherein said protein comprises hNFAT3 (SEQ ID NO:6).

5. The isolated nucleic acid of claim 1, wherein said protein comprises hNFAT4b (SEQ ID NO:10).

6. The isolated nucleic acid of claim 1, wherein said protein comprises hNFAT4c (SEQ ID NO:12).

7. An isolated nucleic acid encoding an hNFAT protein, said nucleic acid comprising SEQ ID NO:1, SEQ ID NO:5, SEQ ID NO:9, SEQ ID NO:11 or nucleotides 1–356 and 868–3478 of SEQ ID NO:1.

8. The isolated nucleic acid of claim 7, wherein said nucleic acid comprises SEQ ID NO:1.

9. The isolated nucleic acid of claim 7, wherein said nucleic acid comprises nucleotides 1–356 and 868–3478 of SEQ ID NO:1.

10. The isolated nucleic acid of claim 7, wherein said nucleic acid comprises SEQ ID NO:5.

11. The isolated nucleic acid of claim 7, wherein said nucleic acid comprises SEQ ID NO:9.

12. The isolated nucleic acid of claim 7, wherein said nucleic acid comprises SEQ ID NO:1.

* * * * *